(12) United States Patent
Xie et al.

(10) Patent No.: US 6,809,866 B2
(45) Date of Patent: Oct. 26, 2004

(54) OPTICAL IMAGING APPARATUS

(75) Inventors: Tianyu Xie, Akiruno (JP); Mamoru Kaneko, Hanno (JP); Toshiro Okamura, Hino (JP); Yasuhiro Kamihara, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/207,676

(22) Filed: Jul. 29, 2002

(65) Prior Publication Data

US 2003/0048540 A1 Mar. 13, 2003

(30) Foreign Application Priority Data

Aug. 3, 2001 (JP) .................................. 2001-237076
Apr. 5, 2002 (JP) .................................. 2001-104424
May 29, 2002 (JP) .................................. 2002-156089

(51) Int. Cl.$^7$ ............................................. G02B 27/10
(52) U.S. Cl. .................... 359/618; 359/212; 359/223; 359/626; 359/627
(58) Field of Search ................................ 359/618, 626, 359/627, 212, 223, 224, 389, 385, 233, 234, 362, 368, 379, 380, 381, 395, 679, 639, 833; 356/609, 450, 479, 484, 497, 608, 601, 607; 600/425, 476

(56) References Cited

U.S. PATENT DOCUMENTS

| | | | | |
|---|---|---|---|---|
| 5,120,953 A | * | 6/1992 | Harris ...................... | 250/227.2 |
| 5,245,173 A | * | 9/1993 | Yamana et al. ............ | 250/201.3 |
| 5,608,529 A | * | 3/1997 | Hori .......................... | 356/609 |
| 5,784,202 A | * | 7/1998 | Noguchi ..................... | 359/618 |
| 5,788,639 A | * | 8/1998 | Zavislan et al. ............ | 600/476 |
| 6,057,920 A | * | 5/2000 | Fercher et al. .............. | 356/497 |
| 6,151,127 A | * | 11/2000 | Kempe ........................ | 356/484 |
| 6,433,910 B2 | * | 8/2002 | Suga ........................... | 359/212 |
| 2002/0100864 A1 | * | 8/2002 | Wake ........................... | 250/208.1 |
| 2003/0004412 A1 | * | 1/2003 | Izatt et al. .................. | 600/425 |
| 2003/0034935 A1 | * | 2/2003 | Amanai et al. .............. | 345/7 |
| 2003/0038948 A1 | * | 2/2003 | Prinzhausen et al. ........ | 356/497 |

FOREIGN PATENT DOCUMENTS

| | | |
|---|---|---|
| JP | 6-154228 | 6/1994 |
| JP | 11-72431 | 3/1999 |

OTHER PUBLICATIONS

Hoeling, B.M., et al., "An optical coherence microscope for 3-dimensional imaging in developmental biology", Optics Express, vol. 6, No. 7, pp. 136–145.

* cited by examiner

Primary Examiner—Ricky Mack
Assistant Examiner—Brandi N Thomas
(74) Attorney, Agent, or Firm—Scully, Scott, Murphy & Presser

(57) ABSTRACT

An optical imaging apparatus includes an optical probe and an apparatus main body which controls and drives the optical probe via a connecting cable. The optical probe includes a low-coherence light source, a half mirror, an XY reflecting mirror scan, an objective optical system, a reflecting mirror, a modulating mirror, and a photo detector. In the optical probe, the modulating mirror and the objective optical system, as optical path length interlockingly adjusting elements, are integrally arranged to an optical path length interlockingly adjusting base, together with a reflecting-side lens. The optical probe has an advancing and regressing driving unit which advances and regresses the optical path length interlockingly adjusting base in the optical axis direction (Z direction).

18 Claims, 46 Drawing Sheets

SUBJECT PORTION (SIMULTANEOUSLY DISPLAY, COMPARE, AND SEARCH)

(SIMULTANEOUSLY DISPLAY, COMPARE, AND SEARCH)

OPTICAL IMAGING APPARATUS

This application claims benefit of Japanese Application No. 2001-237076 filed in Japan on Aug. 3, 2001, No. 2002-104424 filed in Japan on Apr. 5, 2002, No. 2002-156089 filed in Japan on May 29, 2002, the contents of which are incorporated by this reference.

BACKGROUND OF THE INVENTION

1. Field of the Invention

The present invention relates to an optical imaging apparatus for obtaining optical image information of a subject portion by scanning with beams from a light source.

2. Description of the Related Art

Recently, an optical imaging apparatus called an OCT (Optical Coherence Tomography) has widely been used. The optical imaging apparatus forms a tomogram of the inside of a subject portion based on information on light which returns from the subject portion by irradiating the subject portion with light having low coherence caused in a light source and then scanning a focus position.

As disclosed in U.S. Pat. No. 6,151,127, Optics Express Vol. 6, No. 7, 136–145 (Optical Society of America, on March, 2000), and Japanese Unexamined Patent Application Publication No. 11-72431 which was applied by the present applicant, the above-mentioned optical imaging apparatus can obtain a three-dimensional tomogram of a subject portion by two-dimensionally scanning the subject portion with an objective optical system for condensing light with low coherence to the subject portion and by scanning it in an optical axis direction.

An optical system of the above-mentioned conventional optical imaging apparatus separates the light with the low coherence generated by the light source into irradiation light and reference light by light separating means, scans (two-dimensionally scans) the subject portion with the separated irradiation light, and condenses the light to the subject portion at a focus point of the objective optical system. Then, reflection light and scattering light of the subject portion from the focus point pass through the same optical path as that of the irradiation light, and return to the light separating means again. In this case, the subject portion in the depth direction is scanned by the scanning operation in the optical direction with the objective optical system.

On the other hand, the reference light separated by the light separating means is reflected by reference light reflecting means, and is returned to the light separating means again. Then, the reference light reflecting means advances and regresses in the optical axis direction so that the length of the optical path of the reflected reference light is almost equal to the lengths of the optical paths of the reflection light and the scattering light from the subject portion.

The reflected reference light and the reflection light and scattering light from the subject portion, having almost the same length of the optical paths interfere each other, and an optical detector as optical detecting means detects these light. An output of the optical detector is demodulated by a demodulator and an interfered optical signal is extracted. The extracted optical signal is converted into a digital signal, is thereafter subjected to signal processing, and image data corresponding to the tomogram is generated. The generated image data is displayed on a monitor as a three-dimensional tomogram of the subject portion.

However, the above-mentioned conventional optical imaging apparatus independently comprises means for advancing and regressing the above-described objective optical system in the optical axis direction and means for advancing and regressing the reference-light reflecting means in the optical axis so that the length of the optical path of instrumentation light matches that of the reference light. Consequently, the above-mentioned conventional optical imaging apparatus has two drive systems.

Thus, the above-mentioned conventional optical imaging apparatus has a larger optical system. When it is incorporated in an endoscope insertion portion or an optical scanning probe which is used by being inserted into the body cavity, there is such a problem that the diameter of these insertion portions becomes large.

Further, the above-mentioned conventional optical imaging apparatus has two control systems for individually controlling the above drive systems. The two drive systems must be controlled synchronously with the two control systems. Therefore, the above-mentioned optical imaging apparatus has complex structures of the control systems and, thus, costs are increased.

The optical imaging apparatus has, for example, an optical probe for scanning the anatomy of the subject portion with laser beams (coherent beams) from the light source and for condensing the light at the focus point of the objective optical system. The optical probe has a conjugate focus-point optical system for obtaining the tomogram of the anatomy by receiving return light, as the reflection light and the scattering light from the anatomy of the subject portion obtained via the objective optical system, by receiving light means having a conjugate focus point of the objective optical system.

As disclosed in, for example, U.S. Pat. No. 5,788,639, the above optical imaging apparatus is proposed, in which the entire optical system is arranged onto a single base and this base is moved in the horizontal direction, thus adjusting a range of a field of view for observation in the horizontal direction. Therefore, in the optical imaging apparatus disclosed in the U.S. Pat. No. 5,788,639, the range of the field of view for observation as a fine observation range is moved in the horizontal direction of the subject portion and the field of view of the objective optical system can be arranged.

On the other hand, as disclosed in, for example, U.S. Pat. No. 5,120,953, an optical imaging apparatus is proposed, in which a surface of the anatomy of a subject portion is absorbed, thereby adjusting the range of the field of view for observation in the vertical direction (depth direction) of the subject portion. Thus, in the optical imaging apparatus disclosed in U.S. Pat. No. 5,120,953, the range of the field of view for observation as a fine observation range can be adjusted in the vertical direction.

As disclosed in Japanese Unexamined Patent Application Publication No. 6-154228 which was applied by the present applicant, an optical imaging apparatus is proposed, in which a TV camera for image pick-up of a surface observation image within the range of the field of view for observation is provided. Consequently, the optical imaging apparatus disclosed in Japanese Unexamined Patent Application Publication No. 6-154228 can simultaneously display both the surface observation image and the tomogram of the subject portion.

Upon moving and adjusting the base on which the entire optical system is arranged, the optical imaging apparatus disclosed in U.S. Pat. No. 5,788,639 requires the adjustment of the optical axis with high accuracy. Thus, in the optical imaging apparatus disclosed in the U.S. Pat. No. 5,788,639, the adjustment of the optical axis is complicated and is difficult.

In the optical imaging apparatus disclosed in U.S. Pat. No. 5,788,639, the base on which the entire optical system is arranged is moved and adjusted. Therefore, the arrangement of the moving and adjusting means in the optical probe causes such a problem that the whole optical probe is increased.

Meanwhile, in the optical imaging apparatus disclosed in U.S. Pat. No. 5,120,953, the range of the field of view for observation can be adjusted in the vertical direction (depth direction) of the subject portion. However, there is such a problem that the range of the field of view for observation cannot be adjusted in the horizontal direction of the subject portion.

Further, in the optical imaging apparatus disclosed in Japanese Unexamined Patent Application Publication No. 6-154228, both the surface observation image and the tomogram of the subject portion can simultaneously be displayed. However, there is such a problem that the range of the field of view for observation cannot be adjusted in the horizontal direction and the vertical direction (depth direction) of the subject portion.

Recently, endoscopes have widely been used in medical fields and industrial fields. As disclosed in Japanese Unexamined Patent Application Publication No. 6-154228, in addition to a normal observation image obtained by the endoscope, an optical tomogram can be obtained with low-coherence light for purpose of the detailed diagnosis about a lesion portion.

In the conventional art, the dimension of the insertion portion in the endoscope can be made thinner because the objective optical system is shared for the normal observation and the optical tomogram using the low-coherence light.

However, in the above-mentioned conventional art, the same numerical aperture (hereinafter, abbreviated to an NA) of the objective optical system is used for both the normal observation and the optical tomogram using the low-coherence light and, therefore, there is a problem to be solved.

More specifically, in the normal usage, first, in a normal observation state, a wide portion is macro-observed. When there is a portion which might be the lesion portion as the observation result, a method is used whereby the case is examined in detail by enlargedly observing a part of the lesion portion with the optical tomogram.

In this case, in the conventional art, the objective optical system is shared and the NA is in the same state. Consequently, in the state suited to the normal observation, a resolution is insufficient for the state of the optical tomogram. On the contrary, in the state of the optical tomogram, the resolution is high by the high NA, a wide field of view cannot be ensured for the normal observation and thus only a narrow range can be observed.

In addition, there is another conventional art using individual optical systems for macro observation and optical tomogram. However, in the endoscope which is inserted in the body cavity as mentioned above, it is difficult to make the diameter of the optical imaging apparatus thinner.

Further, in the case of the other observation art using the individual optical systems, there is such a drawback that the apparatus is increased in size. Moreover, there is such a drawback that when enlarging and observing the lesion portion in the image for macro observation with the optical tomogram, a position to be enlarged and observed with the optical tomogram in the macro image is easily changed in accordance with the change in distance or the like.

OBJECTS AMD SUMMARY OF THE INVENTION

It is one object of the present invention to provide an optical imaging apparatus in which an optical system can be reduced in size and a control system can simply be structured.

Also, it is another object of the present invention to provide an optical imaging apparatus with a small size and a high resolution, in which a field of view for observation can easily be moved within a wide range.

Further, it is another object of the present invention to provide an optical imaging apparatus with high convenience, in which both a normal macro image and an enlargedly observed image with a high resolution due to low-coherence light can be obtained by commonly using a part of an optical system so as to arrange the optical imaging apparatus to an endoscope insertion portion.

Furthermore, it is another object of the present invention to provide an optical imaging apparatus used for endoscopes, etc., which is made thinner in diameter and thus can be arranged in an endoscope insertion portion and in which both a normal macro image and an enlargedly observed image with a high resolution due to high-coherence light in an improved convenience state can be obtained.

An optical imaging apparatus comprises: a low-coherence optical system which guides low-coherence light from a low-coherence light source to a subject portion and further guides return light from the subject portion to light receiving means; light separating means arranged to the low-coherence optical system, which separates the low-coherence light from the low-coherence light source into instrumentation light and reference light; horizontal scanning means arranged to the low-coherence optical system, which horizontally scans the subject portion with the instrumentation light separated by the light separating means; reference light reflecting means arranged to the low-coherence optical system, which reflects the reference light separated by the light separating means and returns the reflected light to the light separating means; an objective optical system arranged to the low-coherence optical system, which condenses the instrumentation light horizontally scanned by the horizontal scanning means to the subject portion and further captures return instrumentation-light from the subject portion; optical path length interlockingly adjusting means which interlockingly matches the length of an optical path of the instrumentation light to that of the reference light; and signal processing means which performs signal processing of an electronic signal converted photoelectrically by the light receiving means and obtains a surface image or a tomogram of the subject portion.

An optical imaging apparatus comprises: an optical system which guides beams from a light source to a subject portion and further guides return light from the subject portion to light receiving means; optical scanning means arranged to the optical system, which scans the subject portion with the beams from the light source; an objective optical system arranged to the optical system, which condenses the beams for scanning by the optical scanning means to the subject portion and further captures return light from the subject portion; positioning means arranged in a field of view for observation of the objective optical system, which comes into contact with the subject portion and performs positioning; field of view position adjusting means which moves the positioning means relative to the objective optical system in a contact state of the positioning means with the subject portion and adjusts the position in the field of view of the objective optical system; and signal processing means which performs signal processing of an electronic signal converted photoelectrically by the light receiving means and obtains a surface image or a tomogram of the subject portion.

An optical imaging apparatus comprises: an optical system which guides beams from a light source to a subject portion and further guides return light from the subject portion to light receiving means; a normal optical system in which at least a part thereof is the same as the optical system and which has a numerical aperture smaller than that of the optical system, a focusing distance longer than that of the optical system, an object observation range wider than that of the optical system, or a diameter of the object observation range wider than that of the optical system, and which captures a normal optical image of the subject portion and forming the captured normal optical image by image pickup means; and signal processing means which performs signal processing of an electronic signal photoelectrically converted by the light receiving means, obtains a surface image or a tomogram of the subject portion, performs signal processing the electronic signal converted photoelectrically by the image pick-up means, and obtains a normal optical image.

These objects and advantages of the present invention will become further apparent from the following detailed explanation.

DETAILED DESCRIPTION OF THE PREFERRED EMBODIMENTS

Hereinbelow, embodiments of the present invention will be described with reference to the drawings.

First Embodiment

Figure 1:
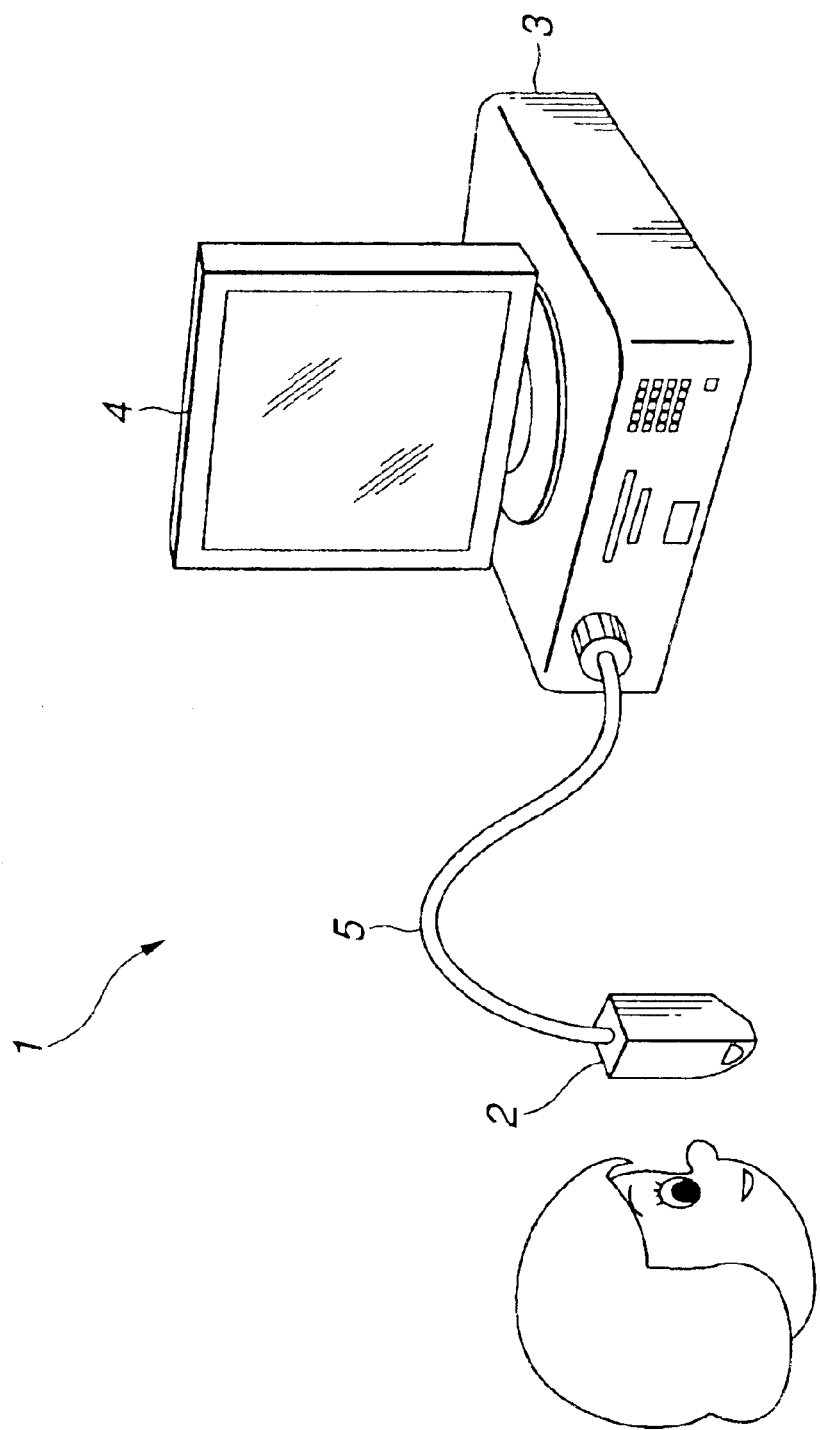
FIG. 1 is a diagram of the appearance showing the entire structure of an optical imaging apparatus according to a first embodiment of the present invention.
Figure 2:
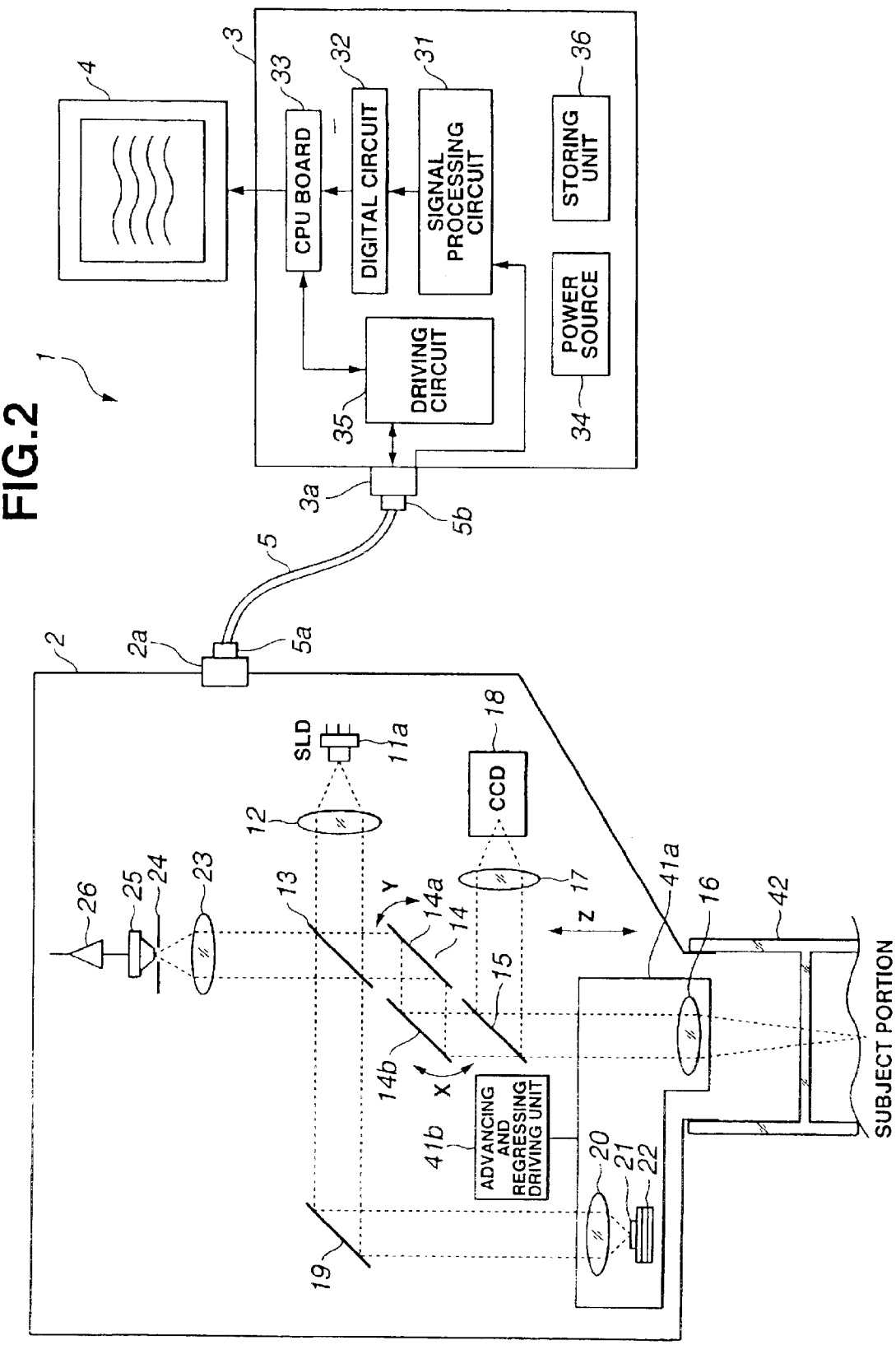
FIG. 2 is an explanatory diagram showing the internal structure of an optical probe and a main body of the apparatus in FIG. 1.
Figure 3:
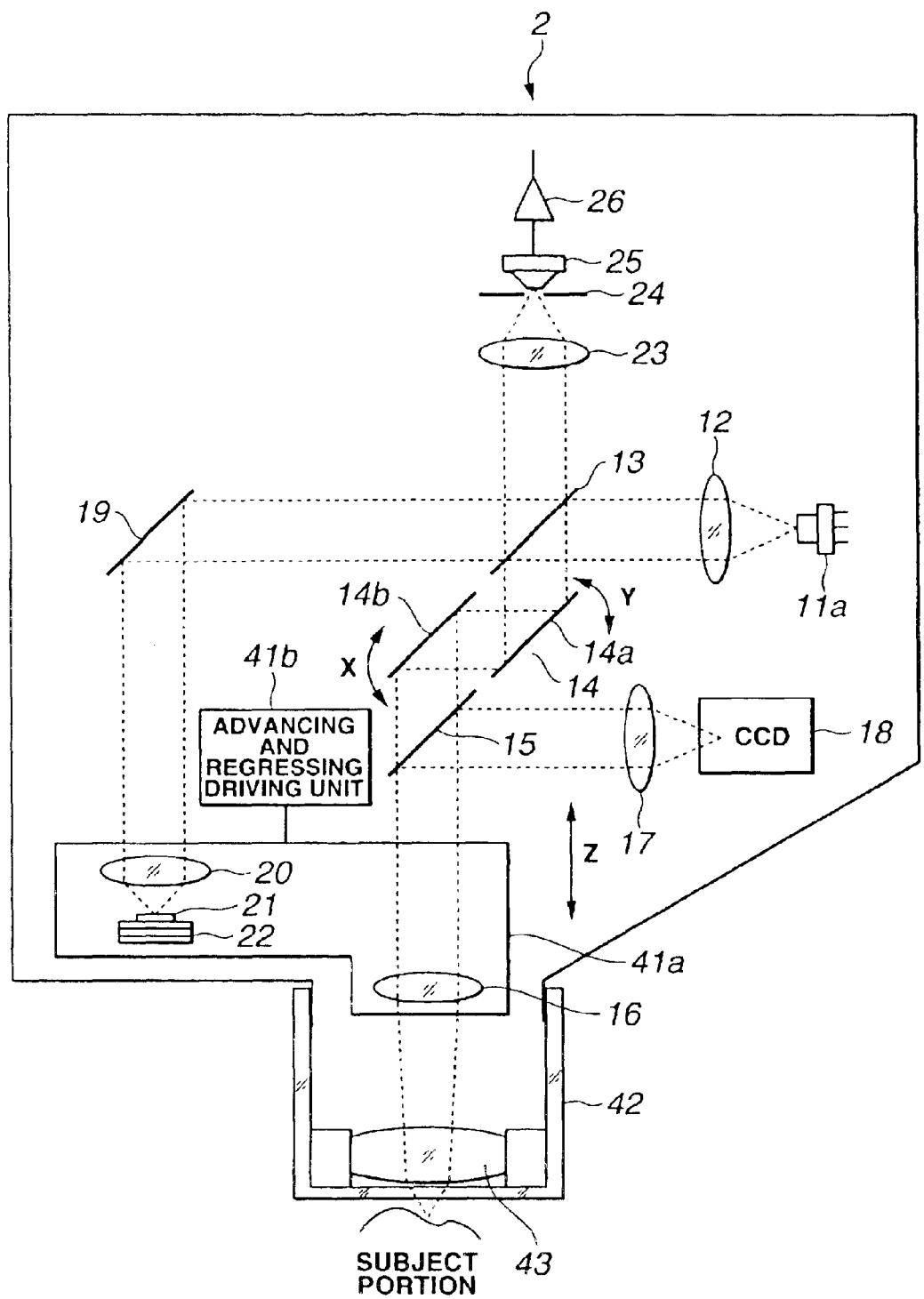
FIG. 3 is an explanatory diagram showing the internal structure of an optical probe according to a first modification of FIG. 2.
Figure 4:
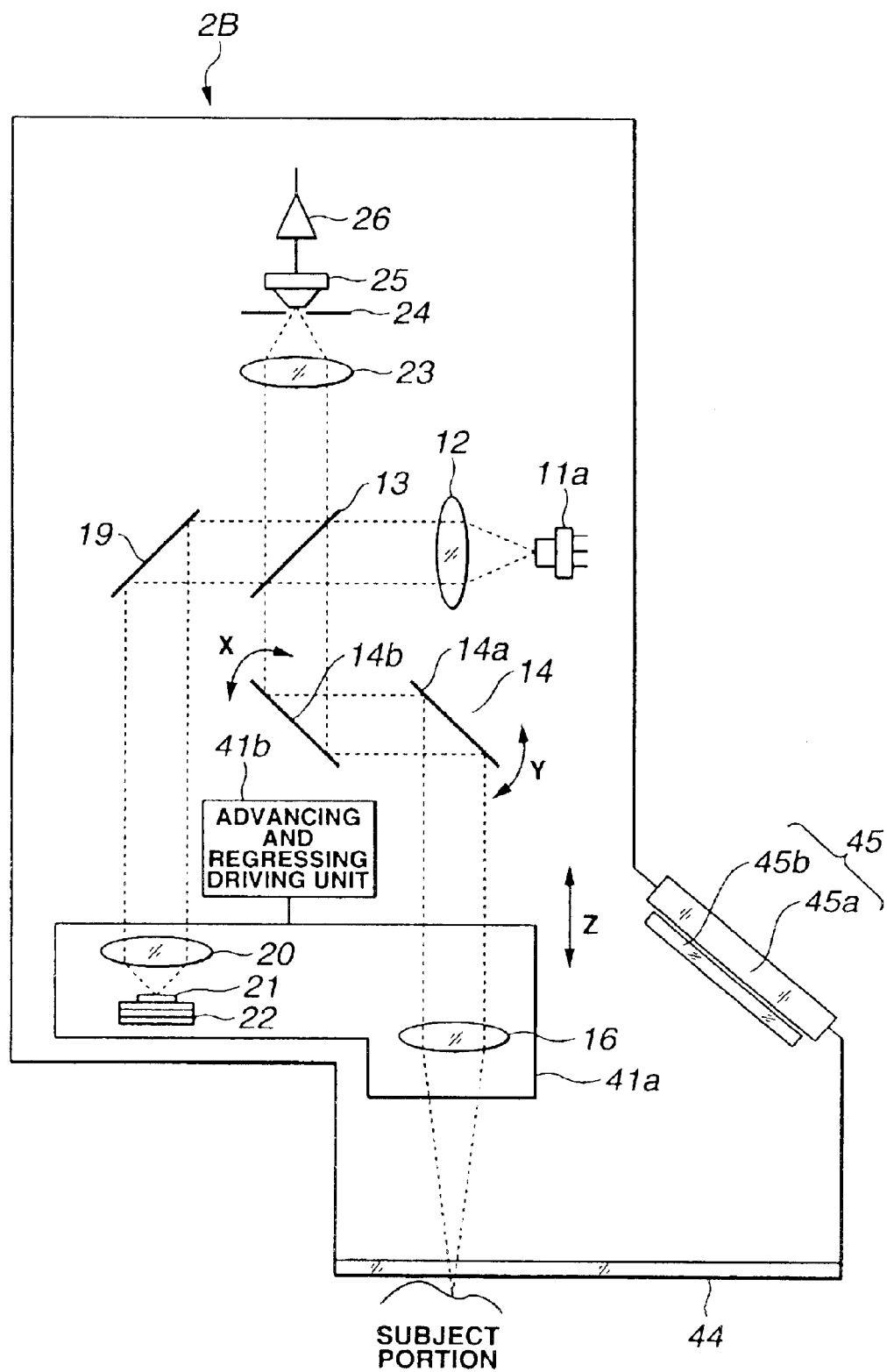
FIG. 4 is an explanatory diagram showing the internal structure of an optical probe according to a second modification of FIG. 2.
Figure 5:
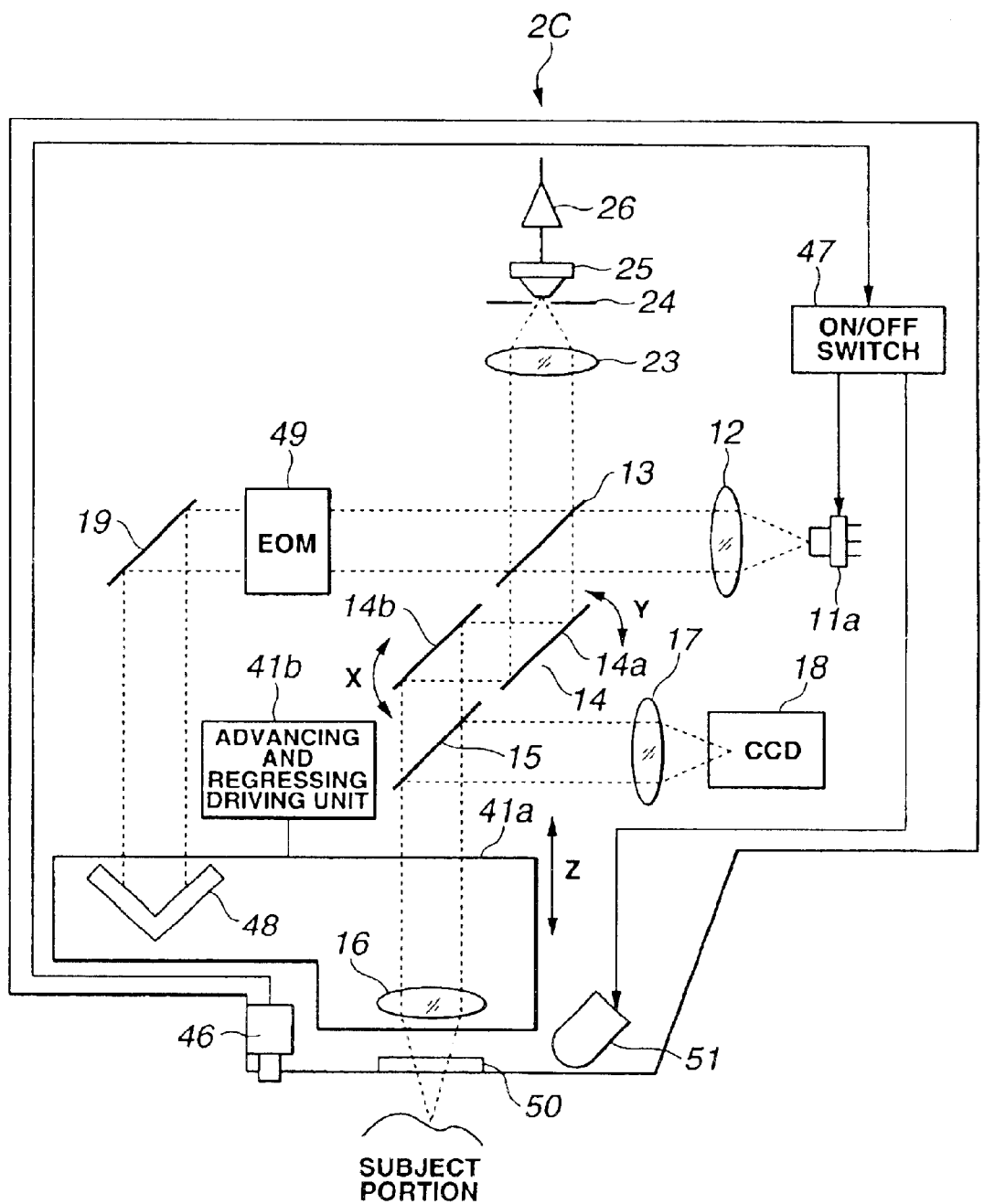
FIG. 5 is an explanatory diagram showing the internal structure of an optical probe according to a third modification of FIG. 2.

FIGS. 1 to 5 relate to a first embodiment of the present invention, FIG. 1 is a diagram of the appearance showing the entire structure of an optical imaging apparatus according to the first embodiment of the present invention, FIG. 2 is an explanatory diagram showing the internal structure of an optical probe and a main body of the apparatus in FIG. 1, FIG. 3 is an explanatory diagram showing the internal structure of an optical probe according to a first modification of FIG. 2, FIG. 4 is an explanatory diagram showing the internal structure of an optical probe according to a second modification of FIG. 2, and FIG. 5 is an explanatory diagram showing the internal structure of an optical probe according to a third modification of FIG. 2.

Referring to FIG. 1, an optical imaging apparatus 1 according to the first embodiment comprises an optical scanning probe (hereinafter, abbreviated to an optical probe) 2, an apparatus main body 3 for controlling and driving the optical probe 2, and a monitor 4 for displaying an image. The optical probe 2 is connected to the apparatus main body 3 via a connecting cable 5.

Referring to FIG. 2, the optical probe 2 comprises a connector bearing portion 2a to which a connector portion 5a in the connecting cable 5 can detachably be connected. Meanwhile, the apparatus main body 3 comprises a connector bearing portion 3a to which a connector portion 5b at another end of the connecting cable 5 can detachably be connected. Thus, the optical probe 2 can detachably be connected to the apparatus main body 3 and also can detachably be connected to the connecting cable 5.

The optical probe 2 has a low-coherence light source 11a. The low-coherence light source 11a has a wavelength of, for example, 980 nm and has optical characteristics of low-coherence light showing the coherence only within a short distance such as a coherent distance of approximately 15 μm. That is, if the low-coherence light is divided into two and thereafter is mixed again, it is detected as coherent light when the difference between lengths of two optical paths to the dividing point is within the short distance of approximately 15 μm. When the low-coherence light has a longer length of the two optical paths than approximately 15 μm, the low-coherence light source 11a has characteristics of non-coherence.

Light generated in the low-coherence light source 11a is made parallel by a light-source-side lens 12, and is separated into instrumentation light and reference light by a half mirror 13 as optical dividing means. Incidentally, in place of the half mirror 13, an optical coupler may be used as the optical dividing means.

The instrumentation light divided by the half mirror 13 is incident on an XY reflecting mirror scan 14 as horizontal scanning means, and a subject portion is scanned in the horizontal direction by the XY reflecting mirror scan 14. Herein, the subject portion is scanned in a Y direction with the instrumentation light by a Y scanning mirror 14a and, next, it is scanned in an X direction with the instrumentation light by an X scanning mirror 14b. Incidentally, the X scanning mirror 14b and the Y scanning mirror 14a are driven by driving units (not shown). The driving units are controlled and driven by a driving circuit (which will be described later) of the apparatus main body 3, synchronously with a signal from optical detecting means which will be described later.

The instrumentation light upon scanning in the horizontal direction by the XY reflecting mirror scan 14 is transmitted to an objective optical system 16 having a large numerical aperture (NA) via a wavelength separating mirror 15, and is condensed to the subject portion at the focus point of the objective optical system 16. Reflection light and scattering light of the subject portion from the focus point pass through the same optical path as that of irradiation light. Then, only the instrumentation light having the same wavelength as that of the irradiation light passes through the same optical path by using the wavelength separating mirror 15 and is returned to the half mirror 13 again.

Light except for the above-mentioned one is reflected and is incident on a CCD-side lens 17. Namely, the objective optical system 16, and a light-receiving-side lens 23 and a pin hole 24 (which will be described later) have a conjugate focus point. The reflection light from points excluding the focus point of the objective optical system 16 is hardly incident on the pin hole 24. Therefore, the optical probe 2 has a conjugate focus point optical system.

In this case, the focus point is scanned in the depth direction of the subject portion by scanning the subject portion by the objective optical system 16 in the optical axis direction by using optical path length interlockingly adjusting means. The light of the wavelength except for the instrumentation light reflected by the wavelength separating mirror 15 is condensed to the CCD-side lens 17, and is received by a light receiving surface of a CCD 18 for surface observation. Then, an image is picked up by the CCD 18 for surface observation.

The instrumentation light returned to the half mirror 13 side is incident on a photo detector 25 as optical detecting means, which will be described later.

The reference light divided by the half mirror 13 is reflected by the reflecting mirror 19, is condensed by a reflecting-side lens 20, and is incident on a modulating mirror 21 as reference light reflecting means. The modulating mirror 21 has a piezoelectric element 22, as light modulating means, which is attached to the bottom thereof. The piezoelectric element 22 vibrates the modulating mirror 21 by applying a drive signal from a driving circuit in the apparatus main body 3, which will be described later.

The reference light incident on the modulating mirror 21 is modulated and is reflected. Then, the reference light becomes parallel by the reflecting-side lens 20, and returns to the half mirror 13 again. Incidentally, the reflecting-side lens 20 is arranged so that the reference light returned from the modulating mirror 21 is certainly incident on the pin hole 24, which will be described later. The reference light returned to the half mirror 13 is reflected by the half mirror 13, and is incident on the photo detector 25 as optical detecting means, which will be described later.

In this case, the modulating mirror 21 advances and regresses in the optical axis direction by optical path interlockingly adjusting means which will be described later so that the length of the optical path of the reflected reference light is almost equal to the length of the optical path of the instrumentation light.

The reference light and the instrumentation light having almost the same length of the optical paths interferes on the optical path from the half mirror 13 side. The interference light is condensed by the light-receiving-side lens 23 and is received by the photo detector 25 as optical detecting means via the pin hole 24.

The photo detector 25 photoelectrically converts the coherent light into an coherent electrical signal. The interference electronic signal, which is photoelectrically converted, is amplified by an amplifier 26, and is sent to the apparatus main body 3 via a signal line which is inserted into the connecting cable 5.

The coherent electronic signal received by the apparatus main body 3 is inputted to the signal processing circuit 31 and is subjected to signal processing of the coherent electronic signal by the signal processing circuit 31. An output from the signal processing circuit 31 is converted into a digital signal by a digital circuit 32 and, thereafter, is inputted to a CPU board 33. The CPU board 33 generates image data corresponding to the tomogram based on the inputted digital signal. The generated image data is outputted to the monitor 4 and is displayed on a display screen as a three-dimensional tomogram of the subject portion (OCT tomogram).

An image pick-up signal whose image is picked up by the CCD 18 for surface observation is inputted to the apparatus main body 3 via the signal line which is inserted into the connecting cable 5, and is displayed onto the display screen of the monitor 4 as an image for surface observation after signal processing.

The apparatus main body 3 comprises a power supply 34 and a driving circuit 35.

The power supply 34 supplies drive power to the low-coherence light source 11a, the photo detector 25, the piezoelectric element 22, a driving unit of the XY reflecting mirror scan 14, and the CCD 18 for surface observation via the power supply line which is inserted into the connecting cable 5.

The driving circuit 35 controls the drive operation of the low-coherence light source 11a, the photo detector 25, the piezoelectric element 22, the driving unit of the XY reflecting mirror scan 14, and the CCD 18 for surface observation in the optical probe 2 via the signal line which is inserted into the connecting cable 5.

The apparatus main body 3 has a storing unit 36 such as a hard disk. The storing unit 36 can store drive control conditions upon controlling the drive operation by the driving circuit 35, and image data such as the three-dimensional tomogram and the image for surface observation.

According to the first embodiment, the reflecting-side lens 20, the modulating mirror 21, and the objective optical system 16, as the optical path interlockingly adjusting means, are integrally arranged to an optical path length interlockingly adjusting base 41a. An advancing and regressing driving unit 41b for advancing and regressing the optical path length interlockingly adjusting base 41a in the optical axis direction (Z axis direction) is arranged.

The advancing and regressing driving unit 41b is controlled and driven by the driving circuit 35 in the apparatus main body 3 via the signal line which is inserted into the connecting cable 5 synchronously with the coherent electronic signal outputted from the photo detector 25, and advances or regresses the optical path length interlockingly adjusting base 41a in the optical axis (Z axis direction).

Thus, according to the first embodiment, the optical probe 2 can move the objective optical system 16 and the modulating mirror 21 together with the reflecting-side lens 20 in parallel with the same distance. Then, the length of the optical path of the instrumentation light from the low-coherence light source 11a to a focus point condensed by the objective optical system 16 and from the focus point to the photo detector 25 can match the length of the optical path of the reference light sent from the low-coherence light source 11a to the light modulating mirror 21 and from the light modulating mirror 21 to the photo detector 25.

Therefore, according to the first embodiment, the optical probe 2 can simultaneously drive both the objective optical system 16 and the modulating mirror 21 by using only one drive system. Thus, advantageously, the optical system can be reduced in size and the control drive system is simplified.

The optical probe 2 comprises a transparent cap 42 which is arranged to the position opposed to the subject portion. The transparent cap 42 can detachably be attached, For example, the bottom of the transparent cap 42 is generally made of a transparent member and the periphery thereof is formed of an ND (Neutral Density) filter or an infrared cut filter. The transparent cap 42 positions an examined portion of the subject portion by the optical probe 2, and can check a state of the examined portion of the subject portion when scanning at the determined position by the optical probe 2. Further, the transparent cap 42 can suppress shaking by positioning the examined portion of the subject portion by using the optical probe 2.

Furthermore, the transparent cap 42 may be structured as shown in FIG. 3.

Referring to FIG. 3, the transparent cap 42 may comprise an optical member 43 such as an enlargement lens for purpose of the adjustment of the focusing distance, the adjustment of a spot of the instrumentation light, or the adjustment of the resolution.

In addition, referring to FIG. 4, the optical probe may comprise an observation window.

As shown in FIG. 4, an optical probe 2B integrally has a transparent member 44 at the position opposed to the subject portion and an observation window 45 which is capable of observing the examined portion of the subject portion at the position opposed thereto.

The observation window 45 comprises a Fresnel lens 45a such as the enlargement lens which is exposed to the surface of the outer circumference and a reticle 45b as marker means, which is arranged at the rear surface of the Fresnel lens 45a. Incidentally, the reticle 45b is formed of the ND filter or the infrared cut filter. The optical probe 2B can observe the surface of the subject portion by using the above-mentioned observation window 45. Therefore, the wavelength separating mirror 15, the CCD-side lens 17, and the CCD 18 for surface observation are not arranged and, however, they may be arranged. Thus, the optical probe 2B can have the shorter length, corresponding to the absence of the transparent cap 42.

Moreover, referring to FIG. 5, the optical probe may comprise a switch for contact detection at the position opposed to the subject portion.

As shown in FIG. 5, an optical probe 2C may comprise a switch 46 for contact detection at the position opposed to the subject portion, which comes into contact with the examined portion of the subject portion.

The switch 46 for contact detection is connected to an on/off switch 47 which switches of/off the low-coherence light source 11a, thereby coming into contact/non-contact with the examined portion of the subject portion. Thus, the low-coherence light source 11a is turned on/off.

Incidentally, in the optical probe 2C, the optical system is changed as the following description.

That is, in place of the modulating mirror 21 as the preference light reflecting means, the optical probe 2C uses a corner-cube or corner-cube reflector 48. As the light modulating means, in place of the piezoelectric element 22, an electro-optic modulator (EOM) 49 is used. In place of the EOM 49, an acousto-optic modulator (AOM) (not shown) may be used.

The optical probe 2C comprises a transparent irradiation window 50 at the position opposed to the subject portion. Further, the optical probe 2C comprises an illumination light source 51 for CCD which is used for the CCD 18 for surface observation. The illumination light source 51 for CCD is connected to the on/off switch 47. Similarly to the low-coherence light source 11a, the switch 46 for contact detection comes into contact/non-contact with the examined portion of the subject portion, thereby switching on/off the illumination light source 51 for CCD.

Second Embodiment

Figure 6:
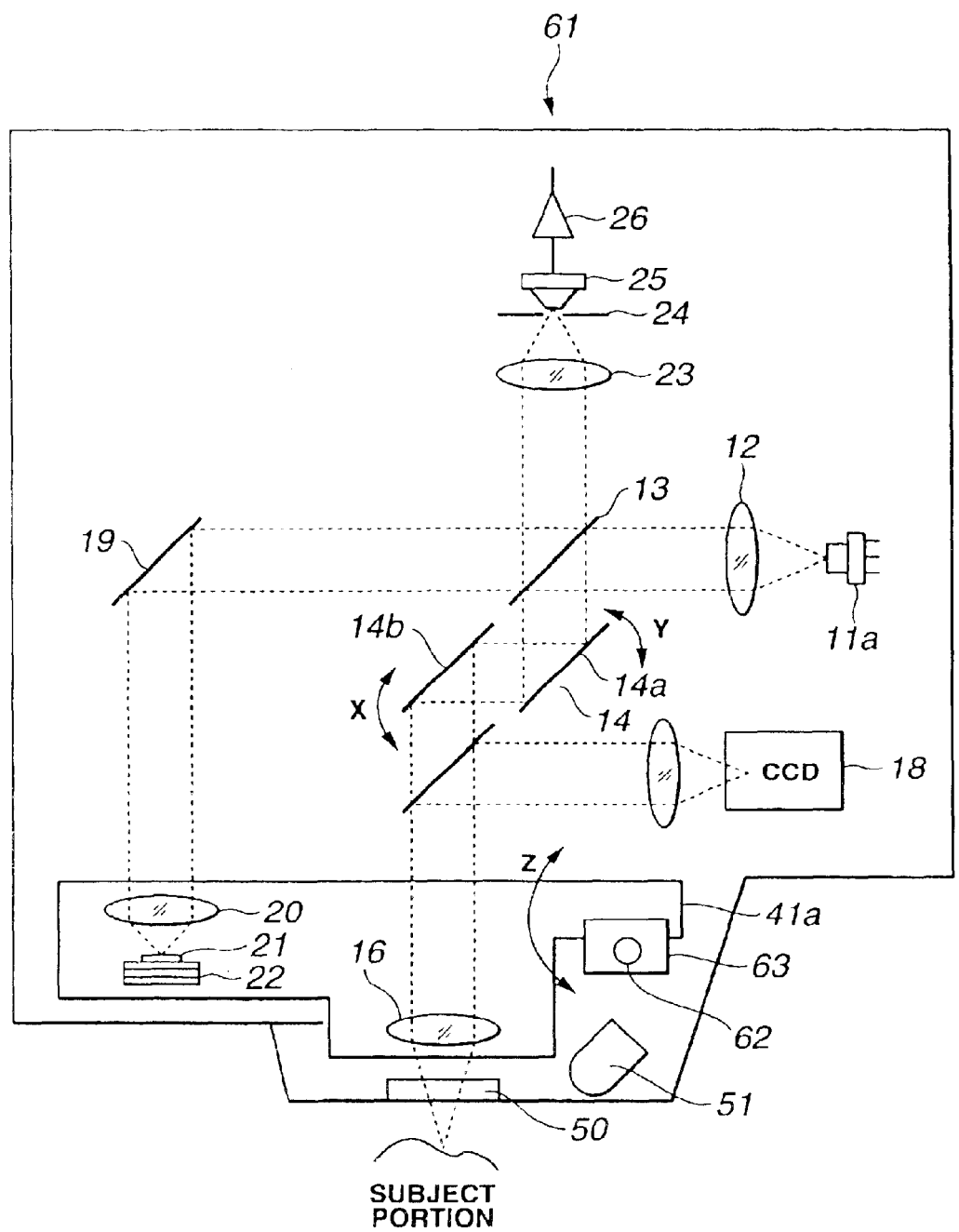
FIG. 6 is an explanatory diagram showing the internal structure of an optical probe and a main body of an optical imaging apparatus according to a second embodiment.
Figure 7A:
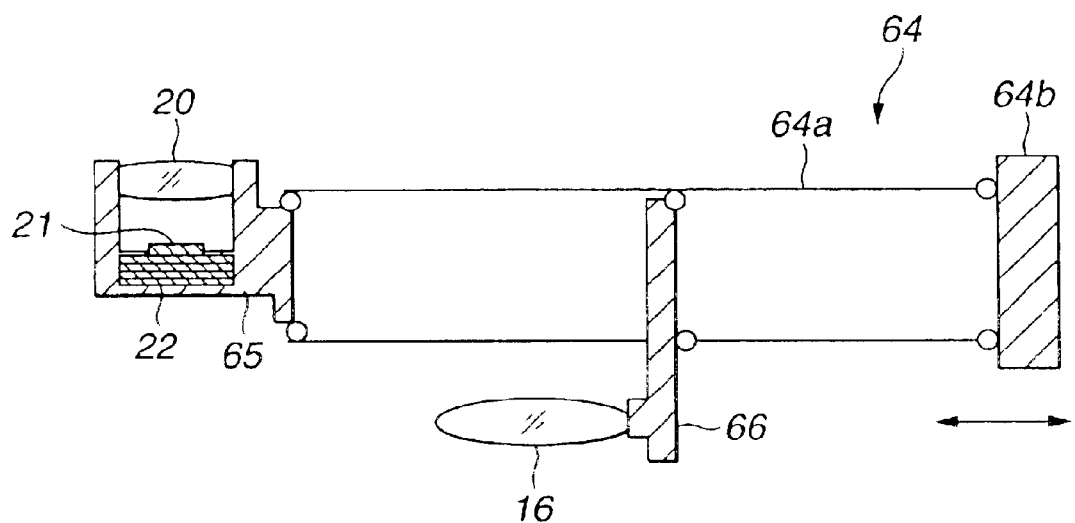
FIG. 7A is an explanatory diagram of a rotation driving unit and a horizontal holding unit when the rotation driving unit is not driven.
Figure 7B:
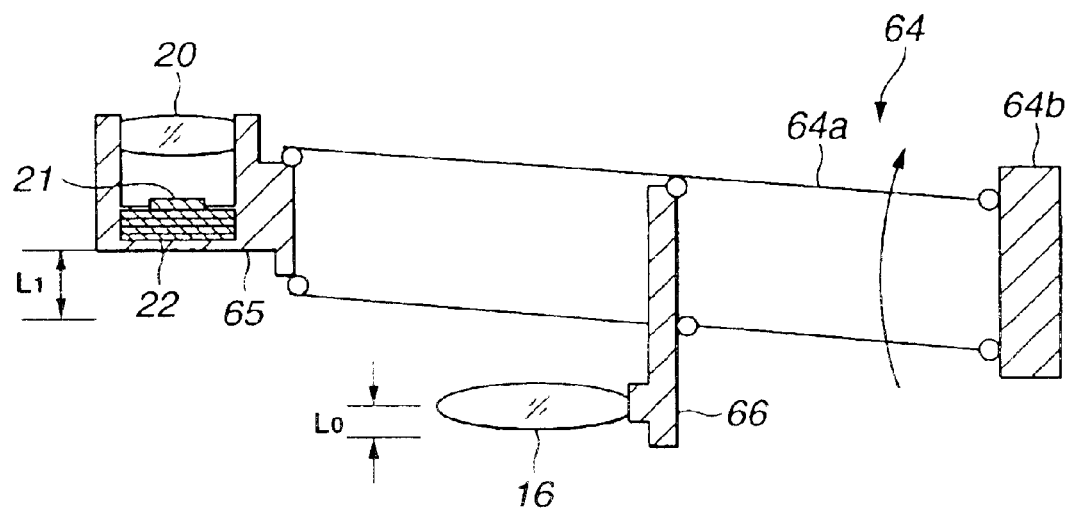
FIG. 7B is an explanatory diagram of the rotation driving unit and the horizontal holding unit when the rotation driving unit is changed from a state of FIG. 7A and is driven.

FIGS. 6 to 7B relate to the second embodiment, FIG. 6 is an explanatory diagram showing the internal structure of an optical probe and an apparatus main body according to the second embodiment, FIG. 7A is an explanatory diagram of an rotation driving unit and a horizontal holding unit when the rotation driving unit is not driven, and FIG. 7B is an explanatory diagram of the rotation driving unit and the horizontal holding unit when the rotation driving unit is changed from a state of FIG. 7A and is driven.

According to the first embodiment, as the optical path length interlockingly adjusting means, the modulating mirror 21 and the objective optical system 16 are integrally arranged to the optical path length interlockingly adjusting base 41a, together with the reflecting-side lens 20. An advancing and regressing driving unit 41b for advancing and regressing the optical path length interlockingly adjusting base 41a in the optical direction (Z axis direction) is arranged. However, according to the second embodiment, the rotation driving unit for rotating the optical path length interlockingly adjusting base 41a in the optical direction (Z axis direction) is arranged. Other structure is the same as that according to the first embodiment and a description thereof is omitted. The same components are designated by the same reference numerals.

That is, referring to FIG. 6, an optical probe 61 according to the second embodiment integrally includes the modulating mirror 21 and the objective optical system 16 as the optical path length interlockingly adjusting means, together with the reflecting-side lens 20, at the optical path length interlockingly adjusting base 41a. A rotation driving unit 63 is arranged to rotate the optical path length interlockingly adjusting base 41a in the optical axis (Z axis direction) around a rotatable rotation axis 62 as a central axis. Similarly to the case described according to the first embodiment, the rotation driving unit 63 is controlled and driven by the driving circuit 35 in the apparatus main body 3 via the signal line which is inserted into the connecting cable 5, synchronously with the coherent electronic signal which is outputted from the photo detector 25.

Referring to FIG. 7A, the optical path length interlockingly adjusting base 41a comprises a horizontal holding unit 64 in which two horizontal stick portions 64a are rotatably born to a fixing portion 64b. In the horizontal holding portion 64, the reflecting-side lens 20 and the fixing portion 64b of the modulating mirror 21 are rotatably born at the ends of the two horizontal stock portions 64a, and a fixing holding portion 66 of the objective optical system 16 is rotatably born at a predetermined position of the two stick portions 64a.

A positional relationship between a fixing holding portion 65 of the reflecting-side lens 20 and the modulating mirror 21 and the fixing holding portion 66 of the objective optical system 16 is set to have a predetermined ratio of a moving distance (the amount of movement). Further, according to the second embodiment, the predetermined ratio is set so that the moving distance (the amount of movement) of the fixing holding portion 65 of the reflecting-side lens 20 and the modulating mirror 21 is larger than that of the objective optical system 16.

When the rotational axis 62 is freely rotated by driving the rotation driving unit 63, referring to FIG. 7B, the two stick portions 64a of the horizontal holding unit 64 are rotated in the optical axis direction (Z direction), thereby rotating the fixing holding portion 66 of the objective optical system 16 and the fixing holding portion 65 of the reflecting-side lens 20 and the modulating mirror 21 in the optical axis direction (Z direction).

In this case, the fixing holding unit 66 of the objective optical system 16 and the fixing holding portion 65 of the reflecting-side lens 20 and the modulating mirror 21 are in the optical axis direction (Z direction) and, therefore, advance and regress in the optical axis direction (Z axis direction). A moving distance L1 of the reflecting-side lens 20 and the modulating mirror 21 in the optical axis (Z axis direction) is set to be larger than a moving distance L0 of the objective optical system 16 in the optical axis direction (z axis direction).

Herein, when scanning the subject portion further in the depth direction, an refractive index of the subject portion is higher than the refractive index of the air. Consequently, the focusing distance of the objective optical system 16 becomes longer. Thus, if the moving distance L0 of the objective optical system 16 in the optical axis (Z axis direction) and the moving distance L1 of the reflecting-side lens 20 and the modulating mirror 21 in the optical axis direction (Z axis direction) are set to have the same distance, the length of the optical path of the instrumentation light is longer than that of the reference light.

Therefore, the moving distance L1 of the reflecting-side lens 20 and the modulating mirror 21 in the optical axis direction (Z axis direction) must be larger than the moving distance L0 of the objective optical system 16 in the optical axis direction (Z axis direction) so that the length of the optical path of the instrumentation light matches that of the reference light according to the focusing distance depending on the difference of the refractive index.

According to the second embodiment, with the above-mentioned structure, the moving distance L1 of the reflecting-side lens 20 and the modulating mirror 21 in the optical axis direction (Z axis direction) is set to be larger than the moving distance L0 of the objective optical system 16 in the optical axis direction (Z axis direction) according to the focusing distance depending on the refractive index. Therefore, according to the second embodiment, the length of the optical path of the instrumentation light can substantially match that of the reference light.

As a result, according to the second embodiment, the same advantages as those of the first embodiment can be obtained and the image with high efficiency and high resolution can be obtained.

Third Embodiment

Figure 8:
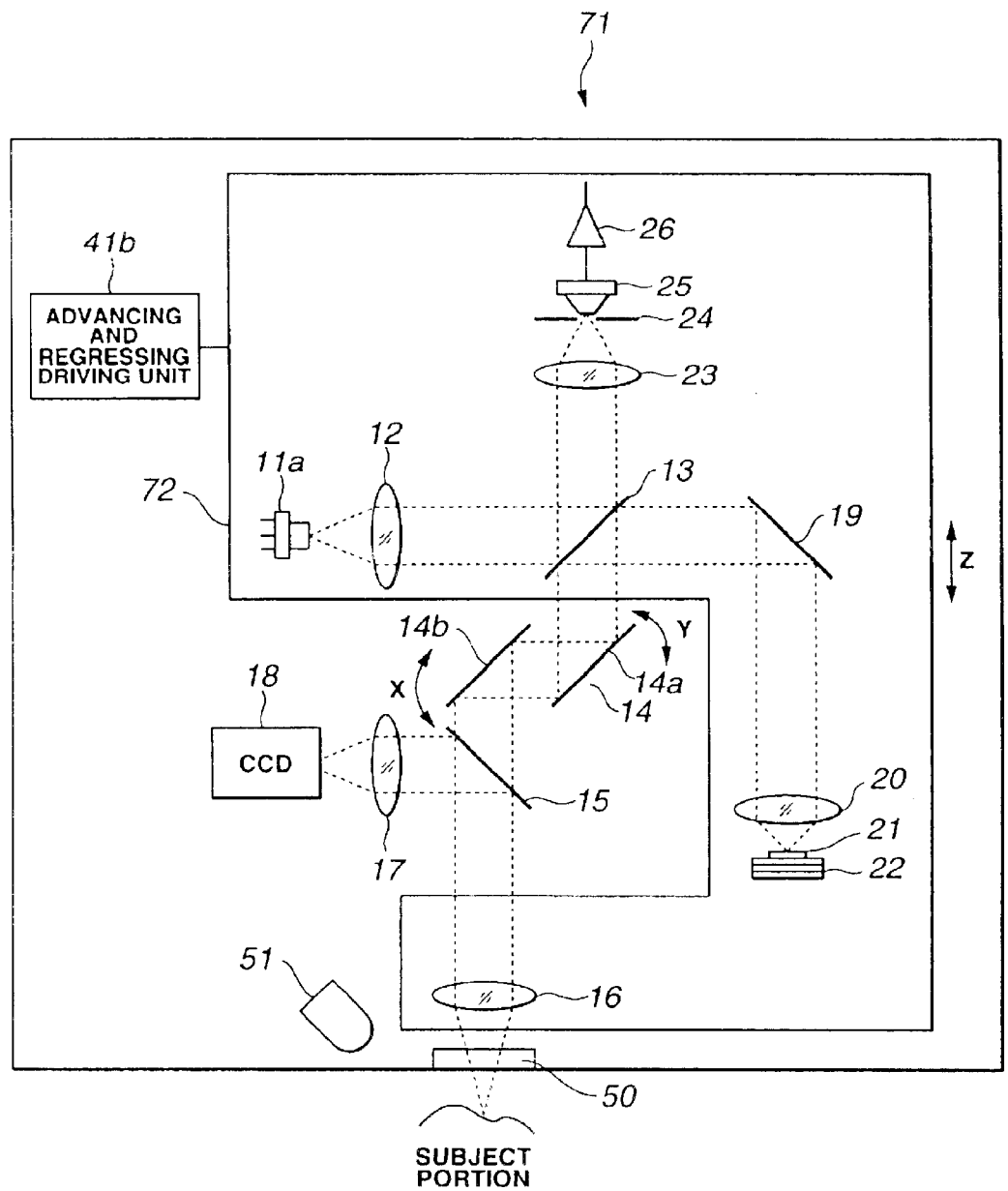
FIG. 8 is an explanatory diagram showing the internal structure of an optical probe according to a third embodiment.
Figure 9:
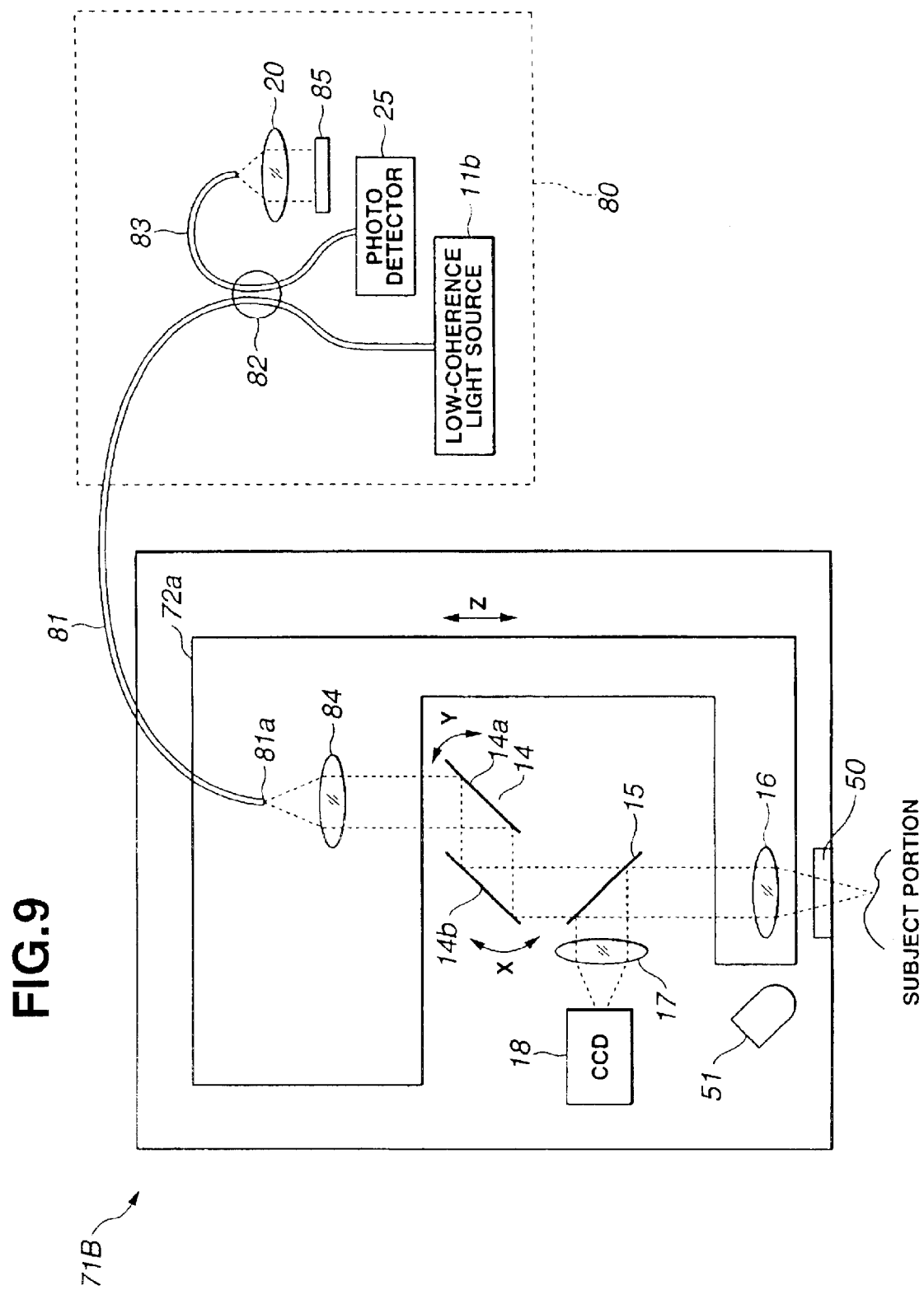
FIG. 9 is an explanatory diagram showing the internal structure of an optical probe and an optical tomogram signal detecting unit according to a modification of FIG. 8.

FIGS. 8 and 9 relate to the third embodiment of the present invention, FIG. 8 is an explanatory diagram showing the internal structure of an optical probe according to a third embodiment, and FIG. 9 is an explanatory diagram showing the internal structure of an optical probe and an optical tomogram signal detecting unit according to a modification of FIG. 8.

According to the first embodiment, the length of the optical path of the instrumentation light matches that of the reference light, and these lengths of the optical paths of the light are changed. However, according to the third embodiment, the subject portion is scanned by the objective optical system 16 in the optical axis direction (Z axis direction) without changing the lengths of the optical paths of the instrumentation light and the reference light. Other structure is the same as that of the first embodiment and a description thereof is omitted. Then, the same components are described with the same reference numerals.

That is, referring to FIG. 8, according to the third embodiment, an optical probe 71 integrally includes the irradiation window 50, the XY reflecting mirror scan 14, the wavelength separating mirror 15, and an optical system excluding the CCD-side lens 17 and the CCD 18 for surface observation, at a single optical path length interlockingly base 72a. An advancing and regressing driving unit 72b is arranged to advance and regress an optical path length interlockingly adjusting base 72a in the optical axis direction (Z axis direction).

Similarly to the case described according to the first embodiment, the advancing and regressing driving unit 72b is controlled and driven by the driving circuit 35 in the apparatus main body 3 via the signal line which is inserted into the connecting cable 5, synchronously with the coherent electronic signal outputted from the photo detector 25.

The advancing and regressing driving unit 72b is driven, thereby advancing and regressing the optical path length interlockingly adjusting base 72a in the optical axis direction (Z axis direction). Thus, the objective optical system 16 advances or regresses in the optical axis direction (Z axis direction) and, at the focus position of the objective optical system 16, the subject portion can be scanned in the depth direction thereof.

However, a distance from the half mirror 13 to the XY reflecting mirror scan 14 is reduced by a distance corresponding to a moving distance of the objective optical system 16 in the optical axis direction (Z axis direction). Therefore, the length of the optical path of the instrumentation light is not wholly changed. The entire optical system of the reference light is arranged to the optical path length interlockingly adjusting base 72a and, therefore, the length of the optical path of the reference light is not changed.

Hence, similarly to the first embodiment, the length of the optical path of the instrumentation light from the low-coherence light source 11a to the focus point condensed by the objective optical system 16 and from the focus point to the photo detector 25 can match the length of the optical path of the reference light from the low-coherence light source 11a to the light modulating mirror 21 and from the light modulating mirror 21 to the photo detector 25.

As a result, according to the third embodiment, the same advantages as those according to the first embodiment can be obtained.

Referring to FIG. 9, in the optical probe, the low-coherence light may be supplied by using the optical fiber.

As shown in FIG. 9, an optical probe 71B comprises an end surface 81a of an optical fiber 81 as light output means extending from an optical tomogram signal detecting unit 80, together with the objective optical system 16 at an optical path length interlockingly adjusting base 72a. Incidentally, the optical tomogram signal detecting unit 80 may be arranged in the apparatus main body 3 or may be arranged separately to the apparatus main body 3.

According to the present modification, the end surface 81a of the optical fiber 81, as the optical path length interlockingly adjusting means, advances and regresses in the optical axis direction together with the objective optical system 16.

The optical tomogram signal detecting unit 80 inputs the low-coherence light generated by the low-coherence light source 11b from a base end surface of the optical fiber 81, and transmits the light to the end surface 81a.

The optical fiber 81 is optically coupled to an optical fiber 83 with an optical coupler 82 in the halfway. Therefore, the low-coherence light generated by the low-coherence light source 11b is divided into the instrumentation light and the reference light at the optical coupler 82.

The instrumentation light supplied from the end surface 81a of the optical fiber 81 is made parallel by the light source lens 84 in the optical probe 71B, is scanned in the horizontal direction by the XY reflecting mirror scan 14, and is transmitted to the objective optical system 16 via the wavelength separating mirror 15. The instrumentation light is condensed to the subject portion at the focus point of the objective optical system 16. The reflection light and scattering light of the subject portion from the focus point pass through the same optical path as that of the irradiation light. Only the instrumentation light having the same wavelength as that of the irradiation light passes by using the wavelength separating mirror 15 and returns to the optical fiber 81 again. Incidentally, light having the wavelength other than the instrumentation light reflected by the wavelength separating mirror 15 is condensed by the CCD-side lens 17, and is received by the light receiving surface of the CCD 18 for surface observation. Then, the image is picked up.

The instrumentation light returned to the optical fiber 81 is transmitted to the optical fiber 81, and is incident on the optical coupler 82.

The reference light divided by the optical coupler 82 is transmitted to optical fiber 83, and is reflected by the reflecting mirror 85 via the reflecting-side lens 20 from the end surface of the optical fiber 83. The reflected reference light is transmitted to the optical fiber 83 again and is incident on the optical coupler 82 similarly to the instrumentation light. The reference light and the instrumentation light are made coherent at the optical coupler 82 and the coherent light is received by the photo detector 25.

According to the present modification, the end surface 81a of the optical fiber 81 as the light output means, the light-source-side lens 84, and the objective optical system 16 are integrally arranged to the optical path length interlockingly adjusting base 72a. The optical path length interlockingly adjusting base 72a advances and regresses in the optical axis direction (Z axis direction) by driving the advancing and regressing driving unit 72b, thereby advancing and regressing the objective optical system 16 in the optical axis direction (Z axis direction). Thus, the subject portion can be scanned at the focus point of the objective optical system 16 in the depth direction thereof.

Herein, the distance from the light-source-side lens 84 to the XY reflecting mirror scan 14 is reduced by a distance corresponding to the moving distance of the objective optical system 16 in the optical axis direction (z axis direction) and, therefore, the length of the optical path of the instrumentation light is not wholly changed. The length of the optical path of the reference light is not changed because the entire optical system of the reference light is arranged to the optical tomogram signal detecting unit 80. As a result, according to the modification, in addition to the same advantages as those according to the third embodiment, the optical system in the optical probe can be reduced in size.

Fourth Embodiment

Figure 10:
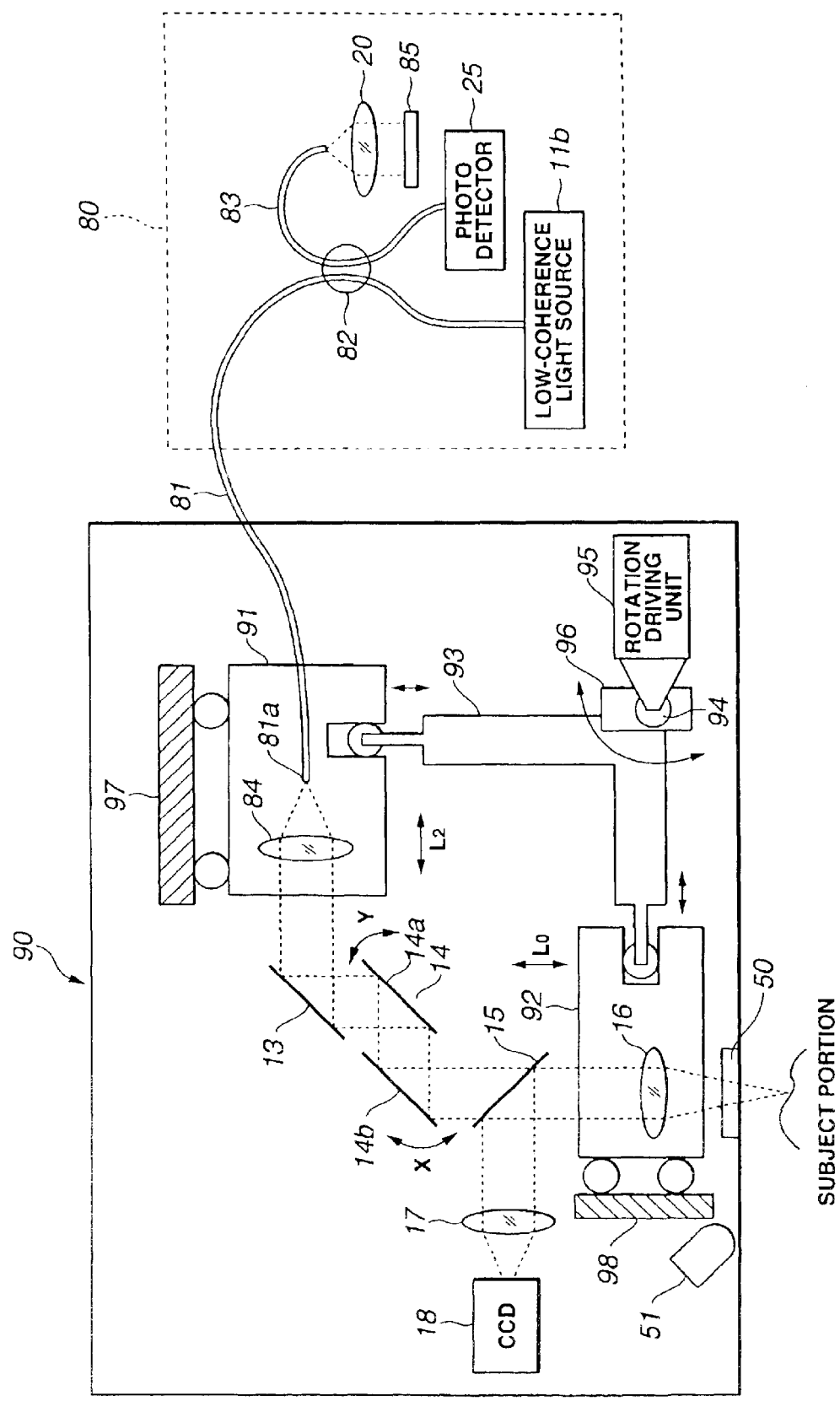
FIG. 10 is an explanatory diagram showing the internal structure of an optical probe and an optical tomogram signal detecting unit according to a fourth embodiment of the present invention.

FIG. 10 is an explanatory diagram showing the internal structure of an optical probe and an optical tomogram signal detecting unit according to a fourth embodiment of the present invention.

As compared with the modification of the third embodiment, according to the fourth embodiment, in place of the advancing and regressing driving unit 72b, a rotation driving unit is arranged and a position adjusting unit is provided for the rotation driving unit. Other structure is the same as that according to the modification of the third embodiment and, therefore, a description thereof is omitted. Then, the same components are described with the same reference numerals.

Referring to FIG. 10, according to the fourth embodiment, an optical probe 90 comprises the end surface 81a of the optical fiber 81 as the light output means and the light-source-side lens 84 at a light-source-side adjusting base 91, and the objective optical system 16 at an objective-side adjusting base 92. The light-source-side adjusting base 91 and the objective-side adjusting base 92 are rotatably born at the end of an L-shaped portion 93. A base end side of the L-shaped portion 93 is rotatably born to a rotation driving unit 95 with a rotation axis as central axis.

The end sides of the L-shaped portion 93 can be stretched in the axial direction, and can set the length in the axial direction by the position adjusting unit 96.

That is, according to the fourth embodiment, as described according to the second embodiment, the moving distance of the end surface 81a of the optical fiber 81 and the light-source-side lens 84 in the optical axis is set to be larger than the moving distance of the objective optical system 16 in the optical axis direction (Z axis direction) so that the length of the optical path of the instrumentation light matches that of the reference light. Incidentally, reference numerals 97 and 98 denote restraining units for restraining the direction of the light source adjusting base 91 and the objective-side adjusting base 92 in the optical axis direction in accordance with the L-shaped rotation. Rollers are provided for the restraining units 97 and 98.

In the optical probe 90 with the above-mentioned structure, the light-source-side adjusting base 91 is rotated in the optical axis direction by freely rotating the rotational axis 94 using the driving of the rotation driving unit 95. Simultaneously, the objective-side adjusting base 92 is rotated in the optical axis direction (Z axis direction).

In this case, the end portions of the L-shaped portion 93 are stretched by using the position adjusting unit 96 so that the moving distance of the light-source-wide adjusting base 91 in the optical axis direction is larger than that of the objective-side adjusting base 92 in the optical axis direction (Z axis direction) for purpose of the matching of the lengths of the optical paths of the instrumentation light and the reference light. The restraining units 97 and 98 restrain the directions to the optical axis ones of the light-source-side adjusting base 91 and the objective-side adjusting base 92. The light-source-side adjusting base 91 is directed in the optical axis direction and is advanced and regressed in the optical axis direction. The objective-side adjusting base 92 is also in the optical axis direction (Z axis direction) and is advanced and regressed in the optical axis direction (Z axis direction).

Herein, according to the fourth embodiment, a moving distance L2 of the light-source-side adjusting base 91 in the optical axis direction is set to be larger than the moving distance L0 of the objective-side adjusting base 92 in the optical axis direction (Z axis direction). That is, according to the fourth embodiment, the moving distance L2 of the end surface 81a of the optical fiber 81 as the light output means and the light-source-side lens 84 in the optical axis direction is set to be larger than the moving distance L0 of the objective-side optical system 16 in the optical axis direction (Z axis direction).

Therefore, according to the fourth embodiment, as described according to the second embodiment, the length of the optical path of the instrumentation light can match that of the reference light in accordance with the focusing distance depending on the difference of the refractive index.

Figure 11:
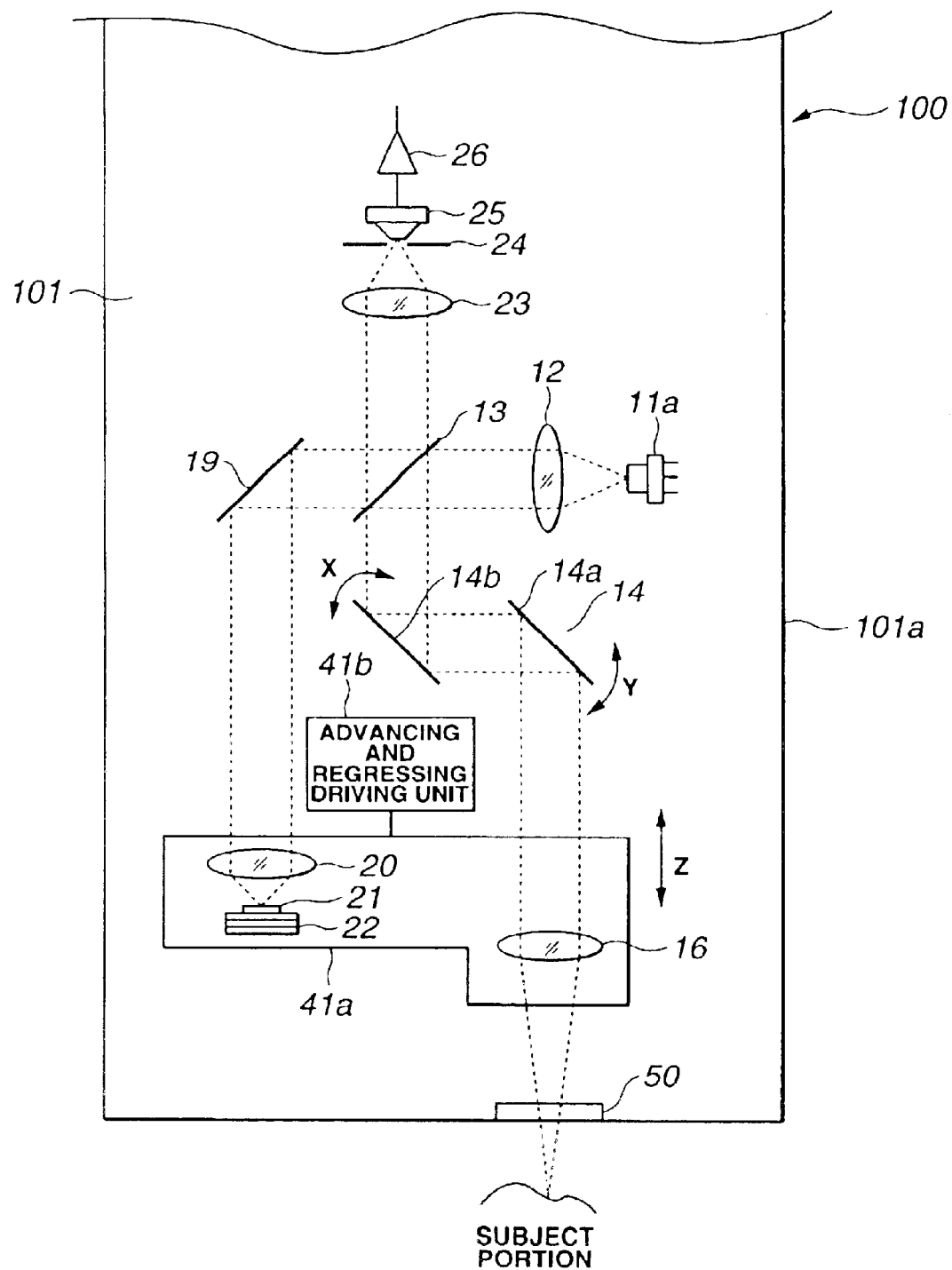
FIG. 11 is an explanatory diagram of an endoscope in which an optical system in FIG. 2 is arranged to an insertion portion tip.

Further, the above-mentioned optical imaging apparatus may have the optical system in the optical probe in the endoscope. FIG. 11 is an explanatory diagram of the endoscope in which the optical system in the optical probe is arranged at the insertion end tip.

Referring to FIG. 11, an endoscope 100 comprises an optical system 101 at an insertion portion tip 101a thereof. Although the optical system 101 is the same as that according to the first embodiment, the present invention is not limited to this. The optical system similar to that according to the second to fourth embodiments may be arranged to the insertion portion tip 101a of the endoscope 100.

Figure 12:
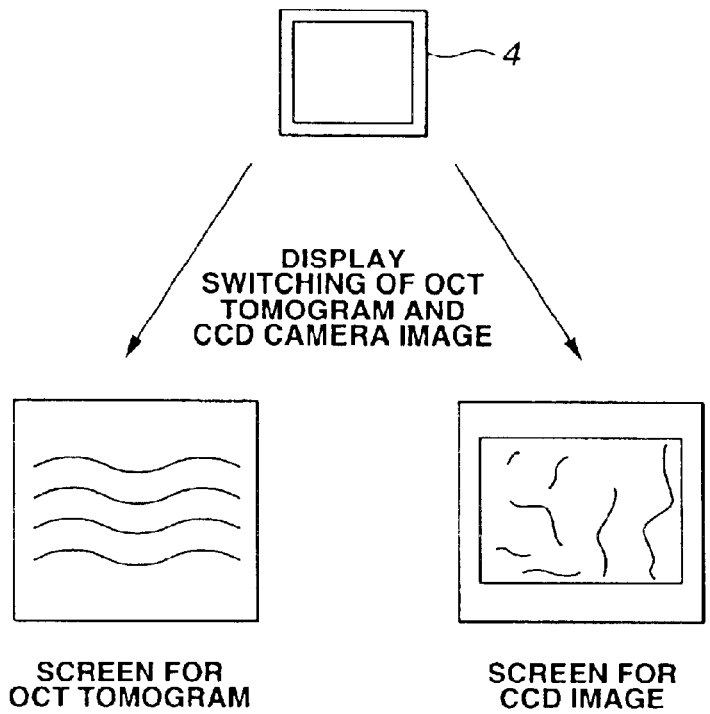
FIG. 12 is an explanatory diagram when a three-dimensional tomogram (OCT tomogram) and an image for surface observation (CCD image) are switched and displayed on a display screen of a monitor.
Figure 14:
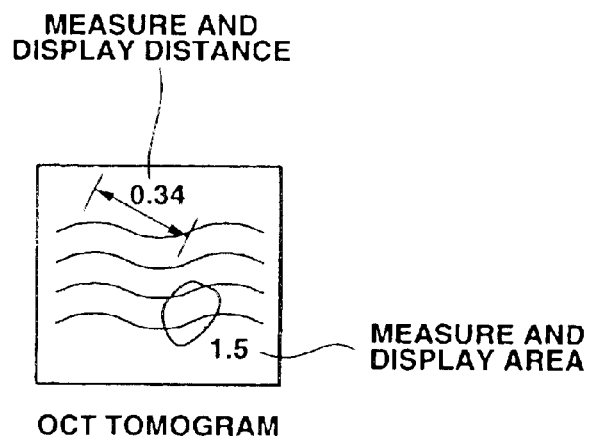
FIG. 14 is a diagram showing a display example of the OCT tomogram.

Referring to FIGS. 12 to 14, the three-dimensional tomogram (OCT tomogram) and the image for surface observation (CCD image) which are obtained by the optical imaging apparatus may be switched and displayed on the display surface of the monitor 4.

Figure 13A:
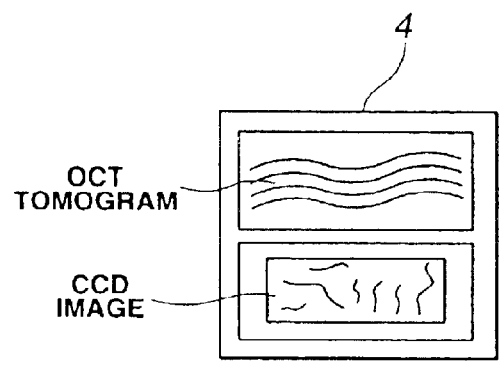
FIG. 13A is a diagram showing a display example of the OCT tomogram and the CCD image.
Figure 13B:
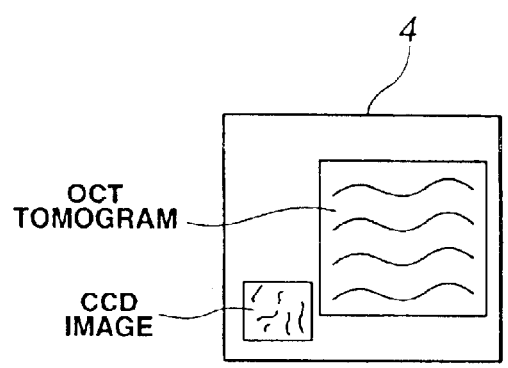
FIG. 13B is a diagram showing a display example of an enlargedly displayed OCT tomogram and a reduced and displayed CCD image in FIG. 13A.
Figure 13C:
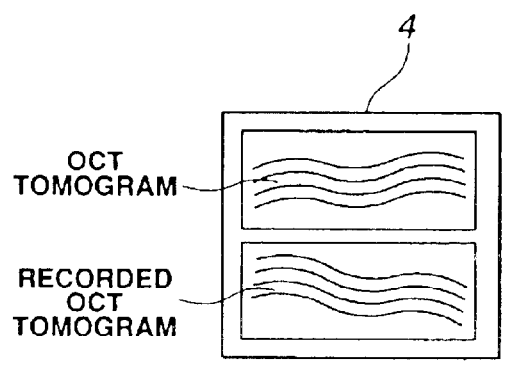
FIG. 13C is a diagram showing a display example of the OCT tomogram and a recorded OCT tomogram.
Figure 13D:
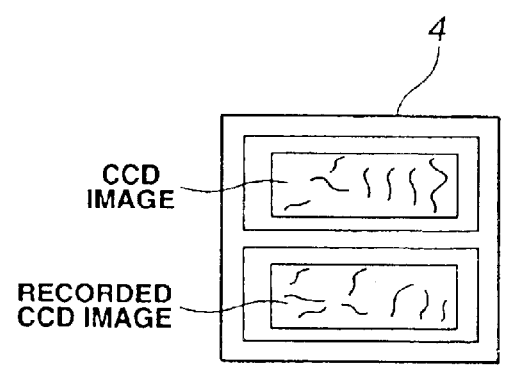
FIG. 13D is a diagram showing a display example of the CCD image and a recorded CCD image.

FIG. 12 is an explanatory diagram when a three-dimensional tomogram (OCT tomogram) and the image for surface observation (CCD image) are switched and displayed on a display screen of a monitor, FIG. 13A is a diagram showing a display example of the OCT tomogram and the CCD image, FIG. 13B is a diagram showing a display example of an enlargedly displayed OCT tomogram and a reduced and displayed CCD image in FIG. 13A, FIG. 13C is a diagram showing a display example of the OCT tomogram and a recorded OCT tomogram, FIG. 13D is a diagram showing a display example of the CCD image and a recorded CCD image and, FIG. 14 is a diagram showing a display example of the OCT tomogram.

Referring to FIG. 12, the three-dimensional tomogram (OCT tomogram) and the image for surface observation (CCD image) which are obtained by the optical imaging apparatus are switched and displayed on the display surface of the monitor 4.

Referring to FIG. 13A, the OCT tomogram and the CCD image may be displayed on the display surface of the monitor 4 with the same size. Referring to FIG. 13B, the OCT tomogram may enlargedly be displayed and the CCD image may be displayed with the small size.

Referring to FIGS. 13C and 13D, the currently-obtained image and the recorded image may be displayed simultaneously, be compared, or be searched.

Referring to FIG. 13C, the obtained OCT tomogram and the recorded OCT may be displayed on the display surface of the monitor 4 with the same size. Referring to FIG. 13D, the obtained CCD image and the recorded CCD image may be displayed on the display surface of the monitor 4 with the same size.

Referring to FIG. 14, in the OCT tomogram, the distance to a specified portion of the subject portion can be measured and displayed, and the area can be measured and displayed.

Fifth Embodiment

Figure 15:
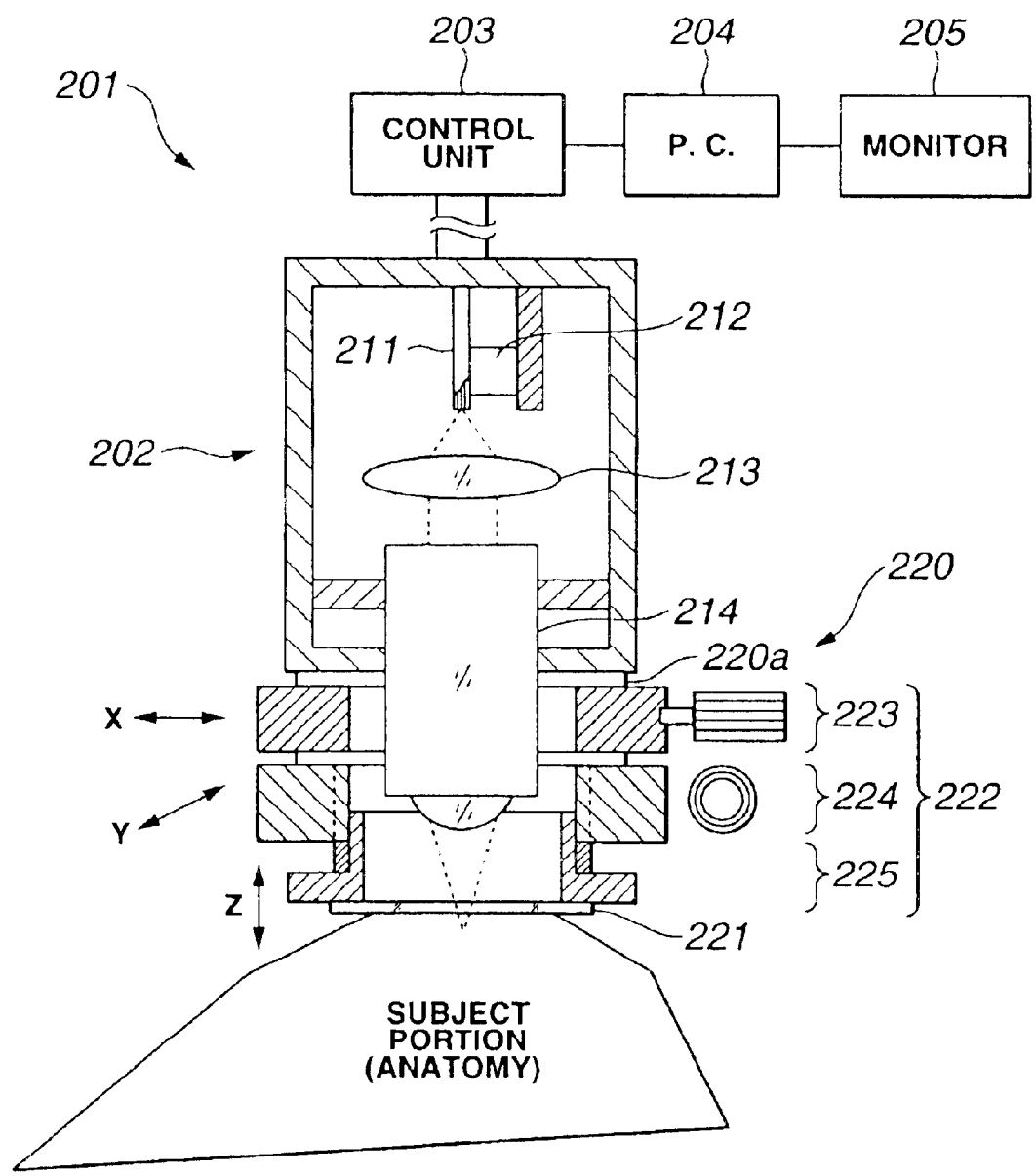
FIG. 15 is a diagram showing the entire structure of an optical imaging apparatus according to a fifth embodiment of the present invention.
Figure 16:
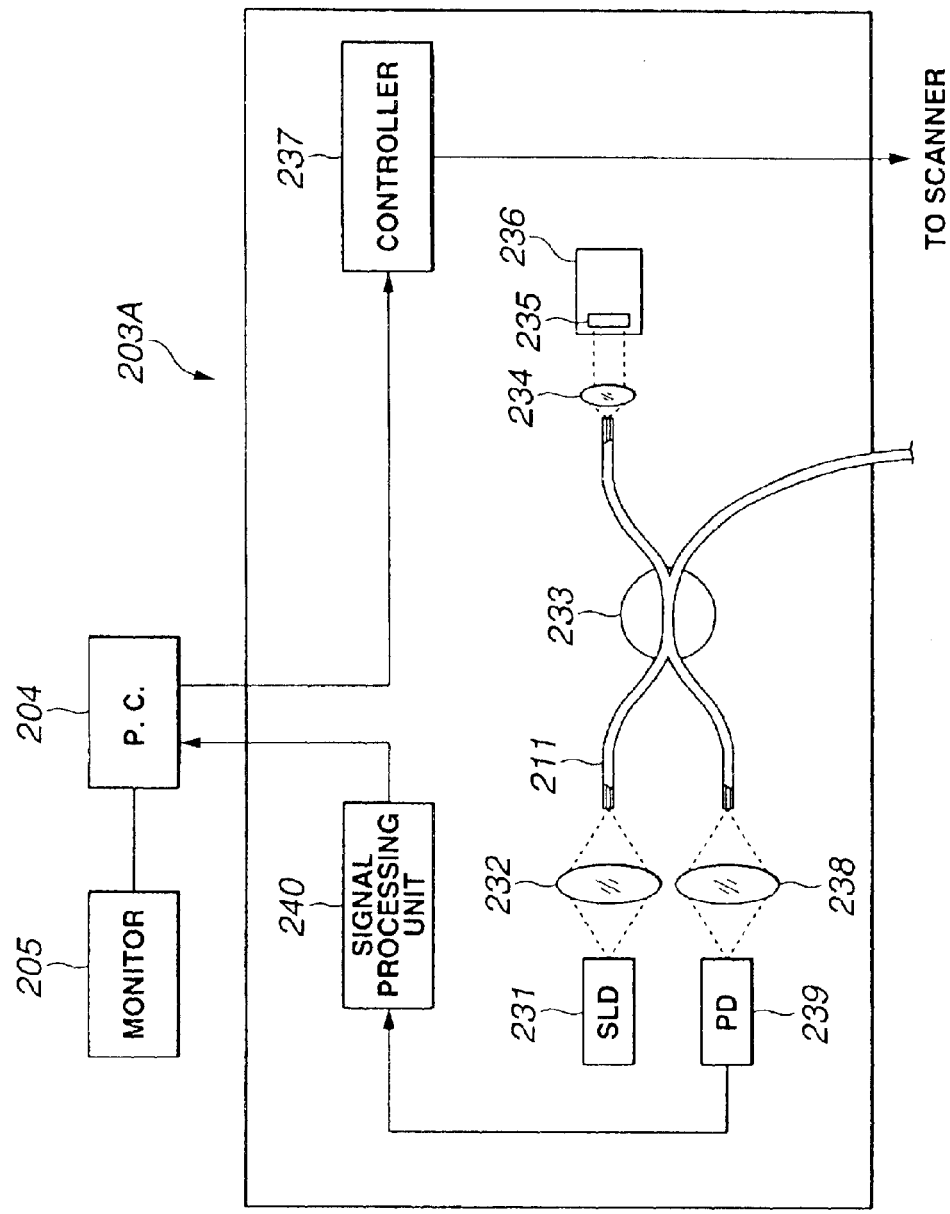
FIG. 16 is a schematic diagram showing the structure of a low-coherence unit.
Figure 17:
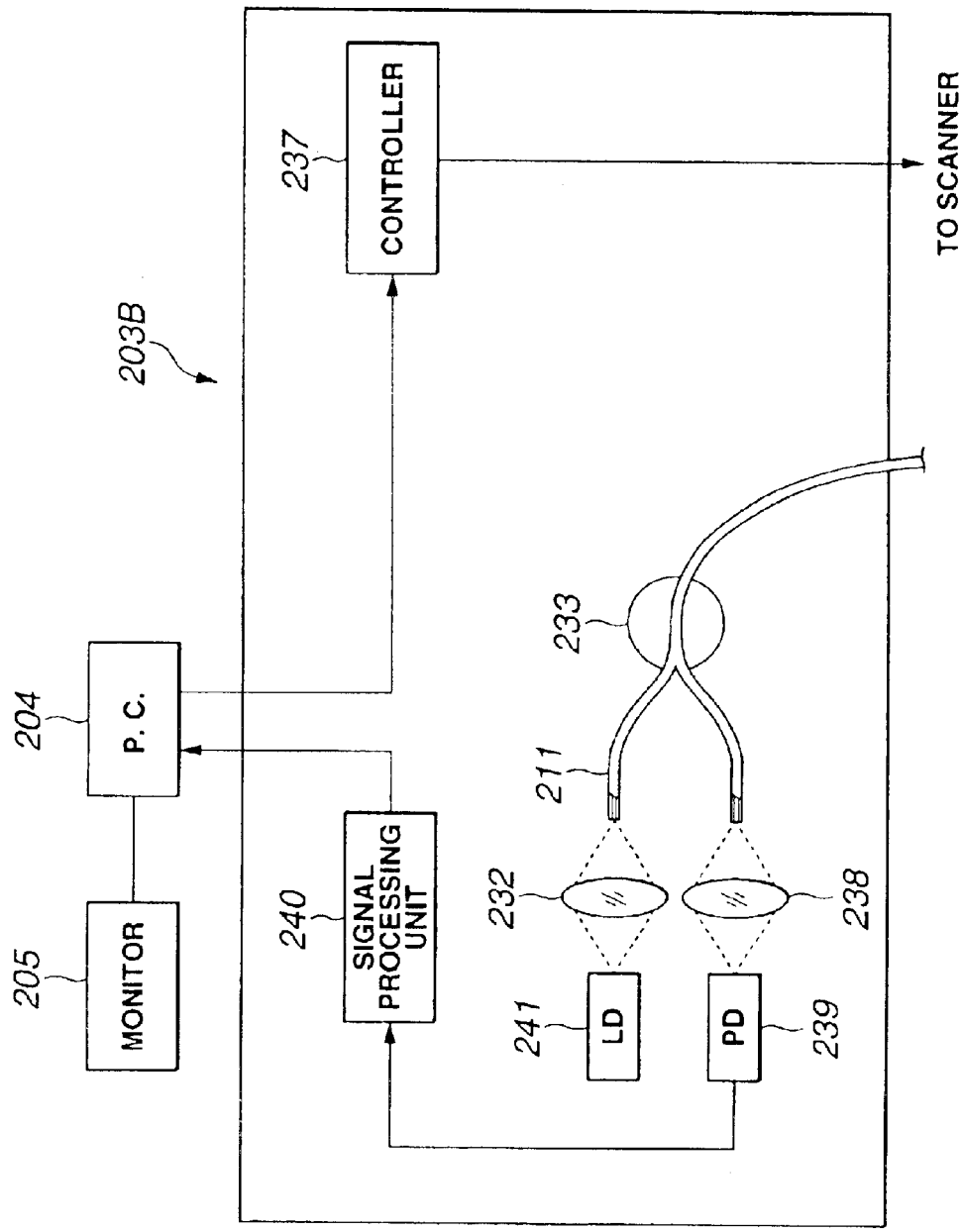
FIG. 17 is a schematic diagram showing the structure of a conjugate focus-point unit.
Figure 18:
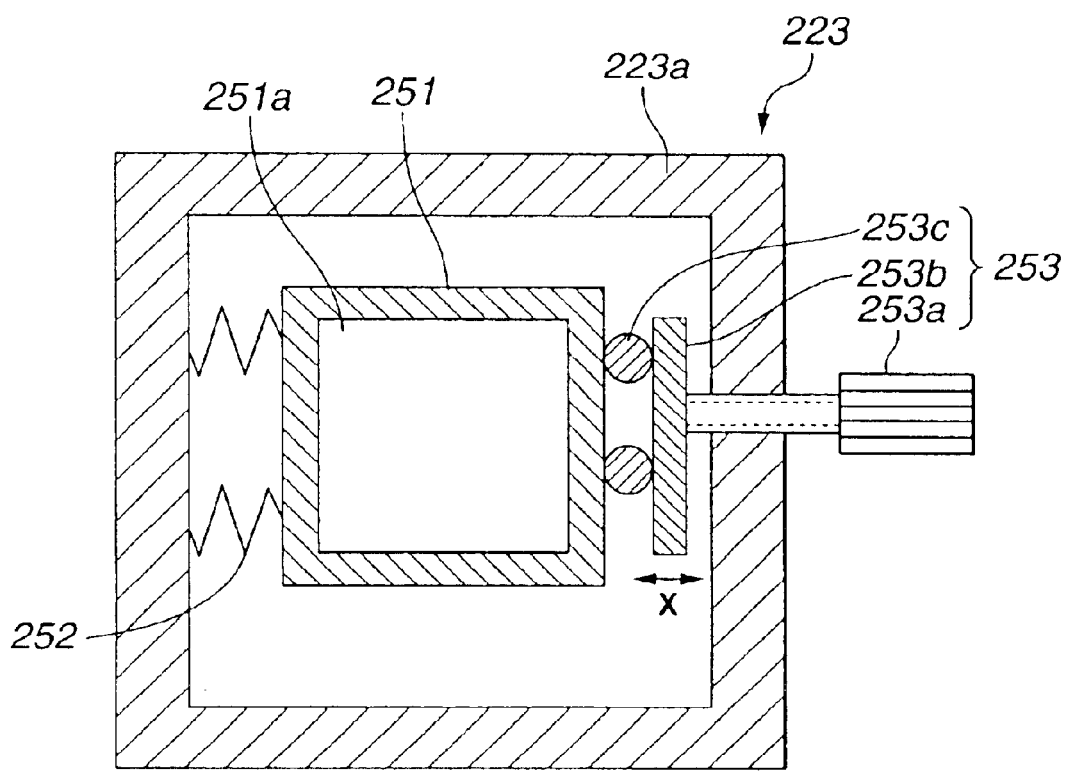
FIG. 18 is a laterally cross-sectional view showing an X stage of a mechanism for adjusting the position in a field of view in FIG. 15.
Figure 19:
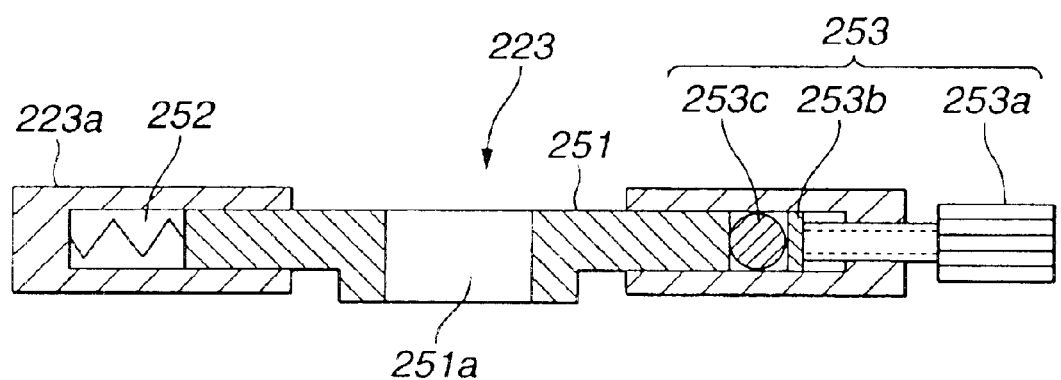
FIG. 19 is a longitudinally cross-sectional view showing the X stage of the mechanism for adjusting the position in the field of view in FIG. 15.
Figure 20:
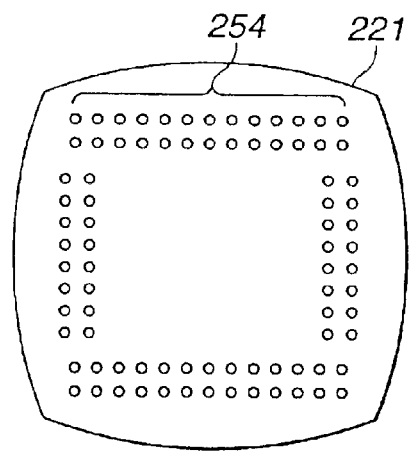
FIG. 20 is an explanatory diagram showing a surface side of a subject portion of a cover glass.
Figure 21:
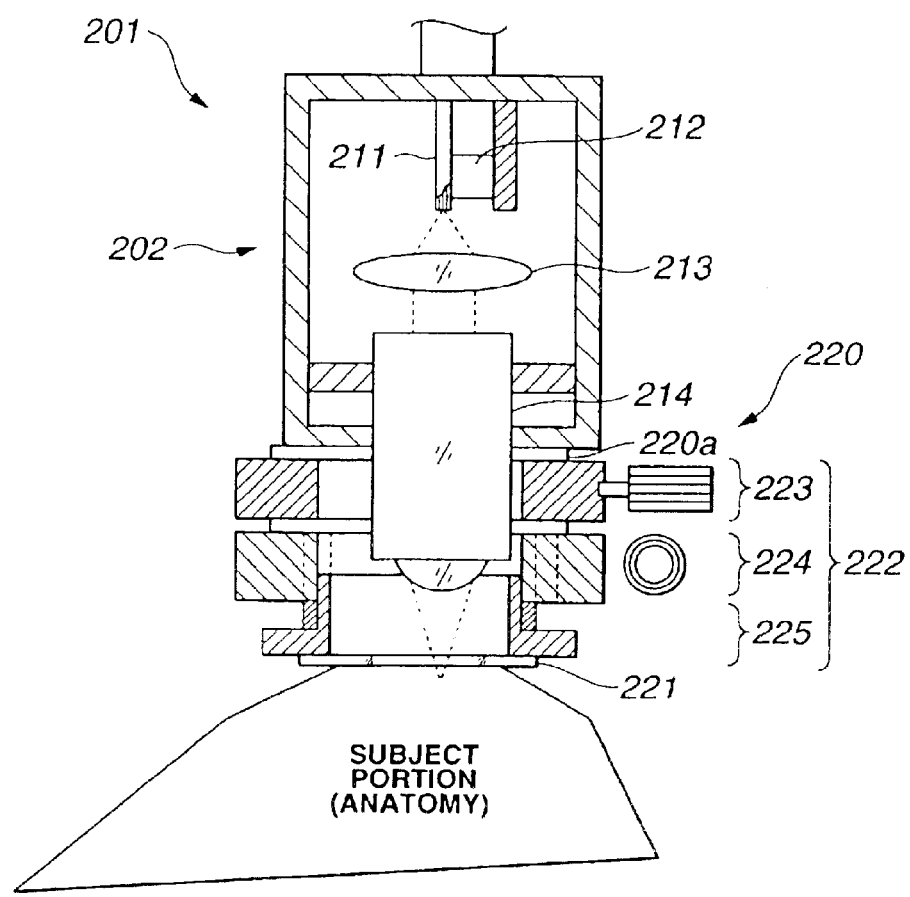
FIG. 21 is an explanatory diagram showing an optical probe when an objective optical system is located in the right direction of the anatomy of the subject portion.
Figure 22:
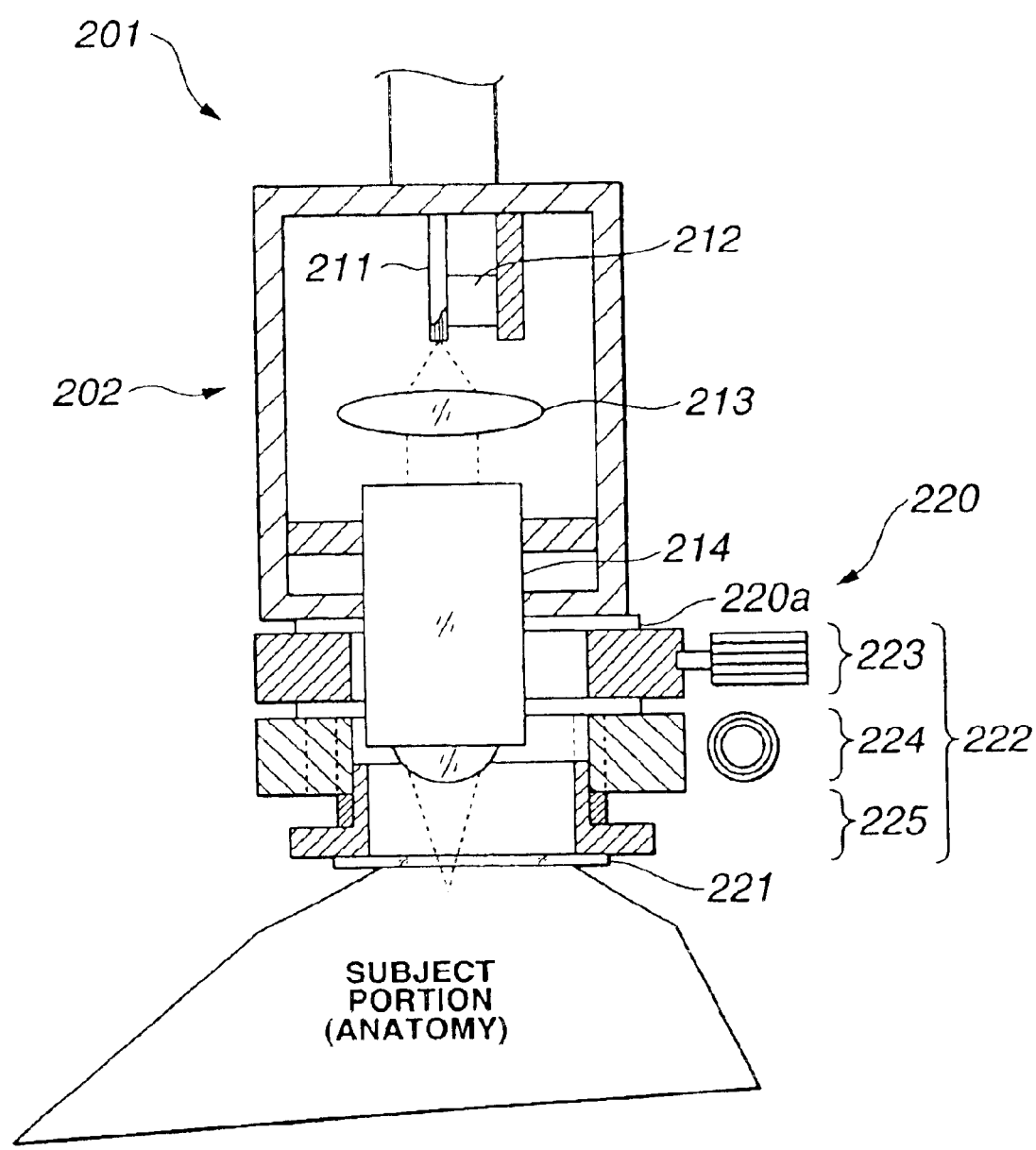
FIG. 22 is an explanatory diagram showing the optical probe when a positioning unit is moved in the right direction of the objective optical system from a state in FIG. 21.
Figure 23:
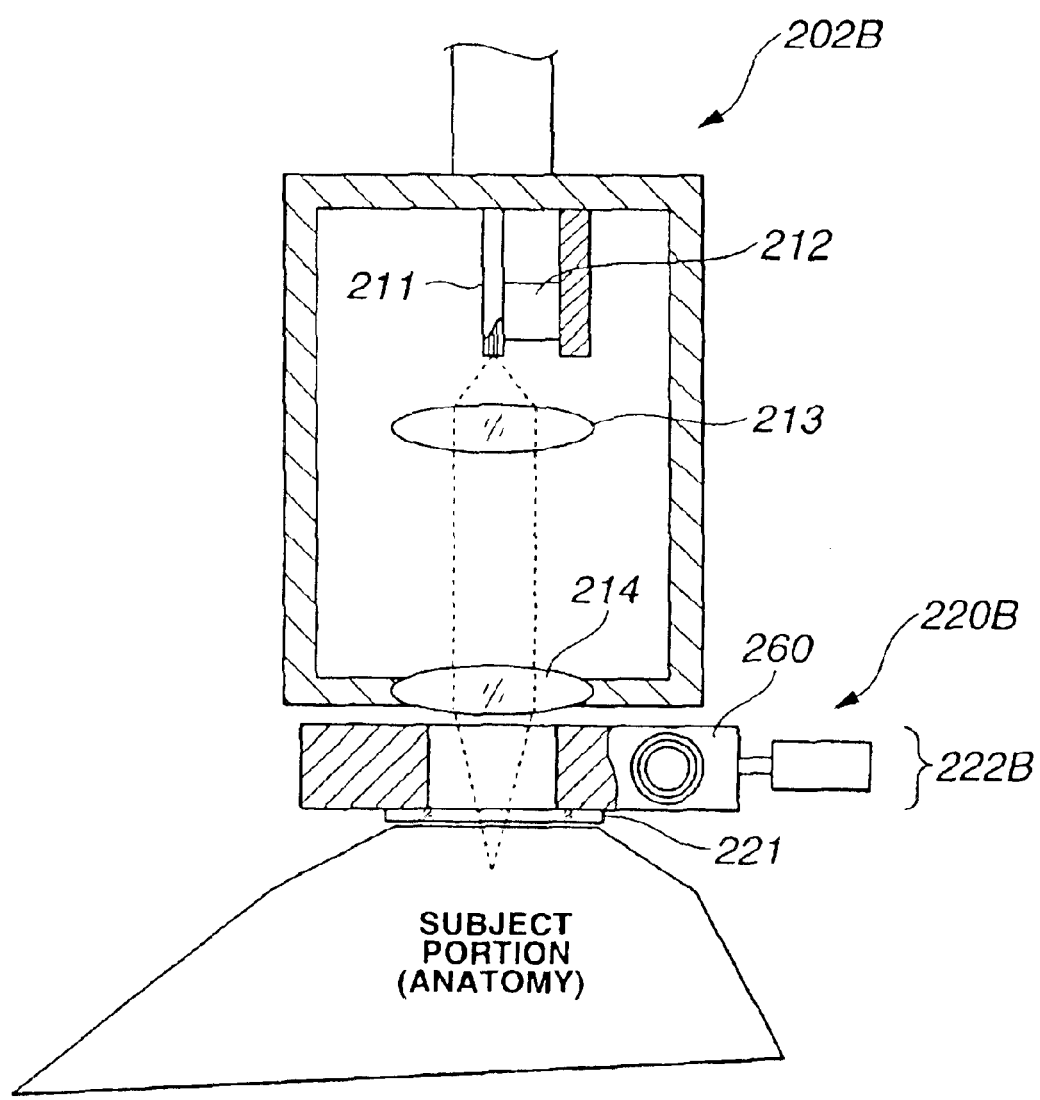
FIG. 23 is an explanatory diagram showing an optical probe according to the first modification.
Figure 24:
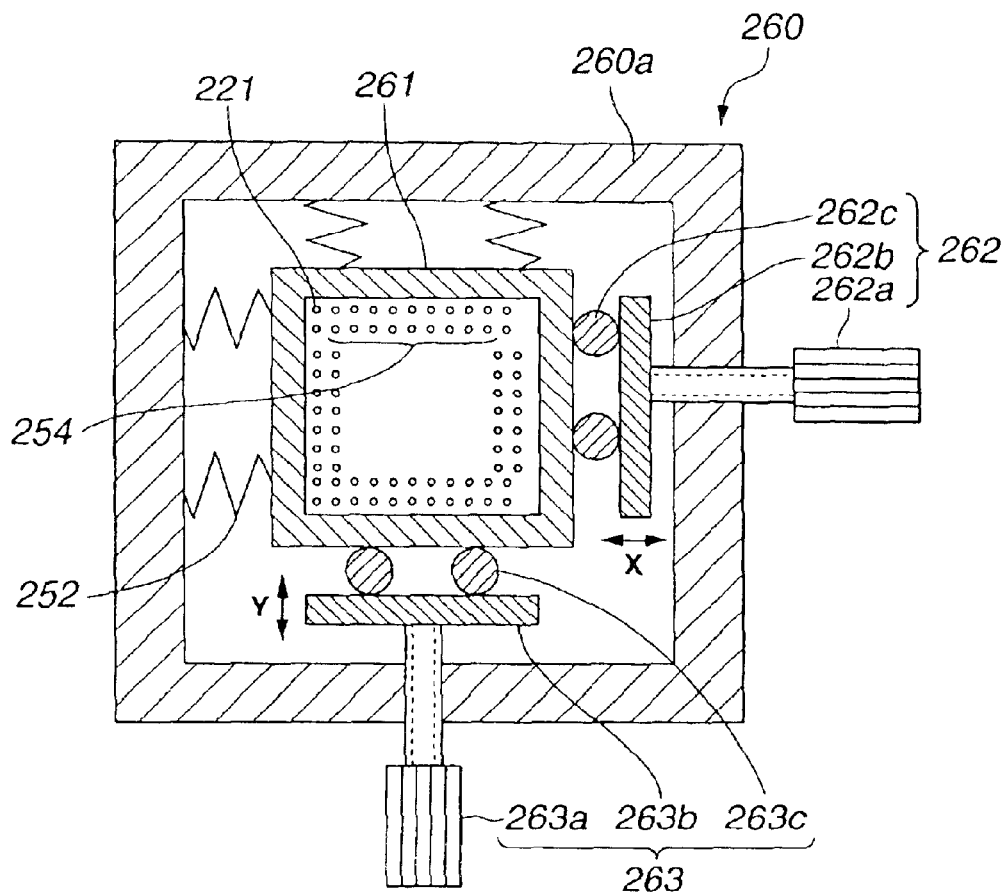
FIG. 24 is a laterally cross-sectional view showing the XY stage of the mechanism for adjusting the position in the field of view in FIG. 23.
Figure 25:
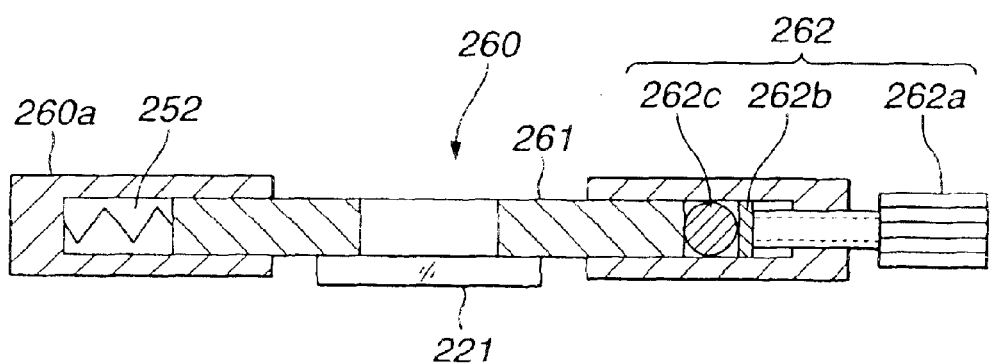
FIG. 25 is a longitudinally cross-sectional view showing the XY stage of the mechanism for adjusting the position in the field of view in FIG. 23.
Figure 26:
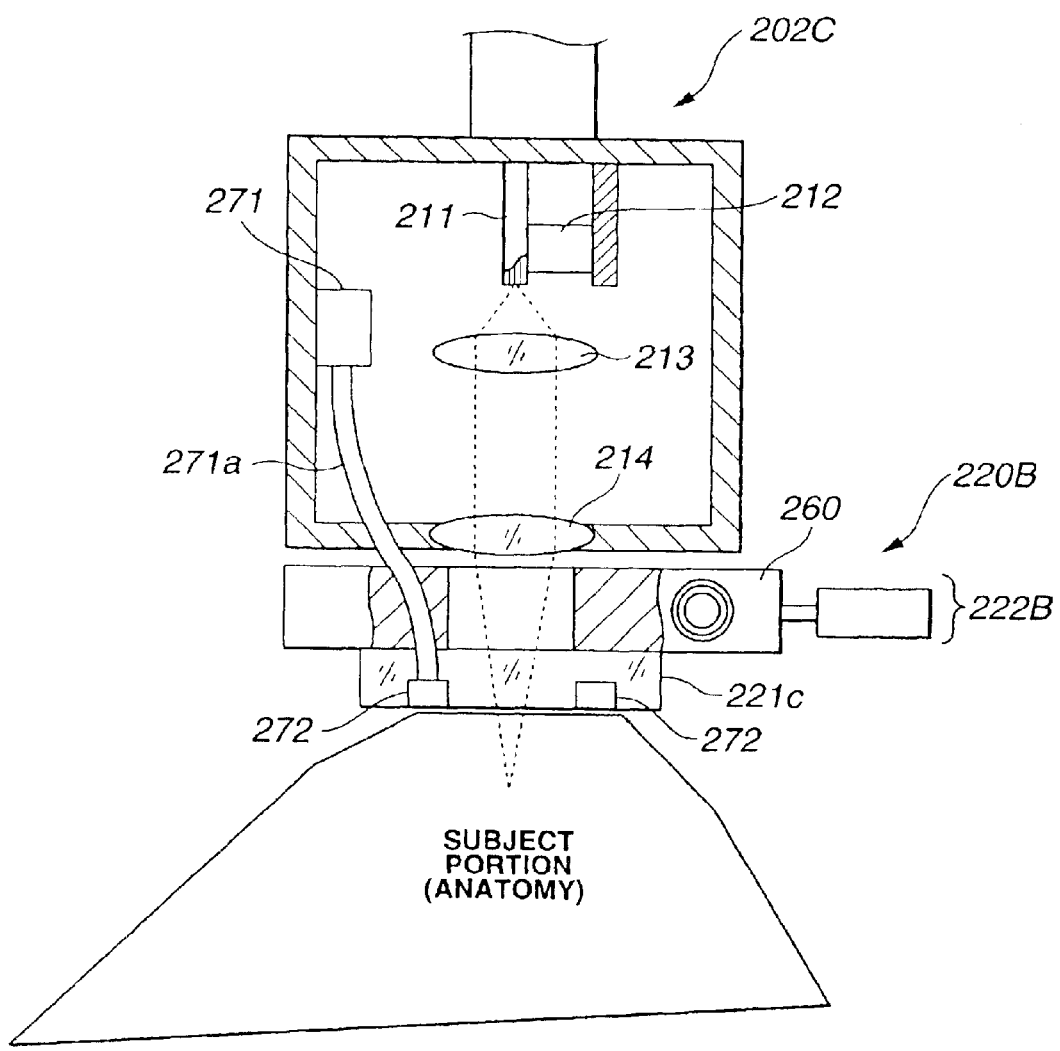
FIG. 26 is an explanatory diagram showing the optical probe according to the second modification.
Figure 27:
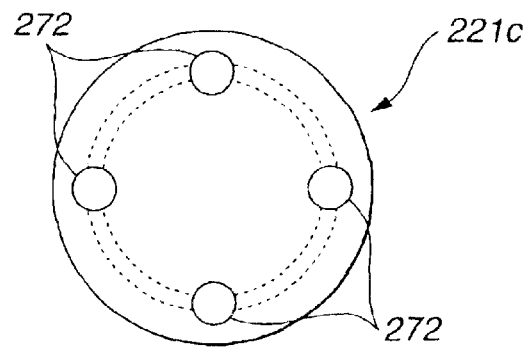
FIG. 27 is an explanatory diagram showing a surface side of the subject portion of a cover glass in FIG. 26.

FIGS. 15 to 27 relate to a fifth embodiment of the present invention, FIG. 15 is a diagram of the entire structure showing an optical imaging apparatus according to the fifth embodiment of the present invention, FIG. 16 is a schematic diagram showing the structure of a low-coherence unit, FIG. 17 is a schematic diagram showing the structure of a conjugate focus-point unit, FIG. 18 is a laterally cross-sectional view showing an X stage of a mechanism for adjusting the position in a field of view in FIG. 15, FIG. 19 is a longitudinally cross-sectional view showing the X stage of the mechanism for adjusting the position in the field of view in FIG. 15, FIG. 20 is an explanatory diagram showing a surface side of a subject portion of a cover glass, FIG. 21 is an explanatory diagram showing an optical probe when an objective optical system is located in the right direction of the anatomy of the subject portion, FIG. 22 is an explanatory diagram showing the optical probe when a positioning unit is moved in the right direction of the objective optical system from a state in FIG. 21, FIG. 23 is an explanatory diagram showing an optical probe according to a first modification, FIG. 24 is a laterally cross-sectional view showing the XY stage of the mechanism for adjusting the position in the field of view in FIG. 23, FIG. 25 is a longitudinally cross-sectional view showing the XY stage of the mechanism for adjusting the position in the field of view in FIG. 23, FIG. 26 is an explanatory diagram showing the optical probe according to a second modification, and FIG. 27 is an explanatory diagram showing a surface side of the subject portion of a cover glass in FIG. 26.

Referring to FIG. 15, an optical imaging apparatus 201 according to the fifth embodiment of the present invention comprises an optical scanning probe (hereinafter, simply abbreviated to an optical probe) 202 for scanning the subject portion with observation light as beams supplied from a light source and transmitting return light from the subject portion by scanning, a control unit 203 for controlling and driving the optical probe 202, a P.C. (computer) 204 for forming the tomogram of the subject portion by controlling the control unit 203, and a monitor 205, as display means, for displaying the tomogram obtained by the P.C. 204. Incidentally, according to the fifth embodiment, the optical probe 202 is a hand-held probe obtained by forming the probe itself of a grippable casing.

According to the fifth embodiment, the optical imaging apparatus 201 comprises an observation device in which the control unit 203, the P.C. 204, and the monitor 205 are connected to the optical probe 202. The return light from the subject portion by optically scanning the optical probe 202 is captured and is guided to the observation device. Then, the light is imaged by the observation device and the tomogram is obtained by optically scanning.

The control unit 203 comprises a fiber 211, such as a single mode fiber or a multi mode fiber, for supplying the observation light from the light source to the optical probe 202. The edge side of the fiber 211 is inserted to the optical probe 202.

In the optical probe 202, the edge side of the fiber 211 is fixed to X/Y scanner 212. The X/Y scanner 212 scans the edge side of the fiber 211 by the control and drive operation of a controller arranged in the control unit 203, which will be described later, thereby two-dimensionally (in the X and Y directions) scanning the subject portion with the observation light guided and outputted from the fiber 211.

The observation light outputted from the fiber becomes parallel light by a parallel lens 213, and is condensed to the subject portion by the objective optical system 214. A part of light scattered and reflected on or in the subject portion is captured to the optical probe 202. The light is inputted and guided to the fiber 211 via a route contrary to the above-mentioned route. Then, the input light is received by an optical detecting element arranged in the control unit 203, which will be described later, and is converted into an electronic signal.

The electronic signal which is optically converted by the optical detecting element in the control unit 203 is subjected to signal processing by a signal processing unit which will be described later. The output is inputted to the P.C. 204. The P.C. 204 generates image data corresponding to the tomogram, outputs the generated image data to the monitor 205, and displays the tomogram (optical imaging picture) on the display screen.

In the optical probe 202, the edge side comes into contact with the subject portion and, thereby, a positioning unit 220 positions the optical probe 202. The positioning unit 220 is detachably attached to the edge side of the optical probe. Then, the positioning unit 220 may be disposable.

The positioning unit 220 comprises a cover glass 221 which comes into contact with the subject portion at the surface of the subject portion of a fixing unit main body 220a. If the cover glass 221 is moved in the horizontal direction (X and Y directions) and vertical direction (Z direction) of the objective optical system 214, which will be described later, it is possible to keep a state in which the cover glass 221 comes into contact with the anatomy of the subject portion.

The positioning unit 220 comprises a field-of-view position adjusting mechanism 222 for adjusting the position in the field of view of the objective optical system 214 by movement in the horizontal direction (X and Y directions) and the vertical direction (Z direction) of the objective optical system 214. The field-of-view position adjusting mechanism 222 is formed by combining an X stage 223 which is moved in the X direction of the objective optical system 214, a Y stage 224 connected and fixed to the X stage 223, which is moved in the Y direction, and a Z stage 225 connected and fixed to the Y stage 224, which is moved in the Z direction. The detailed structure of the field-of-view position adjusting mechanism 222 will be described later.

The optical imaging apparatus can be formed by connecting the optical probe 202 to one of two units of a low-coherence unit for supplying low-coherence light, making the return light from the subject portion coherent, and receiving the light by the optical detecting element and a conjugate focusing unit for supplying laser beams (coherent light) and receiving the return light from the subject portion by the optical detecting element with a relationship of the conjugate focusing with the objective optical system 214, as the control unit 203 corresponding to the purpose.

The low-coherence unit will be described with reference to FIG. 16.

Referring to FIG. 16, a low-coherence unit 203A comprises an excessively high luminance light emitting diode (hereinafter, abbreviated to an SLD) 231 as a low-coherence light source. The SLD 231 has characteristics of the low-coherence light indicating the coherence only within a short distance range having a wavelength of, e.g., 980 nm and a coherent distance of, e.g., 15 μm. In other words, when the coherent light is divided to two light and thereafter is mixed again and thus the difference of the lengths of the two optical paths to the dividing point is within a short distance range of approximately 15 μm, the light is detected to as coherent light. When the difference is larger than the above-mentioned short distance range, the SLD 231 has characteristics of non-coherence.

The low-coherence light generated by the SLD 231 is made parallel by the light source lens 232 and is incident on the fiber 211. The low-coherence light incident on the fiber 211 is separated into the observation light and the reference light by an optical coupler 233 as light separating means. In place of the optical coupler, a half mirror (not shown) may be used as the light separating means.

The observation light separated by the optical coupler 233 is guided to the optical probe 202 by the fiber 211. As mentioned above, the subject portion is scanned in the horizontal direction by the X/Y scanner 212 and the light is condensed to the subject portion at the focus point of the objective light system 214. The X/Y scanner 212 scans two-dimensionally (X, Y direction) the subject portion by the edge side of the fiber 211 by applying a drive signal from a controller 237 which is controlled based on a control signal from the P.C. 204.

The reflection light and scattering light of the subject portion pass through the same optical path as that of the observation light and returns to the optical coupler 233 again.

The reference light separated by the optical coupler 233 is made parallel by the reflection lens 234 and is incident on the reflection mirror 235. The reference light incident on the reflection mirror 235 is modulated and reflected, and then is returned to the optical coupler 233 again via the reflection lens 234.

The reflection mirror 235 is arranged to a stage 236 which can advance and regress in the optical axis direction. The stage 236 has a driving unit (not shown) which advances and regresses by applying a drive signal from the controller 237. The reflection mirror 235 advances and regresses in the optical axis direction so that the length of the optical path of the reflected reference light is almost the same as that of the observation light.

The reference light and the observation light having almost the same length of the optical paths are made coherent in the optical path from the optical coupler 233. The coherent light is condensed by a light-receiving-side lens 238 and is received by a photo diode (hereinafter, abbreviated to a PD) as an optical detecting element of the light receiving means.

The PD 239 photoelectrically converts the coherent light into a coherent electronic signal. The photoelectrically converted coherent electronic signal is amplified by an amplifier (not shown) and is outputted to a signal processing unit 240.

The coherent electronic signal inputted to the signal processing unit 240 is subjected to signal processing by the signal processing unit 240. Thereafter, the processing signal is converted into a digital signal and is outputted to the P.C. 204.

The P.C. 204 generates image data corresponding to the tomogram by using the inputted digital signal. The generated image data is outputted to a monitor 205 and is displayed on a display screen as a low-coherence image (optical imaging picture) of the subject portion.

Next, a conjugate focusing unit 203B will be described with reference to FIG. 17.

Referring to FIG. 17, the conjugate focusing unit 203B has a laser diode (hereinafter, abbreviated to an LD) 241 as a light source of the coherent light.

The coherent light generated by the LD 241 is made parallel by the light-source-side lens 232, and is incident on the fiber 211. The coherent light incident on the fiber 211 is guided to the optical probe 202 via the optical coupler 233 as the observation light.

As mentioned above, the subject portion is scanned in the horizontal direction by the X/Y scanner 212 with the observation light guided to the optical probe 202, and the light is condensed to the subject portion at the focus point of the objective optical system 214. Then, the objective optical system 214 has a large numerical aperture (N.A.: Numerical Aperture).

The reflection light and scattering light of the subject portion pass through the same optical path as that of the observation light and returns to the optical coupler 233 again. The observation light returned to the optical coupler 233 is received by the PD 239 via the optical coupler 233 and is photoelectrically converted. The PD 239 has a conjugate relationship with the objective optical system 214, and forms a conjugate focusing optical system together with the objective optical system 214. That is, the conjugate focusing unit 203B has a conjugate focusing optical system between the LD 241 and the objective optical system 214.

Similarly to the above-mentioned low-coherence unit 203A, the electronic signal photoelectrically converted by the PD 239 is amplified and outputted to the signal processing unit 240. After the output signal is subject to the signal processing by the signal processing unit 240, the image data corresponding to the tomogram is generated by the P.C. 204. The generated image data is outputted to the monitor 205 and is displayed on the display screen as a conjugate focusing image (optical imaging picture).

The edge side of the optical probe 202 connected to the low-coherence unit 203A or the conjugate focusing unit 203B comes into contact with the subject portion by the positioning unit 220, thereby positioning the optical probe 202.

The positioning unit 220 is formed by combining the field-of-view position adjusting mechanism 222 to the X stage 223, the Y stage 224, and the Z stage 225, as mentioned above.

First, the structure of the field-of-view position adjusting mechanism 222 will be described by using the X stage 223.

Referring to FIGS. 18 and 19, the X stage 223 has an X base 251 which is movably arranged in the X direction in the space formed in the stage main body 223a. In the X base 251, a penetrating unit 251a to which the objective optical system 214 is inserted is formed.

The X base 251 comprises a pressing and fixing unit 253 whose one end is pressed and fixed to the stage main body 223a by energization power of a spring portion 252 and whose another end presses the stage main body 223a against the energization power of the spring portion 252, to move and fix the X base 251 in the X direction.

In the pressing and fixing unit 253, a pressing plate 253b which shifts in the X direction moves the X base 251 in the X direction via a ball indirect member 253c by rotatably screwing a picking screw portion 253a projected to the outer circumference of the stage main body 223a.

Thus, the X base 251 is moved in the X direction in a state in which the objective optical system 214 of the optical probe 202 is inserted into the penetrating portion 251a.

Therefore, the positioning unit 220 moves the X base 251 of the X stage 223 in the X direction of the objective optical system 214 by screwing the picking screw portion 253a of the X stage 223. Simultaneously, bases of the Y stage 224 and the Z stage 225 are moved in the X direction.

Incidentally, the Y stage 224 has the similar structure of the X stage 223. Although not shown, the Z stage 225 is freely rotated to the Y stage 224, thereby moving the stage main body 223a in the Z direction.

The positioning unit 220 allows the cover glass 221 to come into contact with the subject portion. Simultaneously, the cover glass 221 moves in the horizontal direction (X and Y directions) and the vertical direction (Z direction) of the objective optical system 214. Consequently, the position in the field of view of the objective optical system 214 is adjusted by moving the cover glass 221.

The cover glass 221 forms a friction pattern 254, as contact keeping means for keeping the contact state of the cover glass 221 with the anatomy of the subject portion, in which concave and convex portions are formed on the surface side of the subject portion and a friction coefficient is increased as shown in FIG. 20. Incidentally, in place of the friction pattern 254, as the contact keeping means, a detachable adhesive material such as a double-faced tape or silicon adhesive may be provided.

Thus, the positioning unit 220 can keep the contact state of the cover glass 221 with the anatomy of the subject portion if the cover glass 221 is moved in the horizontal direction (X and Y directions) and vertical direction (Z direction) of the objective optical system 214.

Referring to FIG. 15, the optical imaging apparatus 201 with the above-mentioned structure is used to obtain the tomogram of the subject portion by connecting the optical probe 202 to one of the low-coherence unit 203A and the conjugate focusing unit 203B as the control unit 203 corresponding to the purpose.

The optical imaging apparatus 201 presses the cover glass 221 of the optical probe 202 to the anatomy of the subject portion. Thus, the cover glass 221 comes into contact with the anatomy of the subject portion. As mentioned above, the optical imaging apparatus 201 irradiates the subject portion with the observation light supplied from the control unit 203 and captures the return light as the reflection light and scattering light from the subject portion, thereby obtaining the tomogram of the subject portion. The tomogram is displayed on the display screen of the monitor 205 as the optical imaging picture.

Herein, it is assumed that the position of the objective optical system 214 is positioned in the right direction of the anatomy of the subject portion as shown in FIG. 21 and the optical probe 202 obtains the tomogram in the field of view for observation at this position. In this case, it is assumed that an object portion to be observed by a user is positioned in the left direction of the cover glass 221.

The user operates the picking screw portion 253a of the X stage 223, thereby moving the positioning unit 220 in the right direction of the objective optical system 214. Incidentally, the X direction in the figure is in the right and left direction on the sheet.

Then, as mentioned above, the positioning unit 220 allows the cover glass 221 to move in the right direction of the objective optical system 214 in the contact state of the cover glass 221 with the subject portion.

Thus, referring to FIG. 22, the position of the optical probe 202 is adjusted in the field of view so that the position of the objective optical system 214 is in the left direction of the anatomy of the subject portion. In the field of view for observation at this position, the tomogram can be obtained. Although a description is omitted, the cases in the Y and Z directions are the same as the above description.

Thus, according to the fifth embodiment, the optical imaging apparatus 201 can adjust the range of the filed of view for observation in the horizontal direction (X and Y directions) and vertical direction (Z direction) of the subject portion.

As a consequence, according to the fifth embodiment, the optical imaging apparatus 201 can easily move the filed of view for observation within a wide range and the optical probe 202 with small size and high resolution can be realized.

The optical imaging apparatus may comprise an optical probe as shown in FIG. 23.

Referring to FIG. 23, the optical probe 202B is formed by detachably attaching a positioning unit 220B having a field-of-view position adjusting mechanism 222B which is moved in the horizontal direction (X and Y directions) of the objective optical system 214 on the edge side of the optical probe 202B.

The field-of-view position adjusting mechanism 222B arranged to the positioning unit 220B comprises an XY stage 260 which moves in the X and Y directions of the objective optical system 214.

Referring to FIGS. 24 and 25, the XY stage 260 is arranged so that the XY base 261 can be moved in the X and Y directions in the space formed in a stage main body 260a. The XY base 261 has the cover glass 221 in which the friction pattern 254 is formed on the subject portion side.

The XY base 261 comprises an X pressing and fixing unit 262 whose one end is pressed and fixed to the stage main body 260a by energization power of the spring portion 252 and whose another end presses the stage main body 260a against the energization power of the spring portion 252, to move and fix the XY base 261 in the X direction. The X pressing and fixing unit 262 moves the XY base 261 in the X direction via a ball indirect member 262c by rotatably screwing a picking screw portion 262a projected into the outer circumference of a stage main body 260a.

On the other hand, the XY base 261 comprises a Y pressing and fixing unit 263 whose one end is pressed and fixed to the stage main body 260a by energization power of the spring portion 252 and whose another end presses the stage main body 260a against the energization power of the spring portion 252, to move and fix the XY base 261 in the Y direction. The Y pressing and fixing unit 263 moves the XY base 261 in the Y direction via the ball indirect member 262c by rotatably screwing a picking screw portion 263a projected to the outer circumference of the stage main body 260a.

Therefore, the positioning unit 220 moves the XY base 261 of the XY stage 260 in the X direction or the Y direction of the objective optical system 214 by screwing the picking screw units 262a and 263a of the XY stage 260. Thus, the cover glass 221 is moved to adjust the position in the field of view of the objective optical system 214.

Incidentally, a motor (not shown) is provided for the XY stage 260 and the motor is controlled and driven by the control unit 203. Thus, the positioning unit 220 may electrically be driven.

According to the present modification, as compared with that according to the fifth embodiment, the positioning unit 220 can further be reduced in size. The optical probe 202 can be realized with smaller size and high operability.

The optical imaging apparatus may comprise an optical probe as shown in FIG. 26.

Referring to FIG. 26, an optical probe 202C is formed by arranging an absorbing pump 271 as contact keeping means for keeping the contact state of a cover glass 221C with the anatomy of the subject portion.

An absorbing tube 271a extending from the absorbing pump 271 is inserted into the positioning unit 220B, is inserted and fixed to a groove portion 272 which is formed at the side surface of the subject portion of the cover glass 221C. Further, the absorbing tube 271a opens at the bottom of the groove portion 272. Further, referring to FIG. 27, the four groove portions 272 are formed at the side surface of the cover glass 221C.

As a consequence, in the optical probe 202C, the anatomy of the subject portion is absorbed in the groove portion 272 of the cover glass 221C by using absorbing power of the absorbing pump 271 which is transmitted from the absorbing tube 271a. Thus, it is possible to keep the contact state of the cover glass 221C with the anatomy of the subject portion. Incidentally, the absorbing pump 271 may comprise a starting switch (not shown) at the outer circumference of the optical probe. Alternatively, the absorbing pump 271 may be controlled and driven via a cable by a control signal from the control unit 203.

Therefore, the optical probe 202C can keep the contact state of the cover glass 221C with the anatomy of the subject portion if the cover glass 221C is moved in the horizontal direction (X and Y directions) of the objective optical system 214.

Consequently, according to the second modification of the fifth embodiment, as compared with that according to the first modification, the optical imaging apparatus can preferably keep the contact state of the cover glass 221C.

According to the fifth embodiment, in the optical imaging apparatus, the present invention is applied to the hand-held probe. However, among the light source (low-coherence light source or coherent light source), the light separating means (optical coupler), the optical scanning means (X/Y scanner) and the objective optical system, at least the objective optical system is included in the casing of the hand-held probe.

Sixth Embodiment

Figure 28:
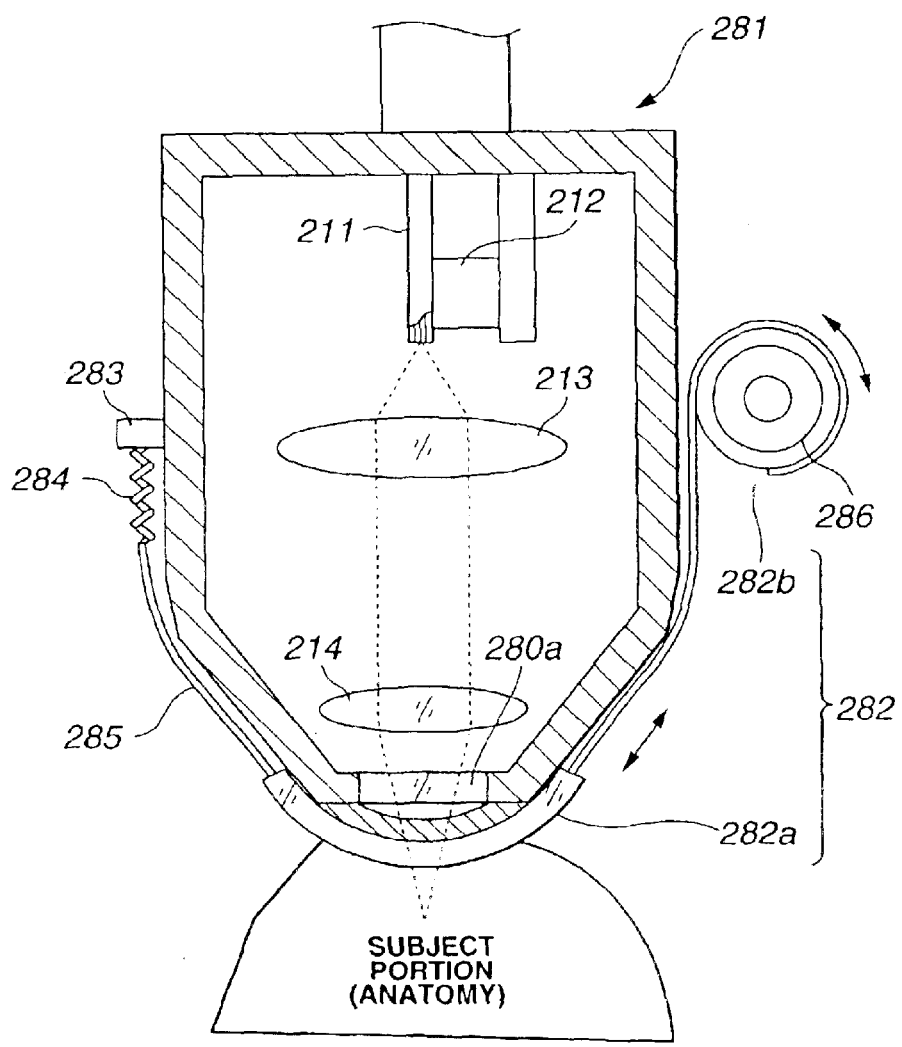
FIG. 28 is an explanatory diagram showing an optical probe in an optical imaging apparatus according to a sixth embodiment of the present invention.
Figure 29:
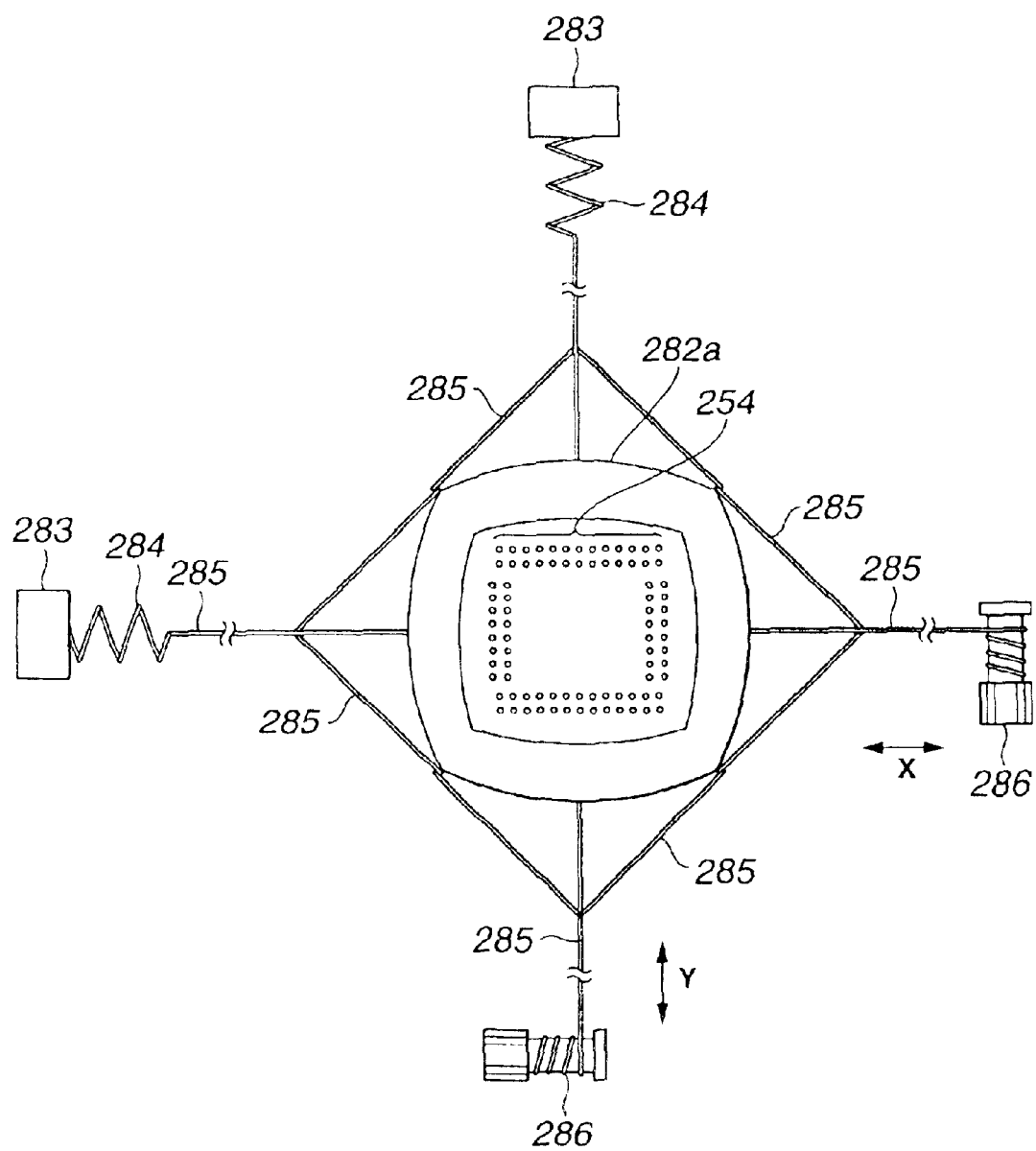
FIG. 29 is an explanatory diagram schematically showing a mechanism for adjusting the position in a filed of view in FIG. 28.

FIGS. 28 and 29 relate to a sixth embodiment of the present invention, FIG. 28 is an explanatory diagram showing an optical probe in an optical imaging apparatus according to the sixth embodiment of the present invention, and FIG. 29 is an explanatory diagram schematically showing a mechanism for adjusting the position in a filed of view in FIG. 28.

According to the sixth embodiment, the present invention is applied to the hand-held probe in which the edge side is made thin in diameter in the case of a small area of the subject portion. Other structure is the same as that according to the fifth embodiment and, therefore, a description is omitted. Then, the same components are described with the same reference numerals.

That is, referring to FIG. 28, the optical imaging apparatus according to the sixth embodiment comprises an optical probe 281 in which the edge side is made thin in diameter in the case of the small area of the subject portion.

An observation window 280a is arranged at the edge side of the optical probe 281, which is made thin in diameter. The optical probe 281 comprises a positioning unit 283 which positions the optical probe 281 by a contact state of a cover sheet 282a with the subject portion so as to cover the observation window 280a.

The positioning unit 283 comprises the cover sheet 282a made of a transparent member through which the observation light irradiated from the objective optical system 214 passes. Further, the positioning unit 283 comprises a filed-of-view position adjusting mechanism 282b which adjusts the position in filed of view of the objective optical system 214 by movement of the cover sheet 282a in the horizontal direction (X and Y directions) of the objective optical system 214 using traction of the cover sheet 282a.

Referring to FIG. 29, wires 285 are extended from a spring portion 284 which is suspended from a projecting portion 283 of the outer circumference of the probe main body and the wires 285 are suspended from ends of the cover sheet 282a. Further, the wires 285 which are suspended from other ends of the cover sheet 282a are wound and tractive against energization of the spring portion 284 by using a winding portion 286 arranged outside the probe main body. Thus, tension is applied by wining to the filed-of-view position adjusting mechanism 282b.

Furthermore, in the filed-of-view position adjusting mechanism 282b, the wire 285 is extended in directions of two axes perpendicular thereto and, thus, the cover sheet 282a is wound in the horizontal direction (X and Y directions) of the objective optical system 214.

The cover sheet 282a forms the friction pattern 254 (not shown), similarly to the cover glass 221C described according to the fifth embodiment.

The filed-of-view position adjusting mechanism 282b may have the winding portion 286 which is wound by a user. Alternatively, it may be electrically driven by controlling and driving a motor (not shown) by the control unit 203 which is provided for the winding portion 286.

The optical imaging apparatus having the above-structured optical probe 281 is connected to the control unit 203 so as to obtain the tomogram of the subject portion, similarly to the description according to the fifth embodiment.

In the optical imaging apparatus, the cover sheet 282a of the optical probe 281 is pressed to the anatomy of the subject portion and comes into contact with it. The observation light supplied from the control unit 203 is irradiated to the subject portion and the return light, as the reflection light and scattering light, is captured, thus to obtain the tomogram of the subject portion. The tomogram is displayed on the display screen of the monitor 205 as an optical imaging picture.

It is assumed that in the optical probe 281, the position of the objective optical system 214 is in the right direction of the anatomy of the subject portion and the tomogram is obtained in the field of view at this position. Further, it is assumed that in this case, an object portion to be observed by the user is in the left direction of the cover sheet 282a.

Then, the user winds the winding portion 286 in the X direction, and moves the cover sheet 282a in the right direction of the objective optical system 214. Incidentally, the X direction is in the right and left directions.

Then, as mentioned above, the positioning unit 283 is moved in the right direction of the objective optical system 214 in the contact state of the cover sheet 282a with the subject portion.

Consequently, the position of the objective optical system 214 in the field of view is adjusted in the left direction of the anatomy of the subject portion and the optical probe 281 can obtain the tomogram in the field of view at this position. Although a description is omitted, the case in the Y direction is the same as that in the X direction.

As a result, the optical imaging apparatus according to the sixth embodiment has the same advantages as those according to the fifth embodiment. In addition, in the small area of the subject portion, the range of the filed of view for observation can be adjusted in the horizontal direction (X and Y directions).

Seventh Embodiment

Figure 30:
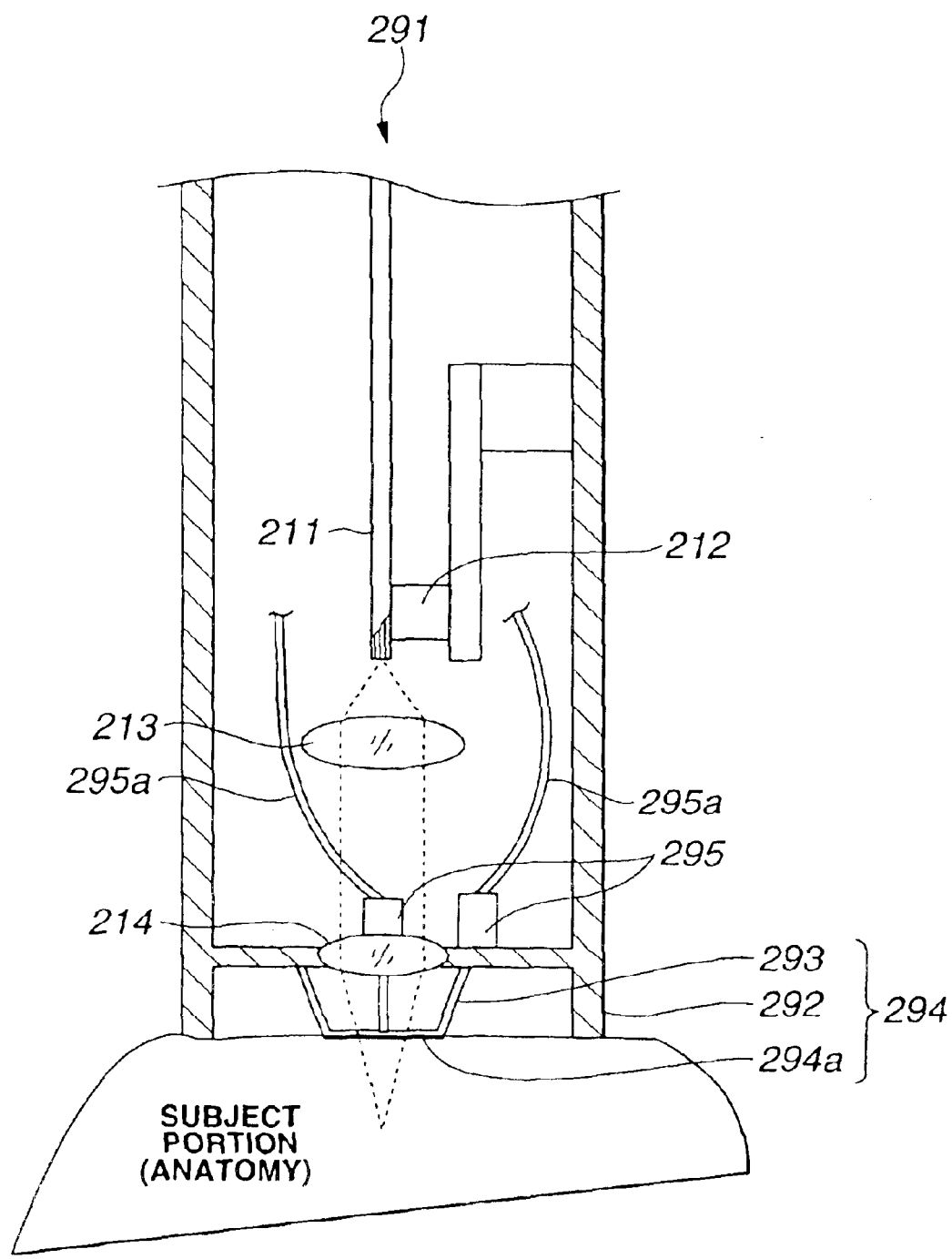
FIG. 30 is an explanatory diagram showing an optical probe in an optical imaging apparatus according to a seventh embodiment of the present invention.
Figure 31:
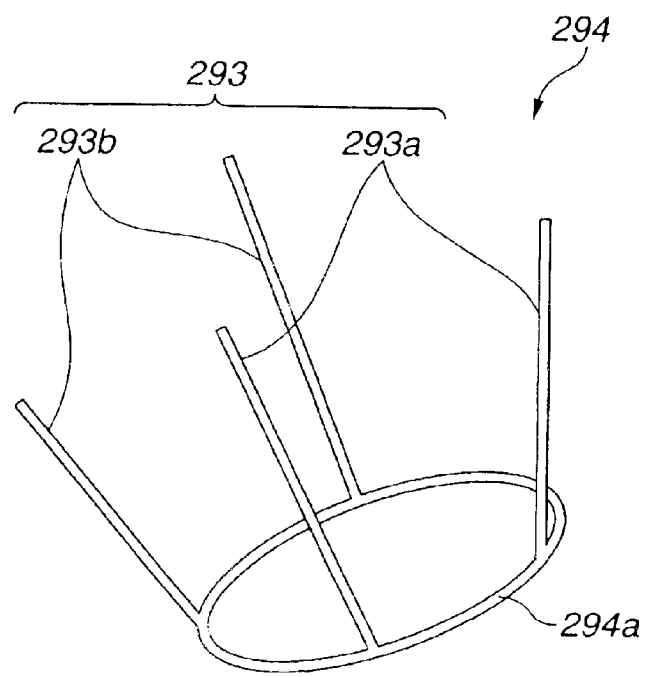
FIG. 31 is a perspective view showing a ring-shaped metal member in FIG. 30.
Figure 32:
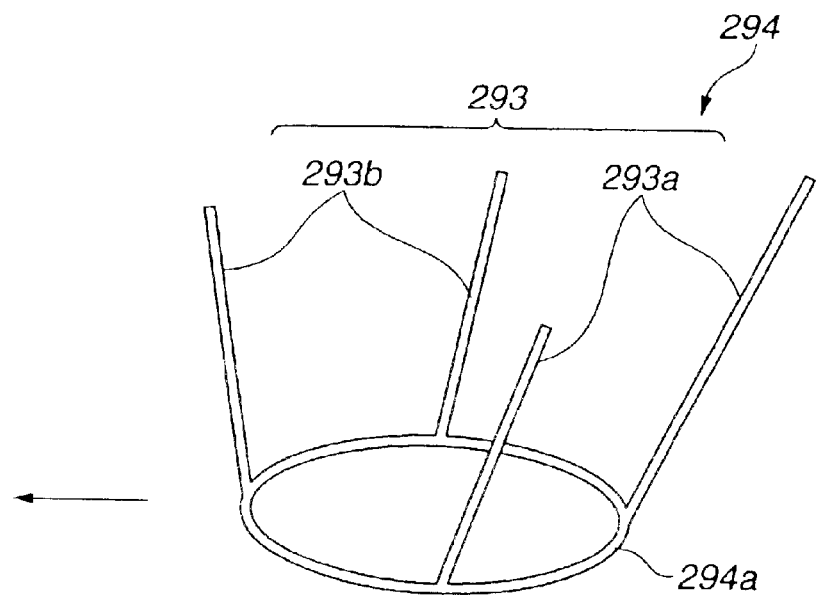
FIG. 32 is a perspective view of the ring-shaped metal member when leg portions on the right side are stretched and are moved in the left side of the objective optical system.
Figure 33:
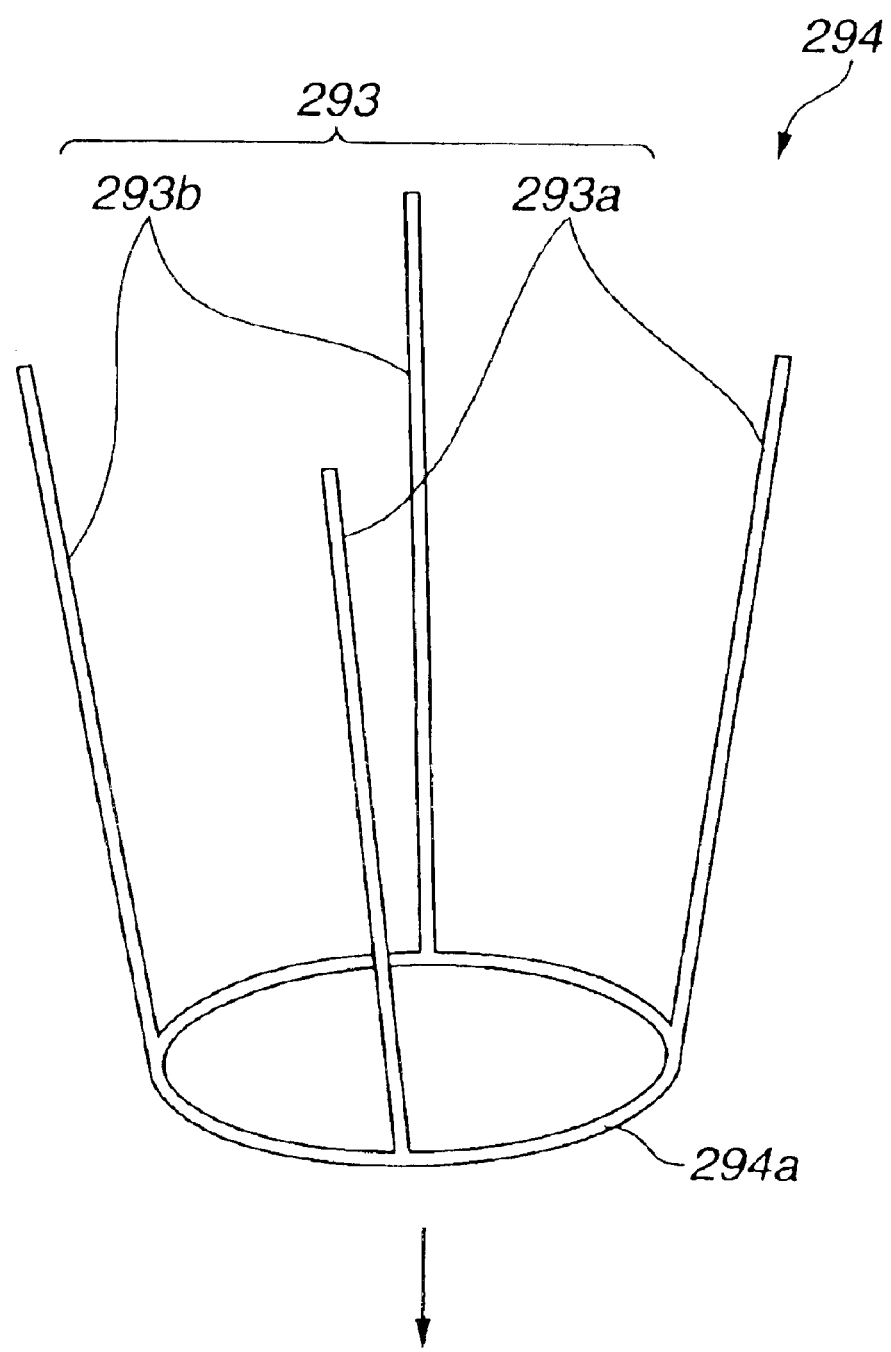
FIG. 33 is a perspective view of the ring-shaped metal member when all four leg portions are stretched and are moved in the vertical direction (Z direction) of the objective optical system.
Figure 34:
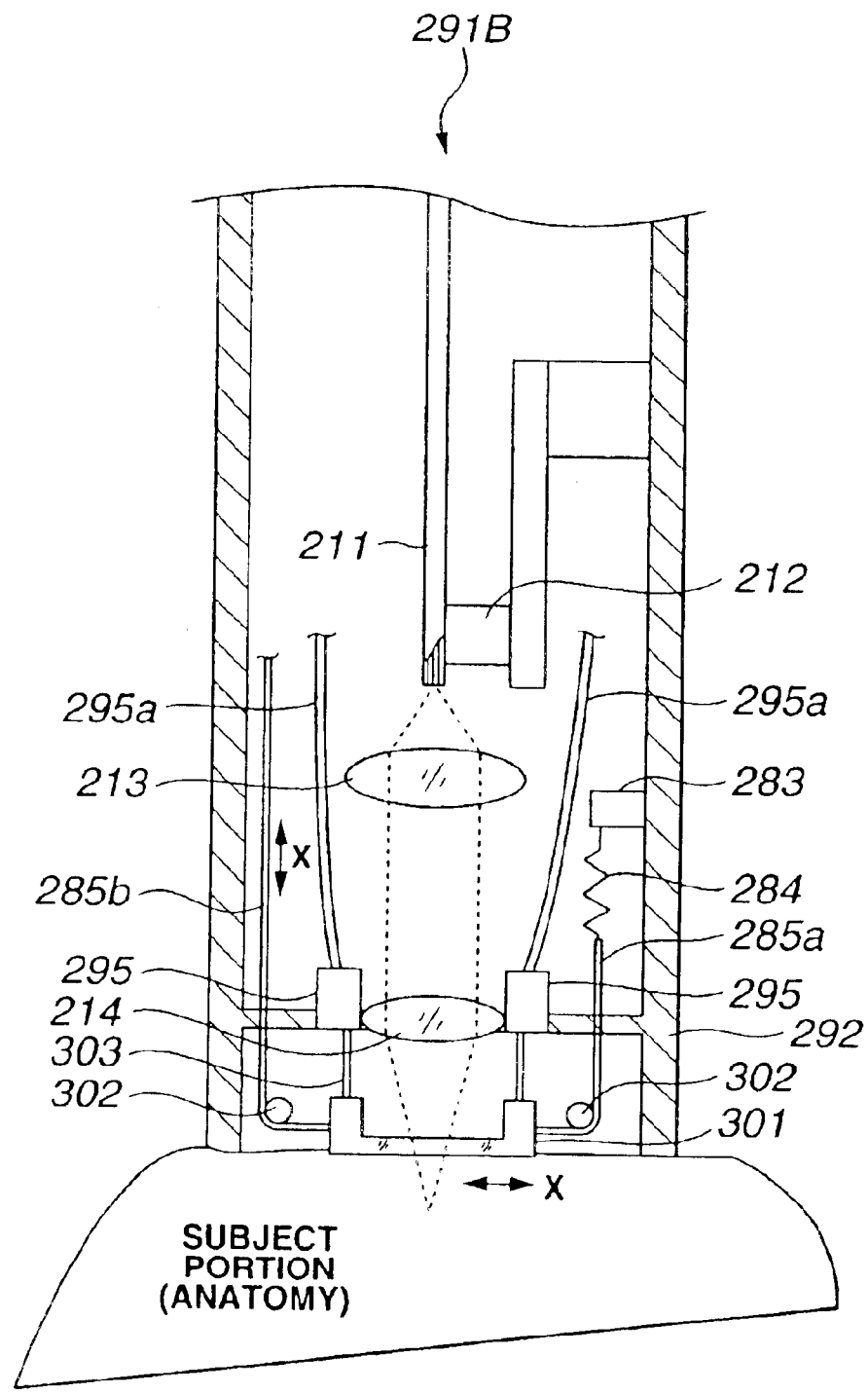
FIG. 34 is an explanatory diagram showing of the optical probe according to a modification.
Figure 35:
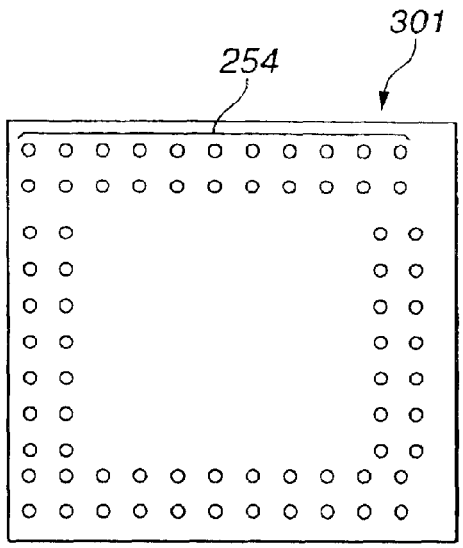
FIG. 35 is an explanatory diagram showing a surface side of the subject portion of a concave plate member in FIG. 34.

FIGS. 30 to 35 relate to a seventh embodiment of the present invention, FIG. 30 is an explanatory diagram showing an optical probe in an optical imaging apparatus according to the seventh embodiment of the present invention, FIG. 31 is a perspective view showing a ring-shaped metal member in FIG. 30, FIG. 32 is a perspective view of the ring-shaped metal member when a leg portion on the right side is stretched and is moved on the left side of the objective optical system, FIG. 33 is a perspective view of the ring-shaped metal member when all four leg portions are stretched and are moved in the vertical direction (z direction) of the objective optical system, FIG. 34 is an explanatory diagram showing an optical probe according to a modification, and FIG. 35 is an explanatory diagram showing the surface side of the subject portion of a concave plate member in FIG. 34.

According to the fifth and sixth embodiments, the present invention is applied to the hand-held probe which is formed by a grippable casing. However, according to the seventh embodiment, the present invention is applied to an optical probe which is inserted into an endoscope (not shown) or a channel for inserting treatment appliance of the endoscope. Other structure is the same as that according to the fifth and sixth embodiments and, therefore, a description is omitted and the same components are described with the same reference numerals.

Referring to FIG. 30, the optical imaging apparatus according to the seventh embodiment comprises an optical probe 291 which is inserted into the endoscope (not shown) or a channel for inserting treatment appliance of the endoscope.

The optical probe 291 comprises a cylindrical portion 292 at the outer circumference thereof, which is extended cylindrically as a positioning unit. Further, the optical probe 291 comprises the objective optical system 214 in the center of the bottom of the cylindrical portion 292.

The optical probe 291 comprises s ring-shaped metal member 294 with leg portions 293 which are in the probe main body, as a field-of-view position adjusting mechanism for moving the cylindrical portion 292 in the horizontal direction (X and Y directions) and vertical direction (Z direction) of the objective optical system 214 in a state in which the cylindrical portion 292 comes into contact with the subject portion. The leg portions 293 of the ring-shaped metal member 294 are heated by a heater 295 arranged at a predetermined position in the bottom of the cylindrical portion 292. Incidentally, power of the power source is supplied from the control unit 203 to the heater 295 via an electric wire 295a.

Referring to FIG. 31, the ring-shaped metal member 294 has four leg portions 293 opposed thereto, which are formed in the directions of two axes perpendicular thereto. In the four leg portions 293, two leg portions 293a are made of memory metal and two remaining leg portions 293a opposed to the former ones are made of memory metal or a normal metal.

Thus, the leg portions 293 of the ring-shaped metal member 294 are arranged to the cylindrical portion 292 of the probe main body in the direction of the probe main body. When heat from the heater 295 is transmitted to the leg portions 293 via the cylindrical portion 292, the memory metal of the leg portions 293a is stretched to move the ring-shaped metal member 294 in the horizontal direction (X and Y directions) and horizontal direction (Z direction) of the objective optical system 214 and the position of the objective optical system 214 in the filed of view is adjusted.

The optical imaging apparatus having the optical probe 291 with the above-mentioned structure is connected to the control unit 203 to obtain the tomogram of the subject portion, similarly to the description according to the fifth embodiment.

In the optical imaging apparatus, the cylindrical portion 292 of the optical probe 291 is pressed and comes into contact with the anatomy of the subject portion. Further, the bottom 294a of the ring-shaped metal member 294 is pressed and comes into contact with the anatomy of the subject portion. Then, the subject portion is irradiated with the observation light fed from the control unit 203 and the return light as the reflection light and scattering light from the subject portion is captured. Thus, the tomogram of the subject portion is obtained and the tomogram is displayed on the display screen as the optical imaging picture.

Herein, it is assumed that in the optical probe 291, the position of the objective optical system 214 is in the left direction of the anatomy of the subject portion and the tomogram is obtained in the field of view at this position. Further, it is assumed that in this case, an object portion to be observed by the user is in the right direction of the cylindrical portion 292. Incidentally, the X direction is in the right and left directions.

The user heats the heater 295 in the X direction. Referring to FIG. 32, the right leg portions 293 of the ring-shaped metal member 294 are stretched. Then, the ring-shaped metal member 294 moves in the left direction of the objective optical system 214 in the state in which a bottom portion 294a comes into contact with the subject portion.

Therefore, in the optical probe 291, the position of the objective optical system 214 in the field of view is adjusted in the right direction of the anatomy of the subject portion and the tomogram is obtained in the field of view at this position. Although not described, the case in the Y direction (vertical direction of the sheet) is the same as that in the X direction.

When the object portion to be observed is in the depth direction (vertical direction) of the anatomy, the user heats all the heaters 295. Referring to FIG. 33, all the four leg portions 293 of the ring-shaped metal member 294 are stretched. Then, the ring-shaped metal member 294 moves in the vertical direction (Z direction) of the objective optical system 214 in the contact state of the bottom portion 294a with the subject portion.

Therefore, the position of the optical probe 291 in the field of view is adjusted so that the position of the objective optical system 214 is in the vertical direction (Z direction) of the anatomy of the subject portion and the tomogram can be obtained in the field of view at this position.

As a result, the optical imaging apparatus according to the seventh embodiment has the same advantages as those according to the fifth embodiment.

The optical imaging apparatus may comprise an optical probe 291 as shown in FIG. 34.

Referring to FIG. 34, in place of the ring-shaped metal member 294, as a filed-of-view position adjusting mechanism, a concave plate member 301 is arranged in the optical probe 291B. The concave plate member 301 is made of a transparent member for transmitting the observation light which is irradiated from the objective optical system 214.

In the concave plate member 301, two wires 285a and 285b fixed to both ends thereof are changed in the direction by a roller unit 302, are inserted into the bottom of the cylindrical portion 292, and are extended in the probe main body. One wire 285a is connected to the spring portion 284 suspended from the projecting portion 283 in the probe. The other wire 285b is wound and is tractive against the energization of the spring portion 284 using the winding unit 286 (not shown) arranged in the probe main body and moves the concave plate member 301 in the horizontal direction (X and Y directions) of the objective optical system 214.

The wires 285 (285a, 285b) are arranged in the X direction (right and left directions) and the Y direction (vertical direction of the sheet) of two perpendicular axes. The wires 285 (285a, 285b) in FIG. 34 are X wires which move the concave plate member 301 in the X direction (right and left directions of the sheet) of the objective optical system 214.

Further, in the concave plate member 301, a spring 303 is fixed thereto in the direction opposed to the probe main body. The spring 303 is suspended from the heater 295 which is arranged at a predetermined position in the bottom of the cylindrical portion 292. When the heat from the heater 295 is transmitted to the spring 303, the concave plate member 301 is stretched. Thus the concave plate member 301 is moved in the vertical direction (up and down directions of the sheet) of the objective optical system 214, and the position of the objective optical system 214 in the field of view is adjusted.

Referring to FIG. 35, the concave plate member 301 comprises the friction pattern 254 at the surface side of the subject portion, similarly to the cover glass 221 described according to the fifth embodiment.

Therefore, if the concave plate member 301 is moved in the horizontal direction (X and Y directions) and horizontal direction (Z direction) of the objective optical system 214, the concave plate member 301 can keep the contact state thereof with the anatomy of the subject portion.

In the field-of-view position adjusting mechanism 282b, the winding unit 286 may be wound by the user. Alternatively, the field-of view position adjusting mechanism 282b may electrically be driven by controlling and driving a motor (not shown) by the control unit 203 which is provided for the winding unit 286.

Thus, according to the present modification of the seventh embodiment, as compared with that according to the sixth embodiment, the optical imaging apparatus can keep the contact state with the subject portion.

According to the seventh embodiment, in the optical imaging apparatus, the present invention is applied to the optical probe which is inserted into the endoscope (not shown) or the channel for inserting treatment appliance of the endoscope. However, among the light source (low-coherence light source or coherent light source), the light separating means (optical coupler), the optical scanning means (X/Y scanner) and the objective optical system, at least the objective optical system is included in the casing of the hand-held probe.

Eighth Embodiment

Figure 38:
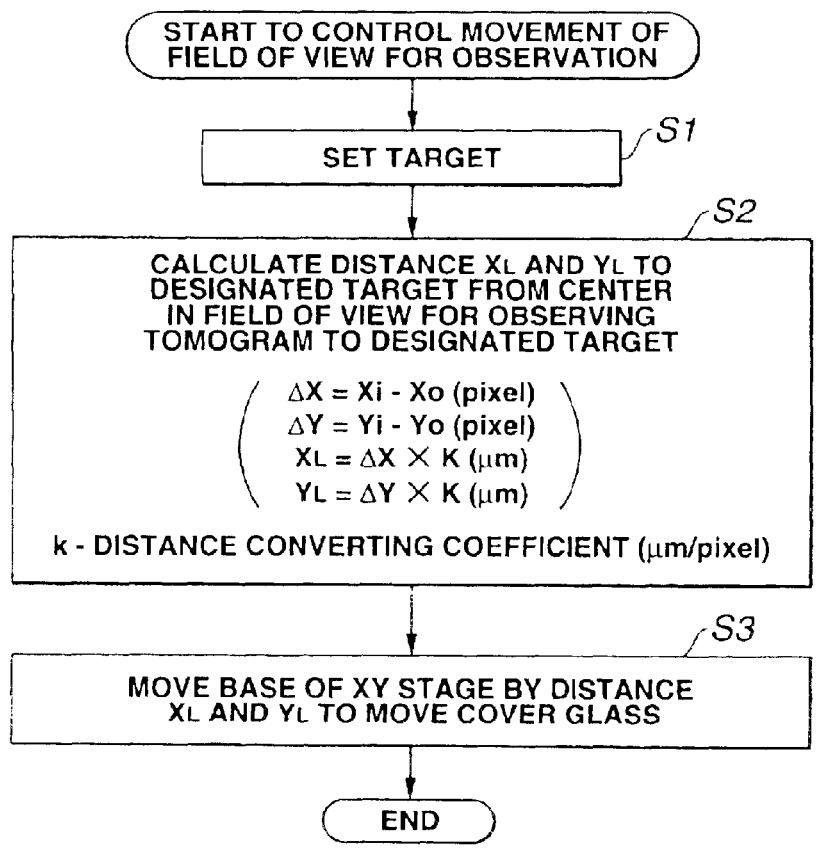
FIG. 38 is a flowchart showing processing for controlling the movement of the field of view.
Figure 36:
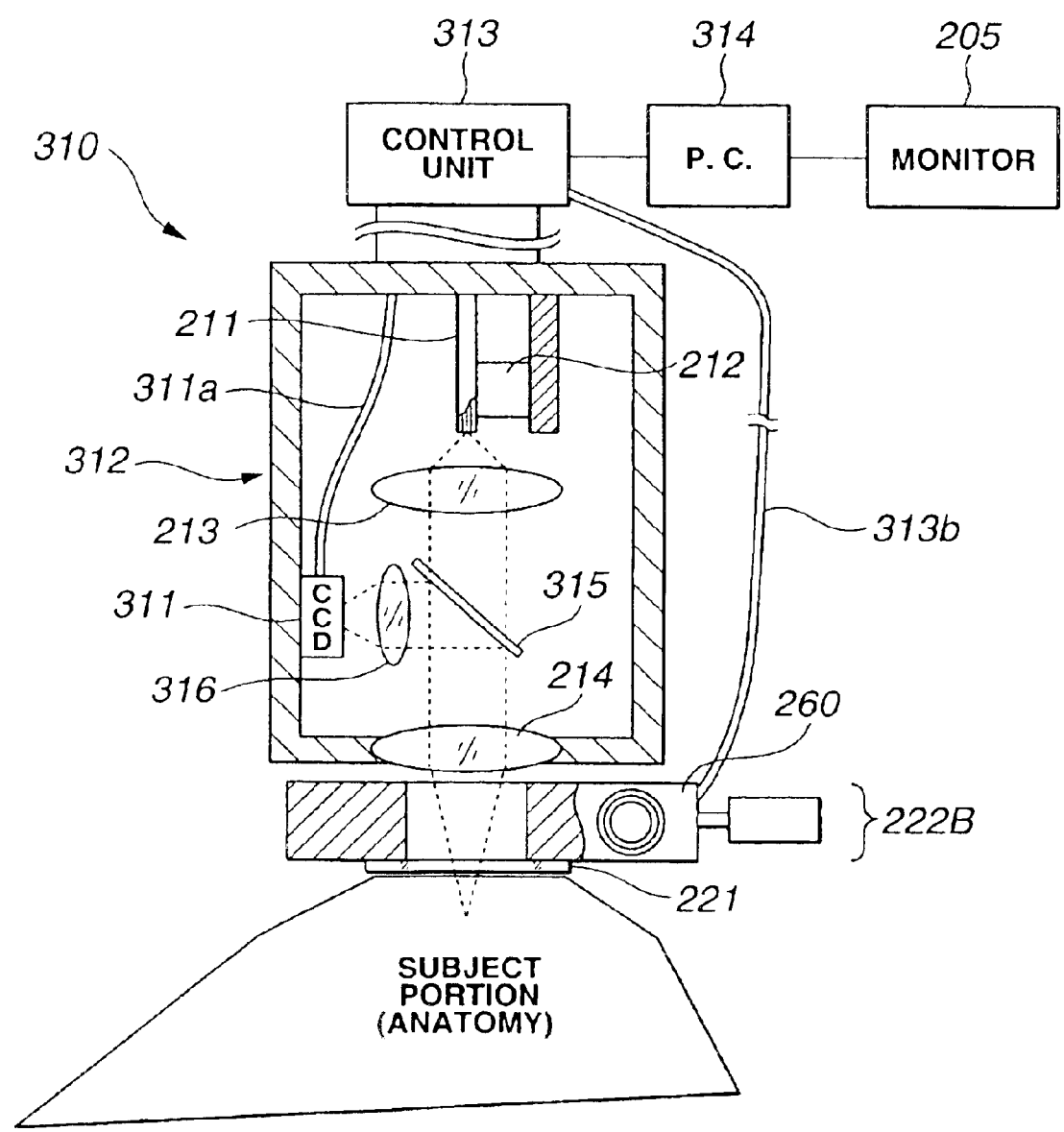
FIG. 36 is a diagram showing the entire structure of an optical imaging apparatus according to an eighth embodiment of the present invention.
Figure 37:
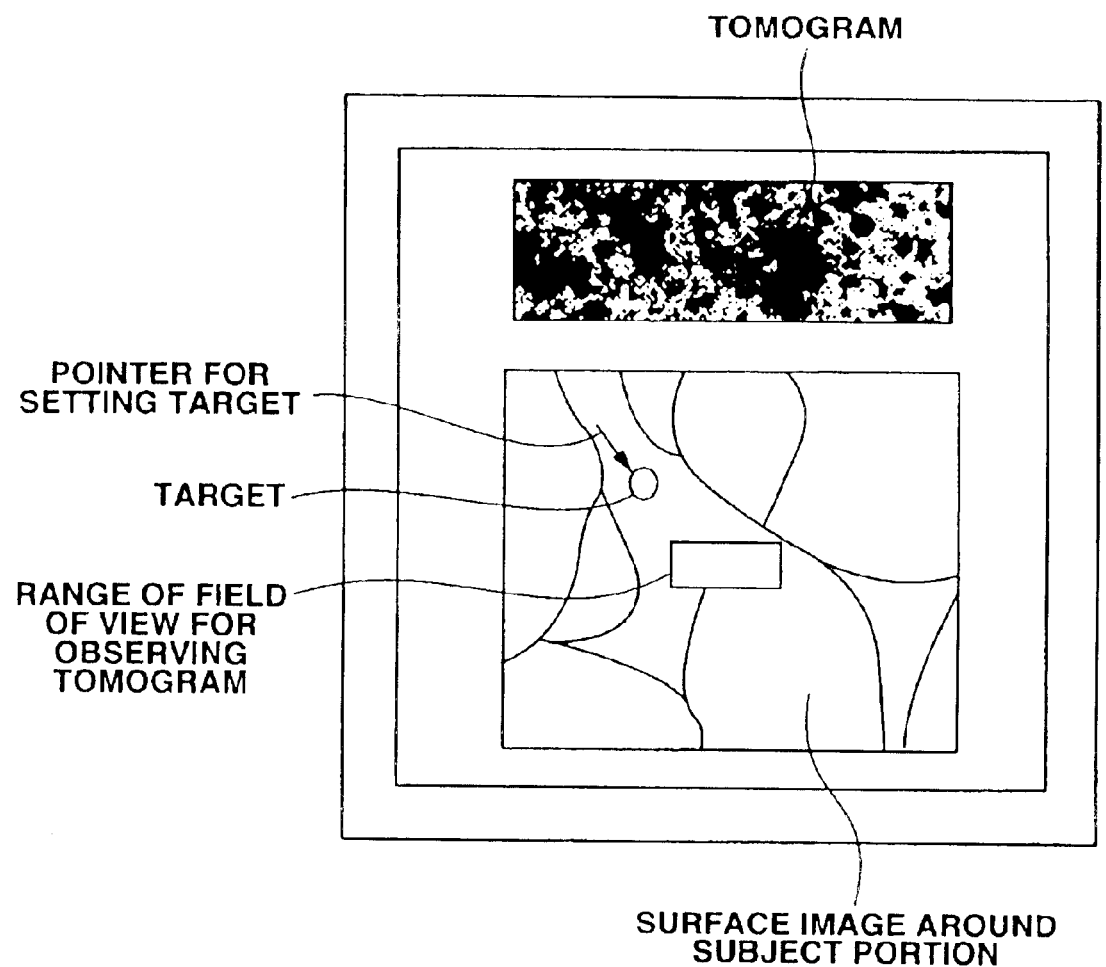
FIG. 37 is an explanatory diagram showing an image display example of a monitor in FIG. 36.
Figure 39:
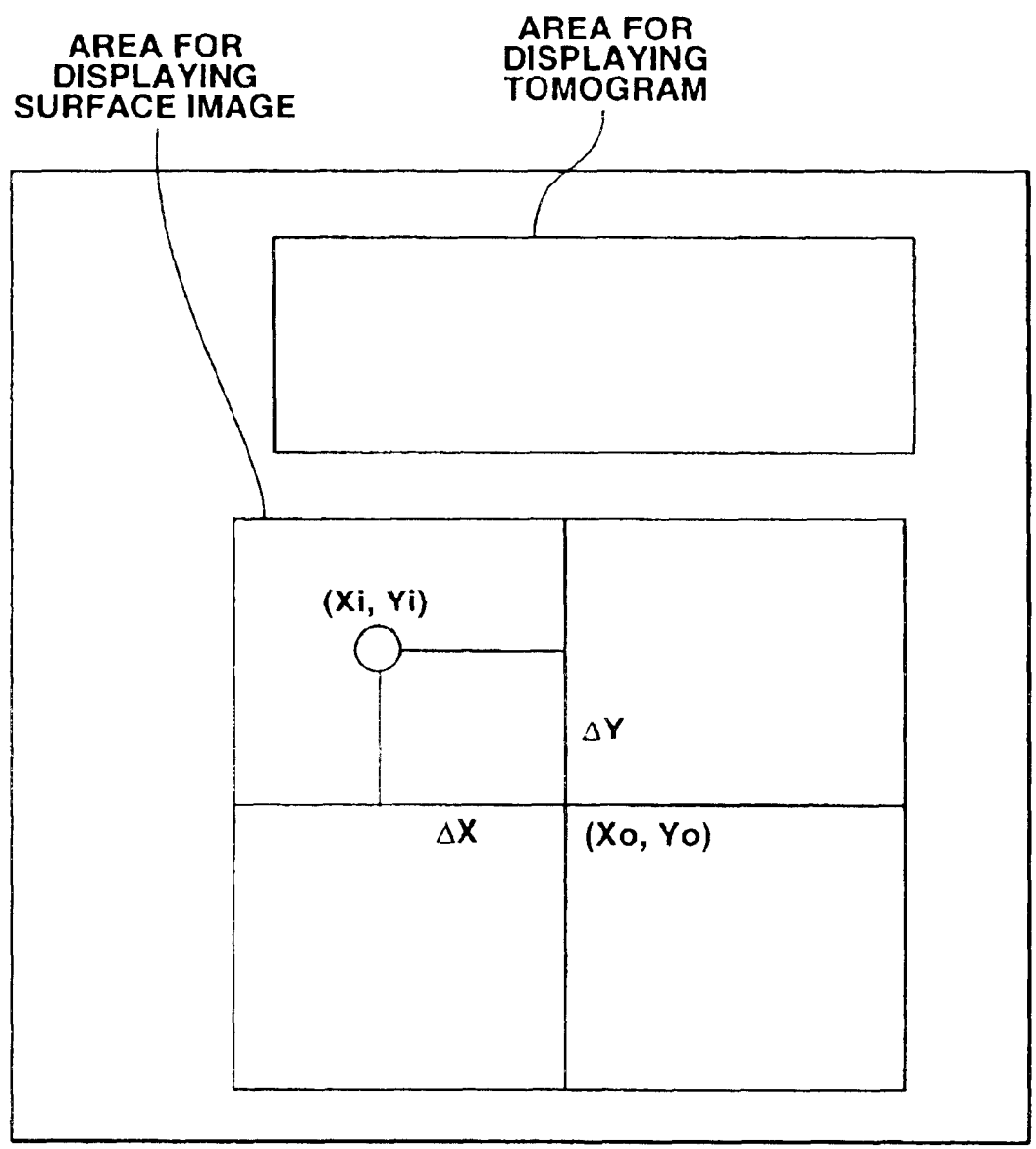
FIG. 39 is a diagram showing coordinates for calculation in the flowchart of FIG. 38.
Figure 40:
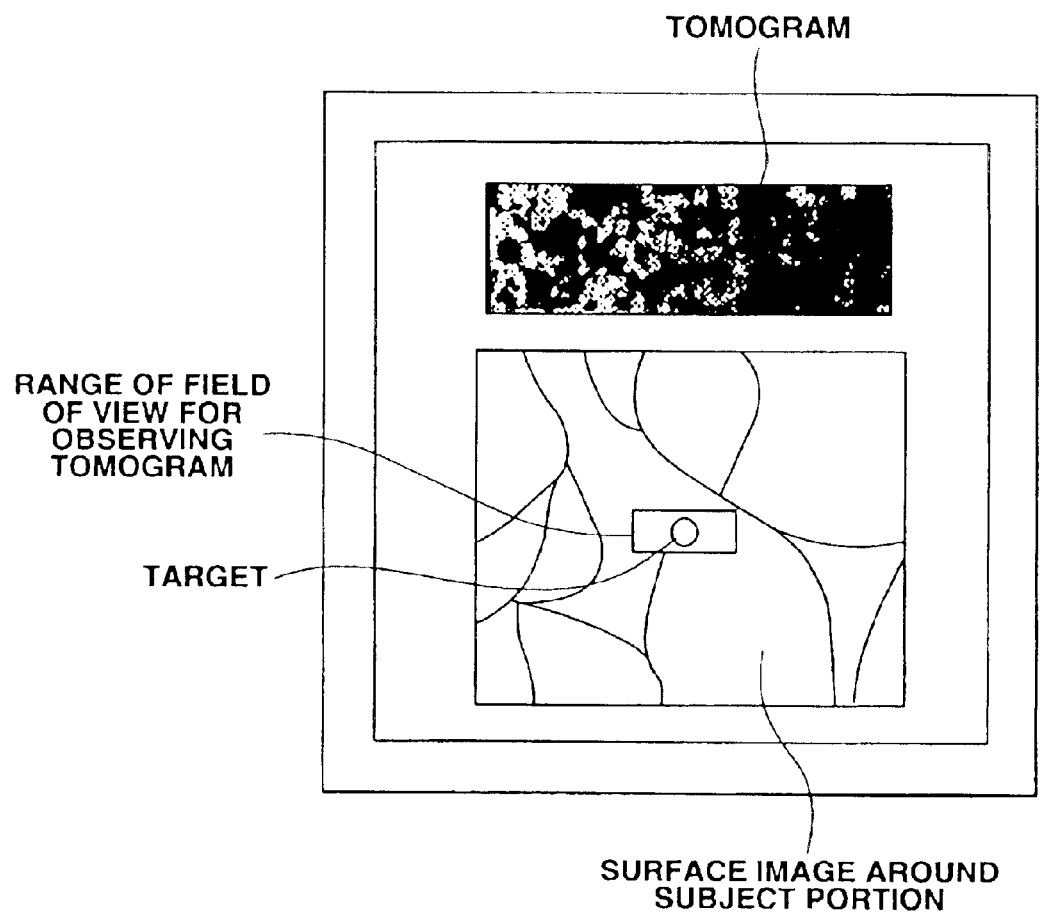
FIG. 40 is an explanatory diagram showing an image display example of a monitor after operations in the flowchart of FIG. 38.
Figure 41:
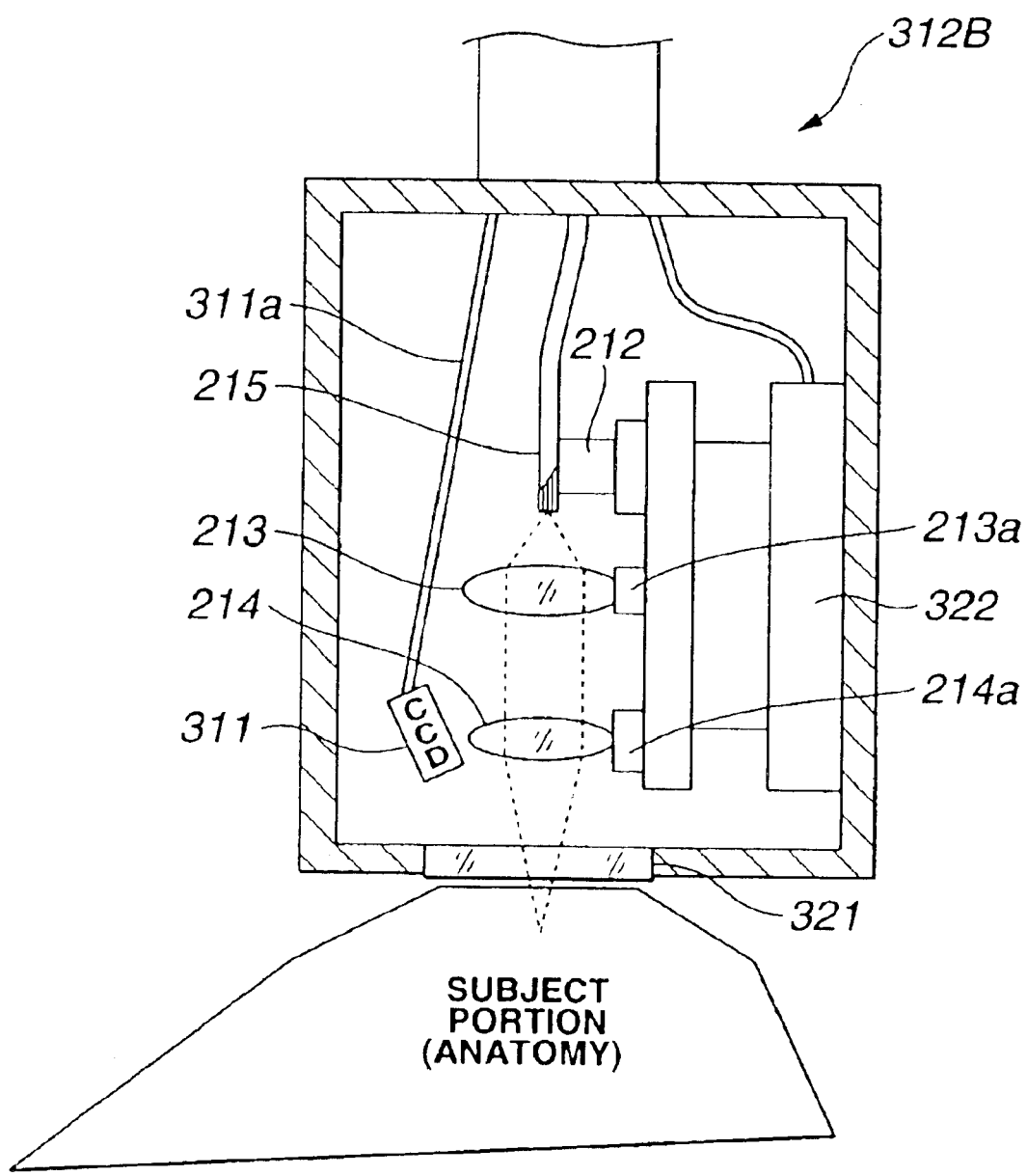
FIG. 41 is an explanatory diagram showing an optical probe according to a modification.

FIGS. 36 and 41 relate to an eighth embodiment of the present invention, FIG. 36 is a diagram showing the entire structure of an optical imaging apparatus according to an eighth embodiment of the present invention, FIG. 37 is an explanatory diagram showing an image display example of a monitor in FIG. 36, FIG. 38 is a flowchart showing processing for controlling the movement of the field of view for observation, FIG. 39 is a diagram showing coordinates for calculation in the flowchart of FIG. 38, FIG. 40 is an explanatory diagram showing an image display example of a monitor after operations in the flowchart of FIG. 38, and FIG. 41 is an explanatory diagram showing a modification of the optical probe.

According to the eighth embodiment, the optical probe comprises image pick-up means for picking up a surface image around the subject portion. Other structure is the same as that according to the fifth embodiment and a description thereof is omitted. Then, the same components are described with the same reference numerals.

Referring to FIG. 36, according to the eighth embodiment, an optical imaging apparatus 310 comprises an optical probe 312 to which a CCD 311 for surface observation is provided as an image pick-up device for picking up a surface image around the subject portion.

The optical probe 312 according to the eighth embodiment is substantially the same hand-held probe as that described according to the fifth embodiment. The positioning unit 220B described in FIG. 23, as the filed-of-view position adjusting mechanism 222B, is controlled and driven by the control unit 313 and then is electrically driven via the control cable 313b. The control unit 313 is controlled by the P.C. 314.

A wavelength separating mirror 315 on the optical path of the return light, for example, between the objective optical system 214 and the parallel lens 213 separates and returns the return light of the wavelength different from the observation light, among the reflection light and the scattering light of the subject portion captured by the objective optical system 214, thereby supplying the return light to the CCD 311 for surface observation. In other words, the wavelength separating mirror 315 allows the passage of only the return light having the same wavelength as that of the observation light, among the reflection light and scattering light of the subject portion captured by the objective optical system 214. Light having the wavelength except for the above-mentioned ones is reflected to the CCD 311 for surface observation.

The return light reflected by the wavelength separating mirror 315 is condensed by a CCD-side condensing lens 316 and is received by an image pick-up surface of the CCD 311 for surface observation.

The CCD 311 for surface observation photoelectrically converts the return light received by the image pick-up surface, generates an image pick-up signal, and outputs the signal to the control unit 313 via a signal line 311a.

The image pick-up signal is subjected to signal processing by a signal processing unit (not shown) and the control unit 313 outputs the processed signal to the P.C. 314.

The P.C. 314 generates image data corresponding to the surface image around the subject portion and outputs the generated data to the monitor 205, thereby displaying the surface image around the subject portion together with the tomogram (optical imaging picture) which will be described later (refer to FIG. 37).

Here, when the tomogram (optical imaging picture) obtained by the optical probe 312 does not represent the position of the subject portion to be desired by the user, the optical imaging apparatus 310 moves the cover glass 221 in the horizontal direction (X and Y direction) of the objective optical system 214 and adjusts the position of the objective optical system 214 in the field of view while the field-of-view position adjusting mechanism 222B of the positioning unit 220B is driven and controlled and the cover glass 221 comes into contact with the anatomy of the subject portion.

According to the eighth embodiment, as shown in a flowchart of FIG. 38 which will be described later, in the optical imaging apparatus 310, a target in the surface image around the subject portion, obtained by the CCD 311 for surface observation, is designated and the target position is adjusted at the position of the objective optical system 214 in the field of view.

The P.C. 314 performs the above-mentioned control operation. The P.C. 314 commonly functions as display processing means for displaying the range of the field of view for observation of the tomogram on the surface image around the subject portion, as target designating means for designating the target on the surface image within the range of the field of view for observation of the tomogram displayed by the display processing means, and as control means for controlling the field-of-view position adjusting mechanism 222B of the positioning unit 220B so as to match the field of view for observation of the objective optical system 214 to the designated target, obtaining the surface image and tomogram at the target, moving the field of view for observation of the tomogram, and displaying it on the surface image.

Next, the automatic adjustment of the field of view for observation will be described with reference to FIGS. 37 to 40.

First, the user operates a target setting button (not shown) of the P.C. 314. Then, referring to FIG. 37, the P.C. 314 displays a pointer for setting the target and the target on the surface image around the subject portion obtained by the CCD 311 for surface observation, which is displayed on the monitor display screen, and displays the range of the field of view of the tomogram. On the monitor display screen shown in FIGS. 37 and 40, a tomogram display area is arranged at the upper portion and a surface image display area around the subject portion is displayed at the lower portion.

The user designates and determines the desired position on the surface image around the subject portion by the pointer for setting the target via input instructing means (not shown) such as a mouse.

Then, the P.C. 314 starts processing for moving the field of view for observation shown in FIG. 38.

First, the P.C. 314 designates the target (step S1). The P.C. 314 calculates the distance from the designated target to the center of the field of view for observation of the tomogram (step S2).

Herein, referring to FIG. 39, it is assumed that the center in the field of view for observation of the tomogram is origin $(X_0, Y_0)$. Then, coordinates of the designated target are $(X_i, Y_i)$.

In this case, a distance $(\Delta X, \Delta Y)$ to the designated target $(X_i, Y_i)$ from the origin $(X_0, Y_0)$ of the field of view for observation of the tomogram is expressed by the following formulae.

$$\Delta X = X_i - X_0$$

$$\Delta Y = Y_i - Y_0$$

Incidentally, a unit is a pixel.

Next, the P.C. 314 multiplies a distance converting coefficient k ($\mu$m/pixel) to the distance $(\Delta X, \Delta Y)$ on the tomogram, thereby converting a distance $(X_L, Y_L)$ to the designated target from the center in the actual field of view. That is, the distance $(X_L, Y_L)$ is expressed by the following formulae.

$$X_L = \Delta X \times k$$

$$Y_L = \Delta Y \times k$$

Incidentally, a unit is $\mu$m.

Next, the P.C. 314 drives and controls the field-of-view position adjusting mechanism 222B (XY stage 260) of the positioning unit 220B, moves the XY base 261 by a distance ($X_L$, $Y_L$) in the horizontal direction (X and Y directions) of the objective optical system 214, and moves the cover glass 221 (step S3). The center in the field of view of the objective optical system 214 is adjusted to be overlapped to the designated target.

Then, the optical imaging apparatus 310 obtains the surface image around the subject portion at the designated target, and obtains the tomogram (optical imaging picture) at the designated target.

Referring to FIG. 40, on the display screen of the monitor 205, the surface image around the subject portion is displayed in the area for displaying the surface image at the lower portion with the designated target as center, and the tomogram is displayed in the area for displaying the tomogram at the upper portion with the designated target as center.

Further, on the display screen of the monitor 205, the range of the field of view for observation of the tomogram is displayed on the surface image around the subject portion displayed in the area for displaying the surface image at the lower portion.

As a result, the optical imaging apparatus according to the eighth embodiment can automatically adjust the position in the field of view only by designating the target, thereby easily and simply obtaining the tomogram of the target.

Referring to FIG. 41, the optical probe having the CCD 311 for surface observation may comprise movement adjusting means for automatically adjusting the movement of the field of view of the objective optical system 214 without arranging the positioning unit 220B.

Referring to FIG. 41 again, an optical probe 312B comprises the CCD 311 for surface observation whose image pick-up surface is directed to the observation window 321.

In the optical probe 312, the X/Y scanner 212 for fixing the edge side of the fiber 211, a parallel lens frame 213a, and an objective optical system frame 214a, as movement adjusting means for automatically adjusting the movement of the field of view of the objective optical system 214, are arranged to an XYZ electromotive stage 322.

The XYZ electromotive stage 322 comprises a field-of-view position adjusting mechanism for moving the X/Y scanner 212, the parallel lens frame 213a, and the objective optical system frame 214a in the horizontal direction (X and Y directions) and the vertical direction (Z direction) so as to adjust the position in the field of view of the objective optical system 214.

Similarly to the positioning unit 220B described according to the eighth embodiment, the XYZ electromotive stage 322 is controlled and driven via the control unit 313 by the P.C. 314 so that the designated target position is at the position of the objective optical system 214 in the field of view.

Thus, the optical probe 312B according to the present modification has the same advantages as those according to the eighth embodiment. In addition, the operability is improved because the field-of-view position adjusting mechanism 222B is provided in the probe.

Ninth Embodiment

Figure 42:
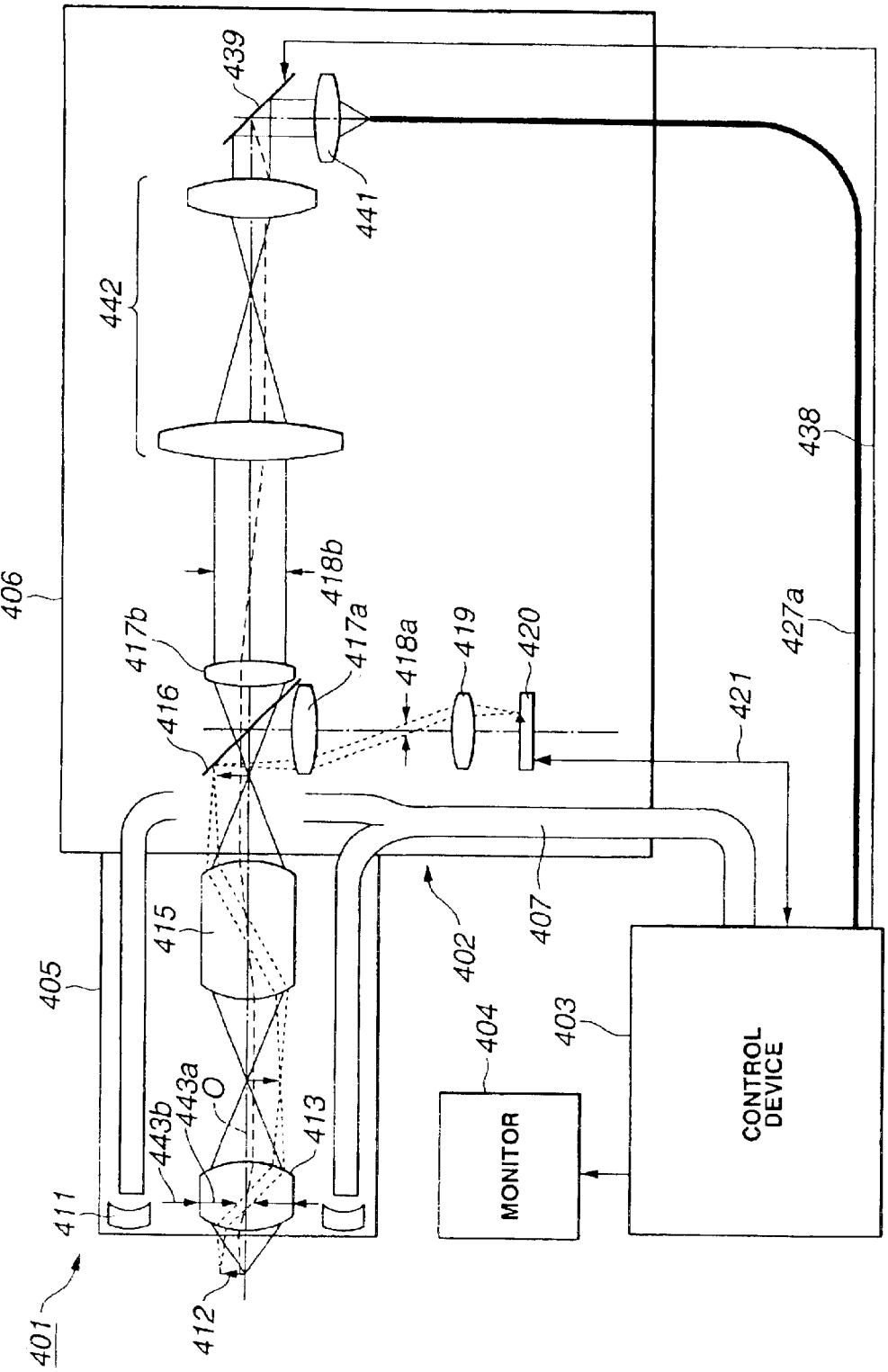
FIG. 42 is a diagram showing the entire structure of an endoscope apparatus according to a ninth embodiment of the present invention.
Figure 43:
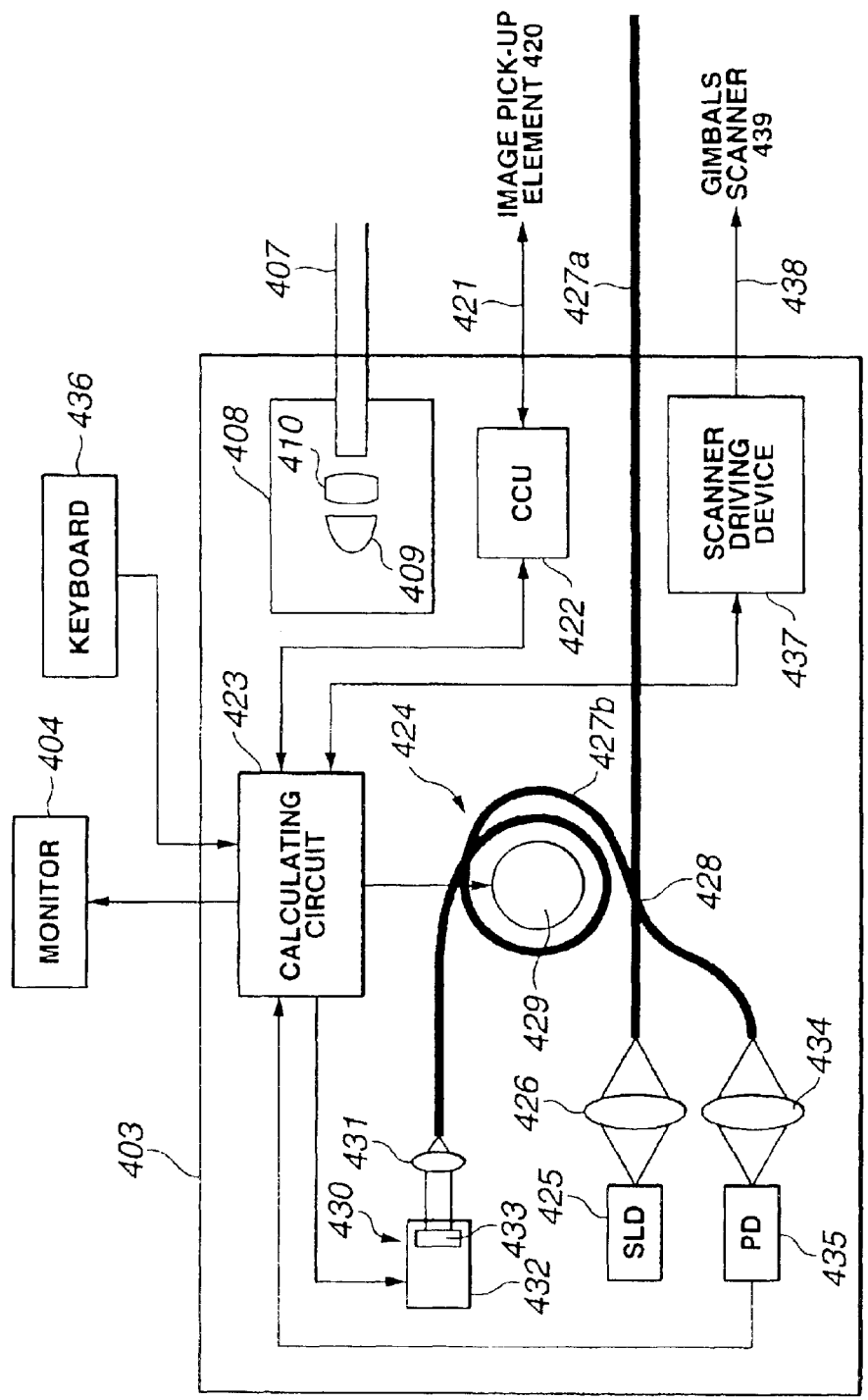
FIG. 43 is a diagram showing the internal structure of a control device.
Figure 44:
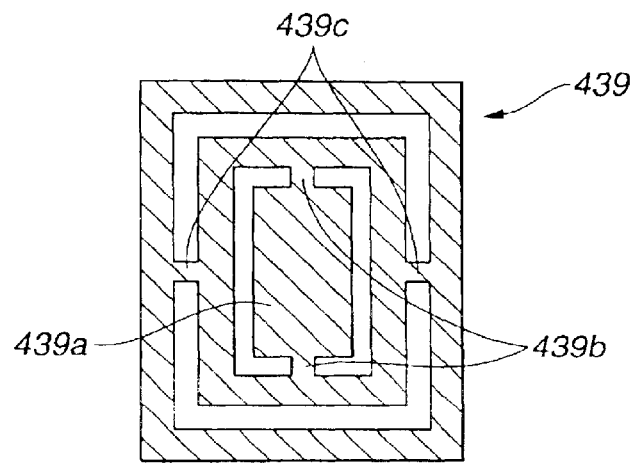
FIG. 44 is a diagram showing the structure of a gimbals mirror.
Figure 45A:
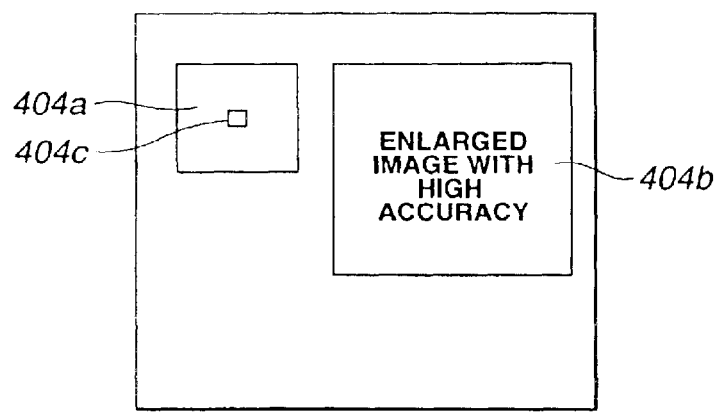
FIG. 45A is a diagram showing a display example of an endoscope image.
Figure 45B:
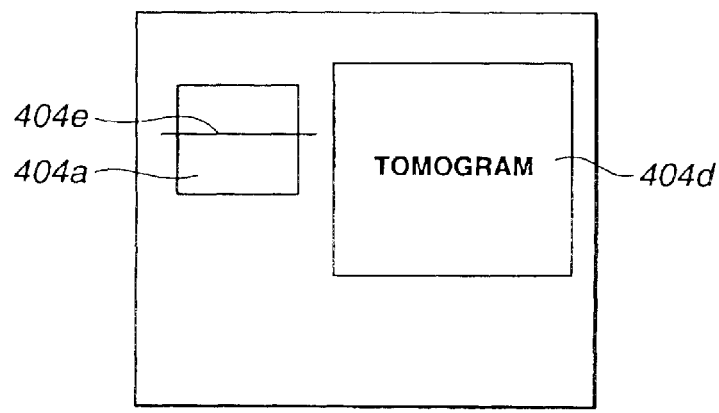
FIG. 45B is a diagram showing a display example of a tomogram.
Figure 46:
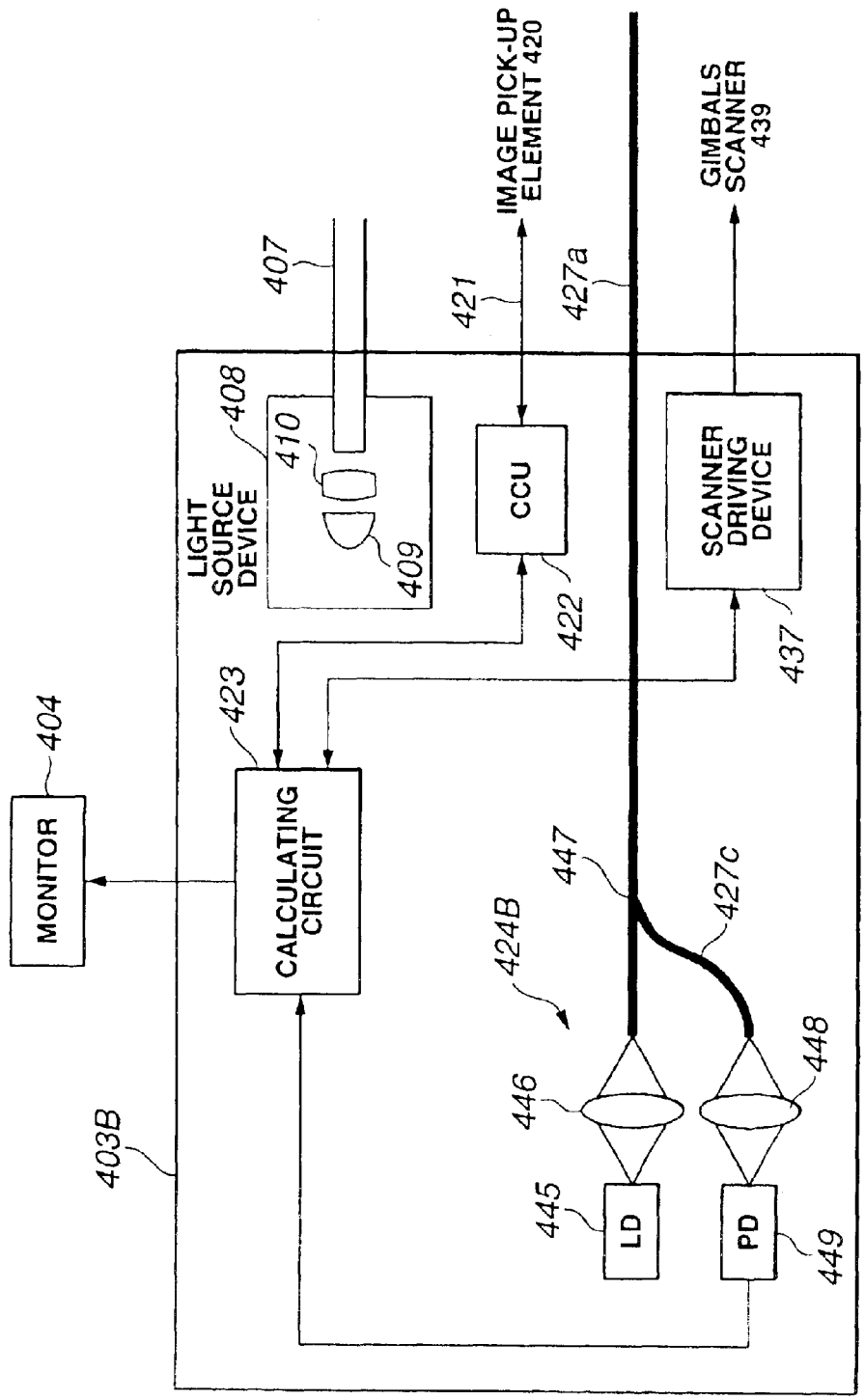
FIG. 46 is a diagram showing the internal structure of a control device according to a modification.

FIGS. 42 to 46 relate to a ninth embodiment of the present invention, FIG. 42 is a diagram showing the entire structure of an endoscope apparatus according to the ninth embodiment of the present invention, FIG. 43 is a diagram showing the internal structure of a control device, FIG. 44 is a diagram showing the structure of a gimbals mirror, FIG. 45A is a diagram showing a display example of an endoscope image, FIG. 45B is a diagram showing a display example of a tomogram, and FIG. 46 is a diagram showing the internal structure of a control device according to a modification.

Referring to FIG. 42, according to the ninth embodiment of the present invention, an endoscope apparatus 401 as an optical imaging apparatus comprises an endoscope 402 which can be inserted in the body cavity, a control device 403 connected to the endoscope 402, for supplying illumination light, etc. to the endoscope 402 and performing imaging and control operation, and a monitor 404 connected to the control device 403, for displaying the endoscope image and an enlarged image with high precision.

The endoscope 402 comprises a hard inserting portion 405 which is inserted in the body cavity and an operating unit 406 formed at the rear end of the inserting portion 405 with a thick width, which is gripped by an operator. The insertion portion 405 is structured by a hard cylindrical tube whose casing is made hard. The insertion portion 405 comprises a light guide member for transmitting the illumination light and an optical system which has a function for forming an image and transmitting the illumination light to the back side in the casing, which will be described later.

The endoscope 402 has a fiber bundle 407, as a light guide, for transmitting the illumination light (specifically, white light) for normal observation, which is inserted into the inserting portion 405 and the operating unit 406. The fiber bundle 407 is extended outside from the operating unit 406 and is connected to the control device 403 at the end thereof.

Referring to FIG. 43, the control device 403 comprises a light source device 408 which is arranged therein. The light source device 408 comprises a lamp 409 for generating the white light and a condensing lens 410 for condensing the light to the end surface of the fiber bundle 407.

The light incident on the end surface of the fiber bundle 407 is transmitted by the fiber bundle 407, and is enlarged and outputted in front, from the end surface fixed to the end portion in the inserting portion 405 via an illumination optical system 411 so as to illuminate a subject portion 412.

The fiber bundle 407 is branched into two lines and is inserted into the operating unit 406. Further, the fiber bundle 407 is branched into two lines and is inserted into the inserting portion 405. Therefore, the endoscope 402 has the two illumination optical systems 411 opposed to the two end surfaces of the fiber bundle 407. As will be described later according to other embodiment, the fiber bundle 407 may be inserted and arranged in the inserting portion 405 with a ring shape.

At the end portion of the inserting portion 405, an objective optical system 413 is arranged in the center of the two illumination optical systems 411. The light which forms an image by the objective optical system 413 is transmitted (guided) so that it is relayed at the back side by a relay optical system 415 arranged in the inserting portion 405. As shown in FIG. 42, the relay optical system 415 is one. However, the number of relay optical systems 415 may be larger depending on the length of the inserting portion 405.

The light which is transmitted by the relay optical system 415 so that the image is relayed at the back side is branched by a half mirror 416 in the operating unit 406. The light reflected by the half mirror 416 passes through a first pupil image forming optical system 417a and a first stop 418a, and further forms an image on an image pick-up element 420 via a camera image forming optical system 419.

The image formed by the image pick-up element 420 is photoelectrically converted. The photoelectrically converted electronic signal is inputted to a camera control unit (hereinafter, abbreviated to a CCU) 422 in the control device 403 shown in FIG. 43, via the signal line 421. From the electronic signal inputted to the CCU 422, the CCU 422 extracts an image signal component which is image picked up by the image pick-up element 420 by correlative double sampling. Further, colors of the image signal components are separated and the signals are subjected to processing for generating a standard video signal. Thereafter, the signals are transmitted to a calculating circuit 423.

The image signal transmitted to the calculating circuit 423 (image picked up by the image pick-up element 420) is combined to an enlarged image, which will be described later, and is outputted to the monitor 404. Referring to FIG. 45A, the monitor 404 displays an image 404a of the image pick-up element 420 as an endoscope image on the display screen.

According to the ninth embodiment, the control device 403 comprises a light source and detecting unit 424 which generates light with low coherence and detects the return light from the subject portion 412.

The light source and detecting unit 424 comprises an excessive-luminance light emitting diode (hereinafter, abbreviated to an SLD) 425 for generating the light with the low coherence. The light with the low coherence from the SLD 425 is condensed by a condensing lens 426 and is incident on one-end surface of one optical fiber 427a. The optical fiber 427a is extended outside from the control device 403 and the other end thereof is fixed in the operating unit 406 of the endoscope 402.

The optical fiber 427a is optically coupled to another optical fiber 427b by a fiber coupler 428 in the middle of the control device 403. Therefore, the light with the low coherence from the SLD 425, incident on the optical fiber 427a, is transmitted to the other end surface of the optical fiber 427a on the operating unit 406 side and is optically coupled by a fiber coupler unit 428. Further, the light with the low coherence is branched on the optical fiber 427b which forms the optical path on the reference light side. The light branched on the optical fiber 427b side is modulated by a fiber modulator 429 which is formed by a piezo element in the middle.

The fiber modulator 429 is driven by the calculating circuit 423, thereby modulating the light guided by the optical fiber 427b. The length of the optical path formed of the optical fiber 427a from the fiber coupler unit 428 and the operating unit 406 becomes the length of the optical path on the measurement side.

The light transmitted by the optical fiber 427b via the fiber modulator 429 is shaped to parallel beams by a collimator lens 431 arranged opposed to one-end surface of the optical fiber 427b. The parallel beams are incident on a mirror 433 arranged to a stage 432, and are reflected by the mirror 433. The mirror 433 and stage 432, and the collimator lens 431 form a mechanism 430 for adjusting the length of the optical path on the reference light side.

The light reflected by the mirror 433 passes through the fiber modulator 429 and is mixed to the return light on the optical fiber 427a by the fiber coupler unit 428. In this case, if the difference between the length of the optical path on the reference light side and the length of the optical path on the measurement side is within the length of coherence of the light with the low coherence generated by the SLD 425, the mixed light becomes the coherence light. If it is not shorter than the length of the coherence of the light with the low coherence, the mixed light is not coherent.

The light mixed by the fiber coupler unit 428 is condensed by the condensing lens 434 from the other-end surface of the optical fiber 427b, and is received by an optical detector (abbreviated to a PD in FIG. 43 or the like) 435.

As mentioned above, the optical fiber 427b is optically coupled to the other optical fiber 427a by the fiber coupler unit 428 in the middle. Therefore, the reflection light in the mechanism 430 for adjusting the length of the optical path on the reference light side is mixed to the return light received by the other-end surface of the optical fiber 427a in the fiber coupler unit 428. That is, the length of the optical path from the fiber coupler unit 428 to the mechanism 430 for adjusting the length of the optical path on the reference light becomes the length of the optical path on the reference side. When the difference between the length of the optical path on the reference side and the length of the optical path on the measurement side is within the length of coherence of the light with low coherence, the optical detector 435 detects the coherent light.

Therefore, a detecting unit in the light source and detecting unit 424 has a function as an interferometer.

The signal photoelectrically converted by the optical detector 435 is inputted to the calculating circuit 423. The calculating circuit 423 demodulates the signal detected by the optical detector 435, and extracts a coherent light component.

The calculating circuit 423 sends a control signal to the stage 432 by an instructing operation from a front panel of the control device 403, a keyboard 436 connected to the control device 403, or the like. The stage 432 is moved as shown by an arrow A, the position of the mirror 433 is changed, and the length of the optical path on the reference side can be changed.

The control device 403 comprises a scanner driving device 437 therein. The scanner driving device 437 drives a gimbals scanner 439 shown in FIG. 42 via a signal line 438. The scanner driving device 437 is connected to the calculating circuit 423.

The calculating circuit 423 demodulates and extracts a signal having the coherence light component from the signals transmitted from the optical detector 435, and A/D converts the signals. Further, the calculating circuit 423 stores data in an internal memory in association with the optical scanning of the scanner driving device 437, thereby generating two-dimensional image data of the tomogram with the low-coherence light.

Referring to FIG. 42, a collimator optical system 441 is arranged opposed to the fixed end surface of the optical fiber 427a in the operating unit 406. The light outputted from the end surface of the optical fiber 427a is made parallel beams by the collimator optical system 441. The parallel beams are inputted to the gimbals scanner 439 as a two-dimensional scanner which is driven by the scanner driving device 437. The gimbals scanner 439 has a mirror surface with an angle of 45° to the optical axis of the collimator optical system 441.

FIG. 44 shows the schematic structure of the gimbals scanner 439.

The gimbals scanner 439 holds a mirror surface 439a in the center thereof tiltablly in the horizontal direction by a first hinge portion 439b and holds the mirror surface 439a tiltablly in the vertical direction outside the first hinge portion 439b by a second hinge portion 439c perpendicular to the holding direction of the first hinge portion 439b. The gimbals scanner 439 two-dimensionally tilts the mirror surface 439a based on the scanner drive signal from the scanner driving device by a magnetically or electrostatically driving mechanism, thereby two-dimensionally scanning the light incident from the collimator optical system 441.

Referring to FIG. 42, the light reflected by the gimbals scanner 439 is converted into parallel beams with a larger diameter of the laser beams by a pupil diameter converting optical system 442 formed of a pair of convex lenses. The pupil diameter converting optical system 442 enlarges the diameter of the laser beams and can use the gimbals scanner 439 with a small size.

The parallel beams are condensed by a second pupil image forming optical system 417b via a second stop 418b. A part of the condensed light is transmitted by the half mirror 416 and is incident on the relay optical system 415. Then, the light is further incident on the objective optical system 413 via the relay optical system 415. The incident light is condensed by the objective optical system 413 and is condensed and irradiated to the subject portion 412.

The reflection light from the subject portion 412 is guided to the end surface of the optical fiber 427a via a route contrary the above described one. The return light from the subject portion 412, transmitted from the optical fiber 427a, is partly branched on the optical fiber 427b side by the fiber coupler unit 428, and is received by the optical detector 435.

According to the ninth embodiment, as shown in FIG. 42, the endoscope 402 comprises illuminating means for normally illuminating the inserting portion 405 (such as the fiber bundle 407 and the illumination optical system 411), the objective optical system 413 for forming the image of the subject portion 412 illuminated by the illuminating means, and the relay optical system 415 for transmitting the optical image to the rear operating unit 406.

The structures of the objective optical system 413 and the relay optical system 415 have a similar structure as that of the normal optical endoscope. However, the operating unit 406 comprises branching means for branching the light into the reflection light side and the transmission light side by the half mirror 416. The endoscope 402 has a low-coherence light side optical system for guiding the light to the image pick-up means for picking up the image for normal observation on the reflection light side, guiding the low-coherence light to the subject portion 412 and guiding the return light from the subject portion 412 to (the detector 435 which functions as an interferometer) on the transmission light side, by using the branching means.

The endoscope 402 obtains image information for normal observation and enlarged image information obtained by (scanning) the low-coherence light by using the branching means.

According to the ninth embodiment, the endoscope 402 commonly uses the objective optical system 413 and the relay optical system 415 which are arranged in the inserting portion 405, both for normal observation (macro observation) and for enlarged observation (micro observation) with the low-coherence light, thus making the inserting portion 405 thinner in diameter.

Further, according to the ninth embodiment, the endoscope 402 comprises the first pupil image forming optical system 417a and the first stop 418a with a smaller stop diameter and the second pupil image forming optical system 417b and the second stop 418b with a larger stop diameter, on the optical paths branched by the half mirror 416 in the operating unit 406. An image 443a of the first stop 418a and an image 443b of the second stop 418b are formed to the pupil position of the objective optical system 413.

In other words, in FIG. 42, the image (opening image) 443a of the first stop 418a becomes an opening image with a small size on an optical axis O as shown by a dotted line. On the contrary, the image (opening image) 443b of the second stop 418b becomes the opening image with a larger size on the optical axis O as shown by a solid line.

The numerical aperture (hereinafter, abbreviated to an NA) of the objective optical system 413 is made substantially small so that the image pick-up element 420 for normal observation functions with only light which passes through the opening portion of the image 443a of the first stop 418a and forms the image. On the other hand, the image pick-up element 420 for low-coherence light functions with the NA of the objective optical system 413 with high resolution so as to condense light which passes through the large opening portion of the image 443b of the second stop 418b.

According to the ninth embodiment, in the case of the low-coherence light, the endoscope 402 has the high resolution caused by the increased NA so as to enlargedly observe a small area in the center of the range for normal observation.

A long dotted line in FIG. 42 indicates a chief ray out of the optical axis in the case of using the low-coherence light. In this case, the observation range of the subject 412 becomes a small range indicated by the optical axis O shown by an alternate long and short dash line and the chief ray (shown by a long dotted line). The gimbals scanner 439 scans the image in the vertical direction of the sheet of FIG. 42 and, therefore, the image can be observed in the vertical direction of the sheet with the small size.

The control device 403 generates image data by using a large number of intensity data of the coherent light component in accordance with the scanning of the gimbals scanner 439, thereby forming the image with high resolution and high accuracy.

In the endoscope 402, the NA of the observation optical system 413 is substantially small for the normal observation, so that the image can be formed to the image pick-up element 420 to obtain a preferable image which is easily observed, without darkening the periphery of the field of view (due to eclipse).

Referring to FIG. 45A, the monitor 404 displays on the display screen the normal image (macro image) 404a captured by the image pick-up element 420 adjacent to the enlarged image 404b (with high accuracy) formed by the low-coherence light. In this case, the monitor 404 displays an observation range 404c of the enlarged image 404b when using the low-coherence light for the center in the normal image so that the observation range 404c of the enlarged image 404b can easily be understood from the normal image 404a.

The gimbals scanner 439 is one-dimensionally driven in the horizontal direction. In this case, in the endoscope 402, the image is scanned synchronously with the stage 432 of the mechanism 430 for adjusting the length of the optical path on the reference light side, thereby obtaining the tomogram in the case of scanning the image in the depth direction of the subject portion 412.

Referring to FIG. 45B, the monitor 404 displays on the display screen a tomogram 404d near the normal image 404a. In this case, the monitor 404 displays on the display screen, a line 4e indicating the cross-sectional position on the tomogram 404d on the normal image 404a side. Incidentally, in the endoscope 402, the gimbals scanner 439 is driven not in the horizontal direction but one-dimensionally in the vertical direction. Synchronously with the driving operation, the stage 432 is scanned, thereby obtaining the tomogram in the case of the scanning the subject portion 412 along a surface in the longitudinal direction in the depth direction of the subject portion 412.

With the above-mentioned structure, the operation according to the ninth embodiment will be described later.

When turning on the power source of the control device 403, the subject portion 412 is illuminated with illumination light generated by the light source 408. An optical image of the illuminated subject portion 412 is formed by the objective optical system 412 which functions as a small NA. The optical image is transmitted to the back side by the relay optical system 415.

The optical image is reflected by the half mirror 416 and is formed to the image pick-up element 420 via the pupil image forming optical system 417, the stop 418a, and the camera image forming optical system 419. The formed image is photoelectrically converted. An output signal from the image pick-up element 420 is converted into a video signal by the CCU 422, and is outputted to the monitor 404 via the calculating circuit 423. Referring to FIGS. 45A and 45B, as mentioned above, the monitor 404 displays on the display screen, the normal image 404a, as the macro image, which is picked up by the image pick-up element 420.

On the other hand, the low-coherence light from the SLD 425 is condensed and is incident on the optical fiber 427a. The light is partly branched to the optical fiber 427b by the fiber coupler unit 428, and the light is reciprocated on the optical path on the reference light side.

The light guided to the end of the optical fiber 427a by it is outputted from the end surface of the operating unit 406, and is made parallel beams by the collimator optical system 441. Then, the parallel beams are incident on the gimbals scanner 439. The gimbals scanner 439 is two-dimensionally tilted by the scanner driving device 437, and the reflection light is two-dimensionally scanned.

The reflection light by the gimbals scanner 439 passes through the pupil diameter converting optical system 442 and the diameter of the beam is enlarged. Then, the light passes through the second stop 418b and is guided to the relay optical system 415 side with a large diameter of the beam via the pupil image forming optical system 417b and the half mirror 416. The guided light passes through the relay optical system 415 and is condensed and irradiated to the subject portion 412 by the objective optical system 413 so that almost the outer diameter of the objective optical system 413 corresponds to the opening.

The reflection light on the subject portion 412 passes through the contrary optical path, and is condensed and incident on the edge surface of the optical fiber 427a. The optical detector 435 receives the coherent light within the length of optical path on the reference light side and the length of coherence of the low-coherence light in the fiber coupler unit 428.

The signal photoelectrically converted by the optical detector 435 is inputted to the calculating circuit 423. The calculating circuit 423 demodulates the signal so that the light is two-dimensionally scanned and the coherent light component modulated by the fiber modulator 429 is extracted, and converts the demodulated signal into digital data by an A/D converter. Then, the calculating circuit 423 stores the signal inputted on time series, in the memory, and generates two-dimensional image data.

The image data is read as an analog video signal by the D/A converter, and is outputted to the monitor 404 together with a video signal inputted from the CCU 422. The monitor 404 displays on the display screen the enlarged image 404b with high accuracy together with the normal image 404a obtained by the image pick-up element 420, as shown in FIG. 45A.

Here, the user inputs an instruction for changing the scanning by the keyboard 436. Then, the scanner driving device 437 one-dimensionally generates a drive signal. The drive signal is transmitted by the signal line 438. The scanner 439 is one-dimensionally driven. Further, the calculating circuit 423 reciprocates the stage 432 synchronously with the scanner 439, thereby forming the tomogram by the signal from the optical detector 435.

In this case, referring to FIG. 45B, the monitor 404 displays on the display screen the tomogram 404d together with the normal image 404a captured by the image pick-up element 420.

According to the ninth embodiment, the endoscope apparatus 401 as the optical imaging apparatus can observe the normal image of the subject portion 412 within the wide range as the normal endoscope image, and the image within the narrow area in the center of the normal image by the enlarged image using the low-coherence light with the high resolution.

Next, according to the ninth embodiment, the typical NA will be described. The following formula (1) represents the relationship of the resolution of the objective optical system 413.

$$r=0.56\lambda/NA \qquad (1)$$

Herein, reference numeral r indicates a resolution length and reference numeral $\lambda$ indicates the wavelength of the using light.

Considering the case of picking up the macro image by the image pick-up element 420 having the 500×500 pixels in square of 2 mm, one pixel has the length of 4 $\mu$m. In this case, the length of 2 $\mu$m as half of 4 $\mu$m may be resolved by the sampling principle with the resolution of the objective optical system 413. A wavelength $\lambda$ is set to that of 0.5 $\mu$m around the center of the white light.

In this case, the formula (1) is as follows.

$$2=0.56\times0.5/NA$$

That is, the NA is equal to 0.14.

On the other hand, in the case of the micro image, it is assumed that the resolution of the objective optical system 413 needs at least approximately 1 $\mu$m as the resolution length r. Then, the formula (1) is as follows.

$$1=0.56\times0.8/NA$$

Herein, it is assumed that the wavelength $\lambda$ is 0.8 $\mu$m as the wavelength near infrared light.

In this case, the NA is equal to 0.448 or more.

Therefore, the NA in the micro image is 0.448/0.14≈3 in the macro image. That is, the NA in the micro image is three times or more of that of the macro image.

According to the ninth embodiment, the endoscope apparatus 401 as the optical imaging apparatus displays the enlarged micro image with the low-coherence light within the narrow area in the center of the macro image. Therefore, the endoscope apparatus 401 can perform normal endoscope diagnosis with the macro image and can enlarge and display the micro image in the center with the high resolution as high NA. Thus, the endoscope apparatus 401 can provide an environment in which the detailed diagnosis at the cell level can easily be executed.

In this case, the endoscope apparatus 401 observes the image by using the common objective optical system 413 having substantially different NAs in the macro image and the micro image. Therefore, the position where the micro image in the macro image is observed is not changed within a predetermined range in the center, and the positioning in the case of the observation using the micro image becomes easy.

According to the ninth embodiment, in the endoscope 402, similarly to the normal endoscope, the objective optical system 413 and the relay optical system 415 are inserted into the inserting portion 405, and the optical system is commonly used even in the case of the low-coherence light. Therefore, the inserting portion 405 can be thinner in diameter.

Thus, in the endoscope 402, the inserting portion 405 having a small inserting hole according to the ninth embodiment can be inserted and, consequently, affliction to a patient can be reduced.

Although the above description uses the low-coherence light, the ninth embodiment can be applied to the case of using the conjugate focusing optical system.

FIG. 46 shows the structure of a control device 403B in the case of using the conjugate focusing optical system. In this case, the endoscope 402 has the same structure as that in FIG. 42.

In this case, in place of the light source and detecting unit 424 in FIG. 43, the control device 403B uses a light source and detecting unit 424B with a more simple structure. Light from the laser diode 45 as a light source is condensed by the condensing lens 46 and is incident on the one end of the optical fiber 427a. The light is transmitted by the optical fiber 427a and is outputted from another-end surface (edge surface) of the operating unit 406 shown in FIG. 42.

In this case, the size of the edge surface of the optical fiber 427a is sufficiently small and has a function equivalent to a pin hole. The light outputted from the end surface (edge surface) of the optical fiber 427a passes through the gimbals scanner 439 and the like as mentioned above and is condensed and irradiated to the subject portion 412 from the objective optical system 413 with a high NA.

The reflection light on the subject portion 412 only from the focus position of the objective optical system 413 traces the contrary optical path, and is incident on the edge surface of the optical fiber 427a. On the contrary, the reflection light from the portion excluding the focus point of the objective optical system 413 has components which pass through the objective optical system 413 and are returned. These components reach the periphery of the optical fiber 427a but are not incident on the small edge surface of the optical fiber 427a.

That is, the edge surface of the optical fiber 427a and the focus point of the objective optical system 413 has a conjugate relationship via the optical system therebetween. Light from the portion except for that having the conjugate relationship is excluded.

The return light incident on the optical fiber 427a is guided to the other optical fiber 427c by a fiber circulator unit 447 arranged to the light source and detecting unit 424B, and is received by the optical detector 449 via the condensing lens 448.

The signal photoelectrically converted by the optical detector 449 is inputted to the calculating circuit 423. The calculating circuit 423 performs almost the same processing, excluding the demodulating processing by the calculating circuit 423 in FIG. 43. The processed signal is combined to the image which is picked up by the image pickup element 420 under the operation of the CCU 422, and the normal image 404a and the enlarged image 404b with high accuracy are displayed on the display screen of the monitor 404, as shown in FIG. 45A.

The present modification has almost the same advantages as those according to the ninth embodiment.

Tenth Embodiment

Figure 47:
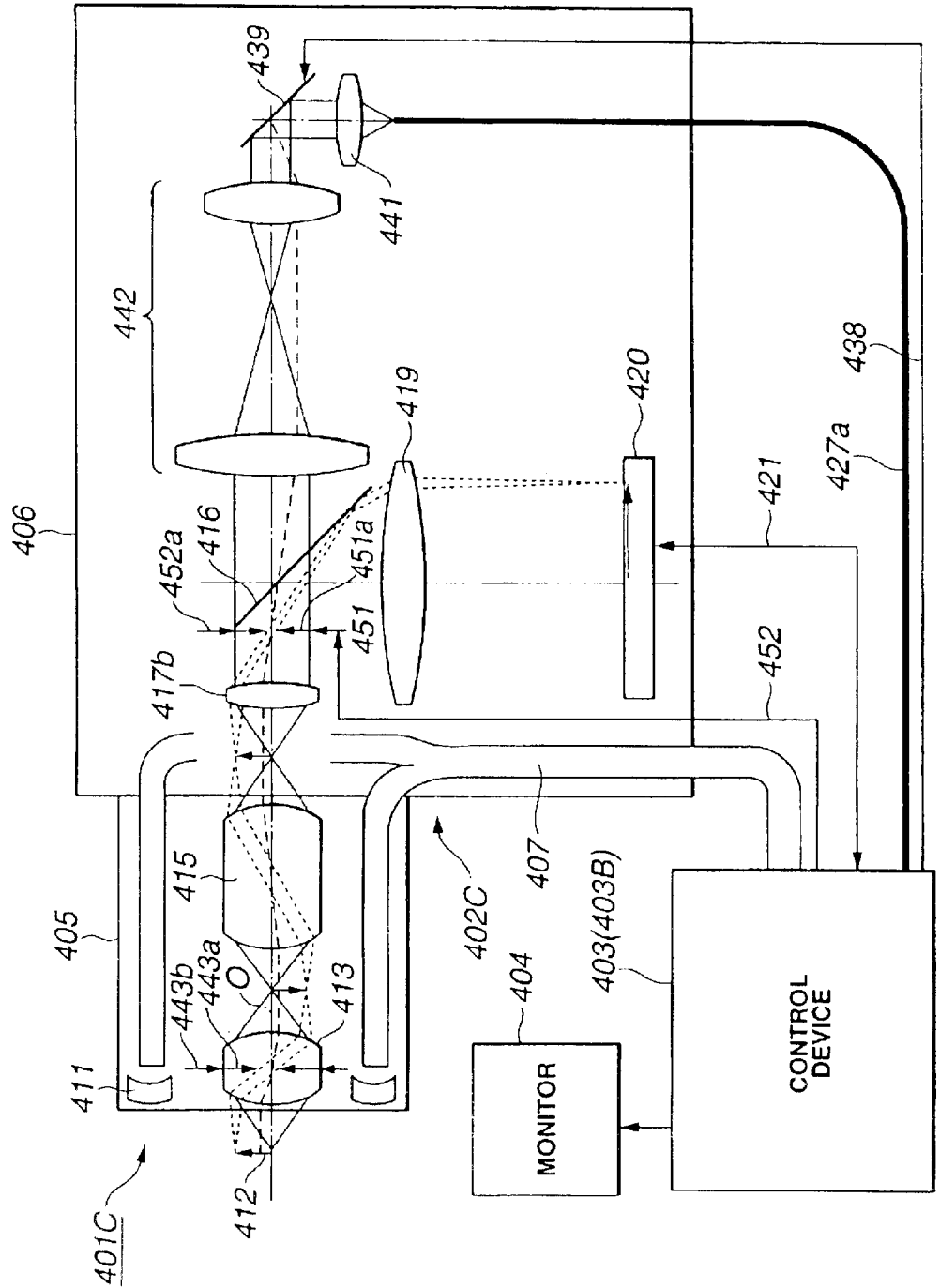
FIG. 47 is a diagram showing the entire structure of an endoscope apparatus according to a tenth embodiment of the present invention.

Next, a tenth embodiment of the present invention will be described with reference to FIG. 47. FIG. 47 shows an endoscope apparatus 401C according to the tenth embodiment of the present invention. The endoscope apparatus 401C comprises an endoscope 402C, the control device 403 (or 403B), and the monitor 404.

The endoscope apparatus 402C shown in FIG. 47 has an insertion portion having the same structure as that of the inserting portion 405 in the endoscope 402 in FIG. 42 but has a partly different optical system in the operating unit 406 from that in FIG. 42.

Specifically, the endoscope 402 according to the ninth embodiment has the pupil image forming optical systems 417a and 417b and the two stops 418a and 418b on the two branched optical paths, behind the half mirror 416. However, according to the tenth embodiment, the endoscope 402C has the pupil image forming optical system 417 and a variable stop 451 on a common optical path in front of the branched point (on the relay optical system 415 side).

The variable stop 451 is connected to, for example, the calculating circuit 423 in the control device 403 or 403B by the signal line 452, and varies a stop diameter via the calculating circuit 423. Normally, the variable stop 451 is set with a small stop diameter 451a. In this state, the monitor 404 displays on the display screen the normal image which is picked up by the image pick-up element 420. When an operation for instructing the switching is performed by the keyboard 436 shown in FIG. 43 or the like, the variable stop 451 is set with a large stop diameter 451b. In addition to the switching, the calculating circuit 423 allows the monitor 404 to display on the display screen the display image formed by the signal received by the optical detector 435 or 449, that is, the enlarged image (or tomogram) with the low-coherence light or the enlarged image formed by the conjugate focusing optical system.

Other structure is the same as that according to the ninth embodiment. According to the tenth embodiment, the variable stop 451 is normally set with the small stop diameter 451a and the same observation as that of the normal endoscope can be performed. By setting the portion to be enlarged and observed to the center in the field of view for observation and performing the operation for instructing the switching, the calculating circuit 423 sets the variable stop 451 with the large stop diameter 451b and the enlarged image (or tomogram) with the low-coherence light or the enlarged image formed by the conjugate focusing optical system is displayed on the display screen of the monitor 404.

According to the tenth embodiment, since the endoscope 402C more frequently uses the portion of the common optical system according to the ninth embodiment, the entire optical system can be reduced in size. Except for this structure, the same advantages are obtained.

Incidentally, the variable stop 451 may change the size of the stop diameter depending on the resolution, the observation range, etc.

Specifically, when the enlarged image (or tomogram) with the low-coherence light is observed or the image is enlargedly observed by the conjugate focusing optical system in the endoscope 402C, the maximum resolution is determined by the maximum NA. However, when observing a wider range than the observation range in this case, the NA of the variable stop 451 is decreased via the signal line 452 by an instructing operation of the keyboard in the endoscope 402C and the two-dimensionally scanning range of the gimbals scanner 439 is wider and the wider range can be observed. In this case, in the endoscope 402C, the periphery of the observation range may be observed with the same brightness as that on the center side by decreasing the NA.

Eleventh Embodiment

Figure 48:
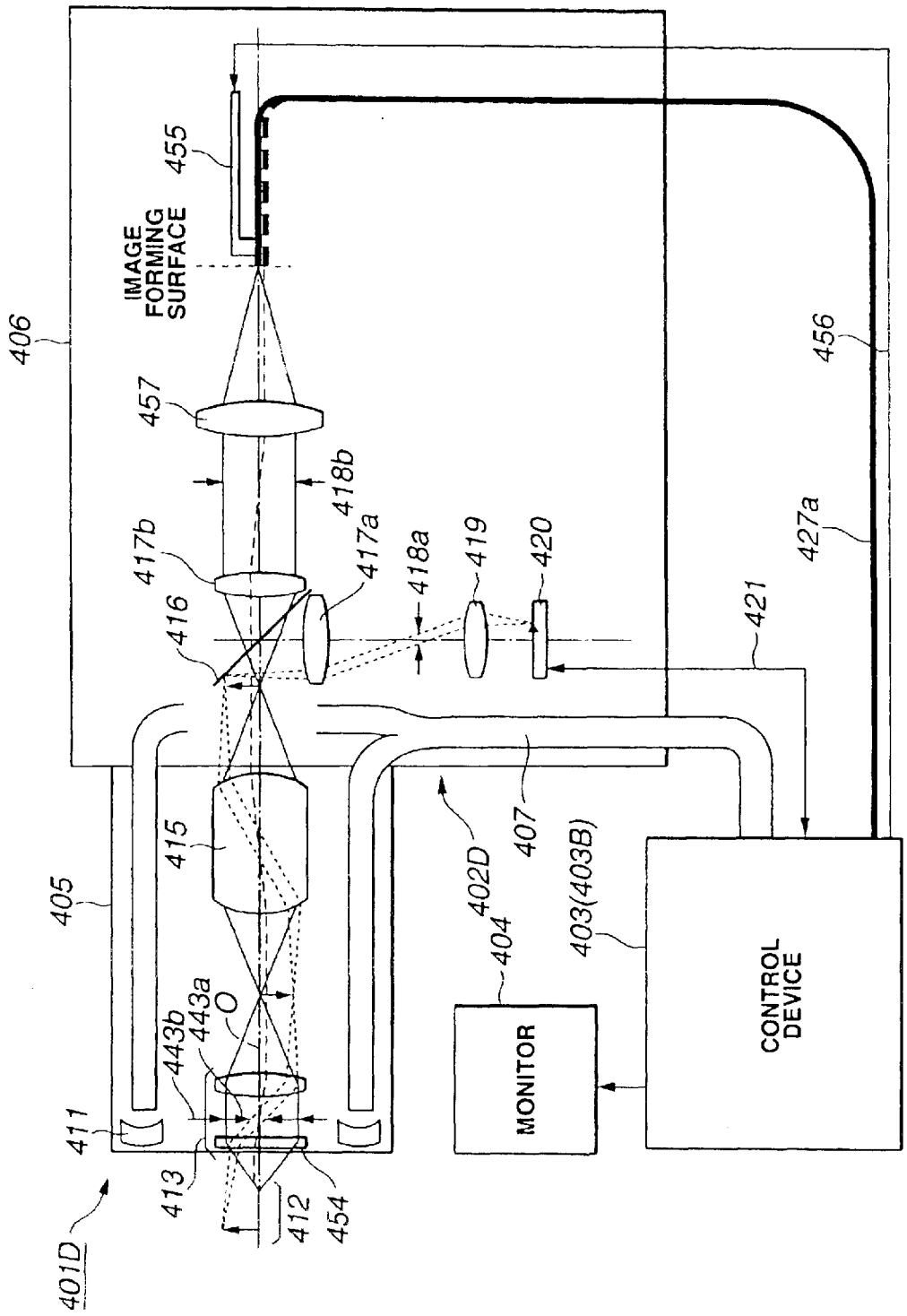
FIG. 48 is a diagram showing the entire structure of an endoscope apparatus according to an eleventh embodiment of the present invention.

Next, an eleventh embodiment of the present invention will be described with reference to FIGS. 48 and 49. FIG. 48 shows an endoscope apparatus 401D according to the eleventh embodiment of the present invention. The endoscope apparatus 401D comprises an endoscope 402D, the control device 403 (or 403B), and the monitor 404.

The endoscope 402D shown in FIG. 48 has a double focusing lens 454 as the objective optical system 413 in the endoscope 402 in FIG. 42.

According to the eleventh embodiment, the endoscope 402D has the edge surface of the optical fiber 427a, that is, outputs the light, holds the position as the image forming surface by a two-dimensional scanner composed of a piezo element 455. Further, in the endoscope 402D, the piezo element 455 is driven via the signal line 456 by the scanner driving device 437 as shown by a solid line and a thick and long dotted line in FIG. 48. Incidentally, the endoscope 402D can drive the piezo element 455 in the vertical direction of the sheet in FIG. 48.

Referring to FIG. 48, the light from the edge surface of the optical fiber 427a passes through the image forming optical system 457, the second stop 418b, and the second pupil image forming optical system 417b, and is guided to the relay optical system 415 in front of the half mirror 416.

Figure 49:
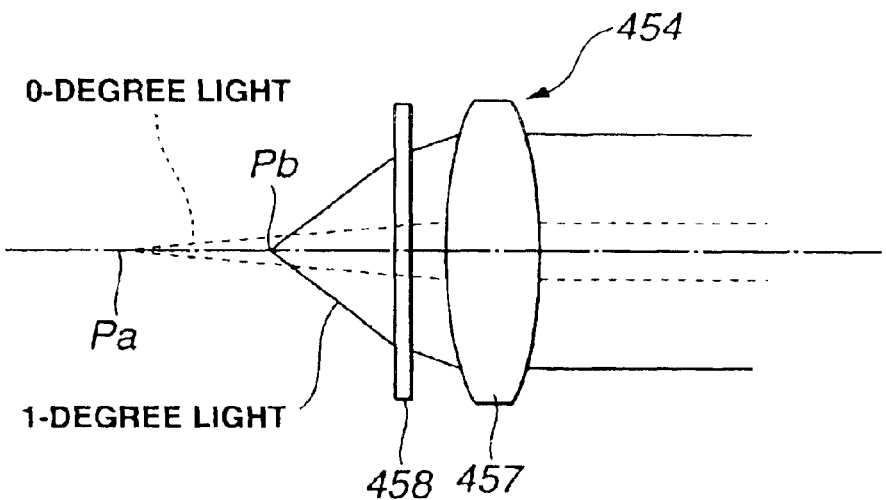
FIG. 49 is a diagram showing an example of the structure of a double focusing lens.

FIG. 49 shows an example of the structure of the double focusing lens 454. For example, a front lens in the objective optical system 413 shown in FIG. 48 comprises a convex lens 457 and a diffracting lens 458 arranged in front of the convex lens 457.

The diffracting lens 458 has convex and concave portions concentrically. In the diffracting lens 458, zero-degree light is used for the normal observation light, the light is focused at a focus position Pa, and the objective optical system 413 functions to have a long focusing distance. The diffracting lens 458 uses one-degree diffracting light for the low-coherence light or the light on the conjugate focusing optical system, and focuses the light at a focus position Pb, and the objective optical system 413 functions to have a short focusing distance.

In a typical case, the diffracting lens 458 uses the one-degree diffracting light and sets the focusing distance in the case of focusing the light at the focus position Pa to be three times of that in the case of the focusing the light at the focus position Pb (by the request of the same resolution, etc. as those described according to the ninth embodiment). Other structure is the same as that according to the ninth embodiment.

According to the eleventh embodiment, in the normal observation, the endoscope 402D functions as the objective optical system 413 having the long focusing distance and the small NA. In the observation with the low-coherence light or the conjugate focusing optical system, the endoscope 402D functions as the objective optical system 413 having the short focusing distance and high resolution of the high NA.

According to the eleventh embodiment, in the endoscope 402D, the distance for observing the subject portion 412 is different in the normal observation and the observation with the low-coherence light or the conjugate focusing optical system.

However, according to the eleventh embodiment, in the normal observation, the endoscope 402D has the long focusing distance and is non-telecentric. Therefore, as compared with that according to the ninth embodiment, the endoscope 402D can easily observe a wider range. In the endoscope 402D, when a part of the wide observation range is enlargedly observed in detail, the micro image can enlargedly be displayed with the low-coherence light or the conjugate focusing optical system, and an environment which facilitates the diagnosis in detail at the cell level can be provided.

According to the eleventh embodiment, the endoscope 402D uses the inserting portion 405 commonly in the normal observation and in the observation with the low-coherence light pr the conjugate focusing optical system. Therefore, the inserting portion 405 can be thinner in diameter.

Twelfth Embodiment

Figure 50:
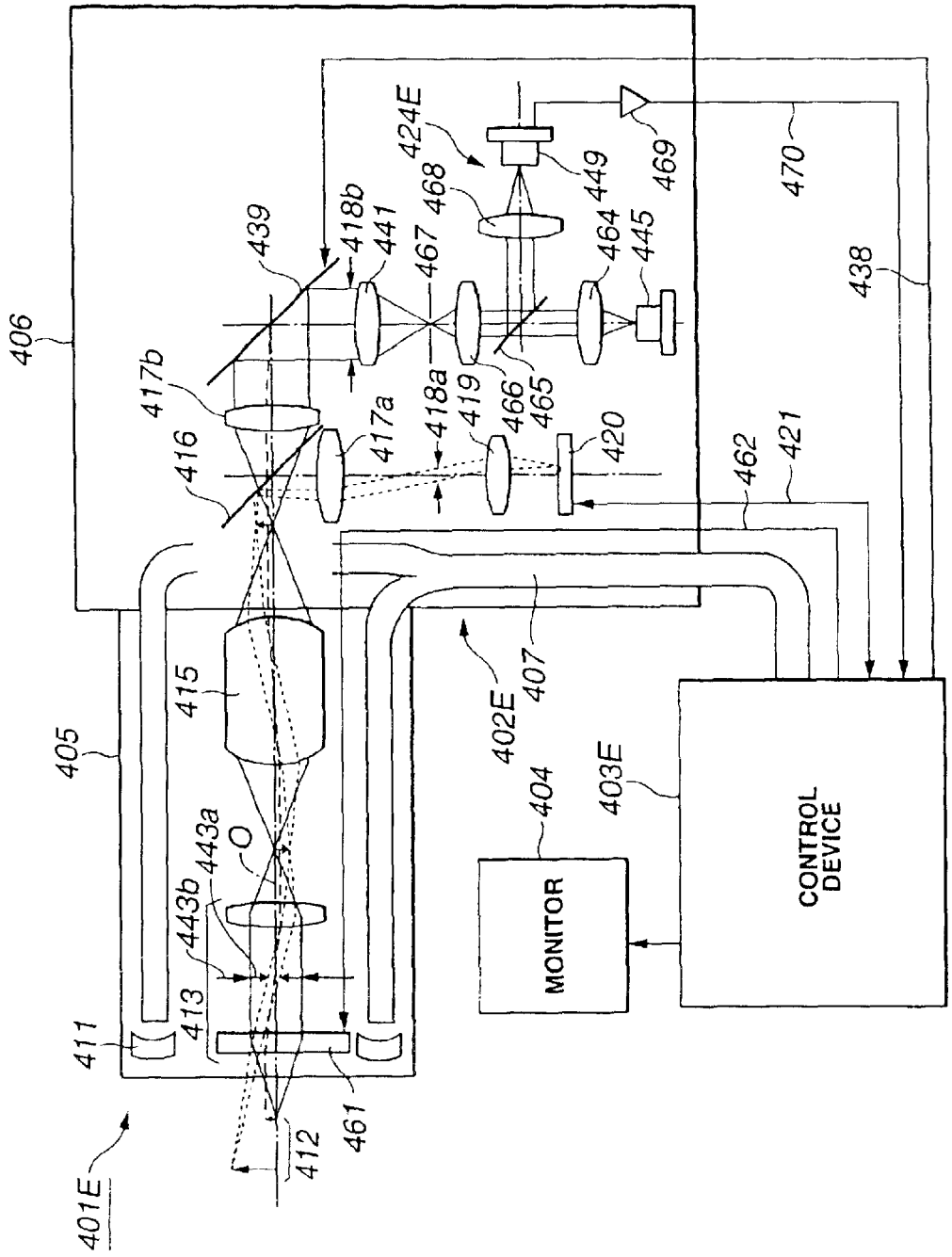
FIG. 50 is a diagram showing the entire structure of an endoscope apparatus according to a twelfth embodiment of the present invention.

Next, a twelfth embodiment of the present invention will be described with reference to FIG. 50. FIG. 50 shows an endoscope apparatus 401E according to the twelfth embodiment of the present invention. The endoscope apparatus 401E comprises an endoscope 402E, a control device 403E, and the monitor 404.

Referring to FIG. 50, the endoscope 402E change the focusing distance by changing a refraction index of a liquid crystal lens 461 as a front lens of the objective optical system 413 in the endoscope 402. The liquid crystal lens 461 changes the refraction index by on/off operation which is caused by applying a voltage from the control device 403E via the signal line 462.

According to the twelfth embodiment, the control device 403E has the structure in which a light source and detecting unit 424E having a function corresponding to the light source and detecting unit 424B in the control device 403 in FIG. 46 is moved and arranged in the operating unit 406, without using the optical fiber 427a.

That is, light from the laser diode 445 becomes parallel beams by the collimator lens 464 and, thereafter, a part of the parallel beams is transmitted by the half mirror 465. The transmitted light is condensed by the condensing lens 466, passes through a pin hole of a pin hole forming element 467, and is incident on the collimator optical system 441.

The parallel beams formed by the collimator optical system 441 are made beams with a predetermined beam diameter by the second stop 418b. After that, the parallel beams are reflected by the gimbals scanner 439, are incident on the second pupil image forming optical system 417b, further pass through the half mirror 416, and are guided to the relay optical system 415.

The light guided by the relay optical system 415 is condensed and irradiated at the subject portion 412 at the short focusing point by the liquid crystal lens 461 of the objective optical system 413. The reflection light in the subject portion 412 passes through a contrary route and is incident on the pin hole forming element 467. In this case, among the light incident on the pin hole forming element 467, only the reflection light at the focus position of the objective optical system 413 passes through the pin hole and is incident on the condensing lens 466. Further, a part of the light is reflected by the half mirror 465, is condensed by the condensing lens 468, and is received by the optical detector 449.

The signal from the optical detector 449 is amplified by an amplifier 469, and is inputted to the calculating circuit 423 in the control device 403E by a signal line 470.

Other structure is the same as that according to the ninth embodiment (modification thereof).

According to the twelfth embodiment, in the normal observation, the endoscope 402E has a long focusing distance of the objective optical system 413 by reducing the refractive index of the liquid crystal lens 461. On the other hand, in the case of using the conjugate focusing optical system, the endoscope 402E has a short focusing distance of the objective optical system 413 by increasing the refractive index of the liquid crystal lens 461. In the normal observation, the endoscope 402E has a small NA by using the stop 418a. In the case of the conjugate focusing optical system, the endoscope 402E has a high NA by using the stop 418b, resulting a high resolution.

According to the twelfth embodiment, the endoscope 402E does not simultaneously perform both the normal observation and the observation of the micro image by the conjugate optical system, but can perform both the observations by time division. The advantages in the time division are almost the same as those according to the eleventh embodiment.

According to the twelfth embodiment, the endoscope 402E comprises the light source and detecting unit 424E of the conjugate focusing optical system in the operating unit 406. However, the light source and detecting unit 424 in FIG. 43 can be arranged in the operating unit 406 and the low-coherence light may be used.

Thirteenth Embodiment

Figure 51:
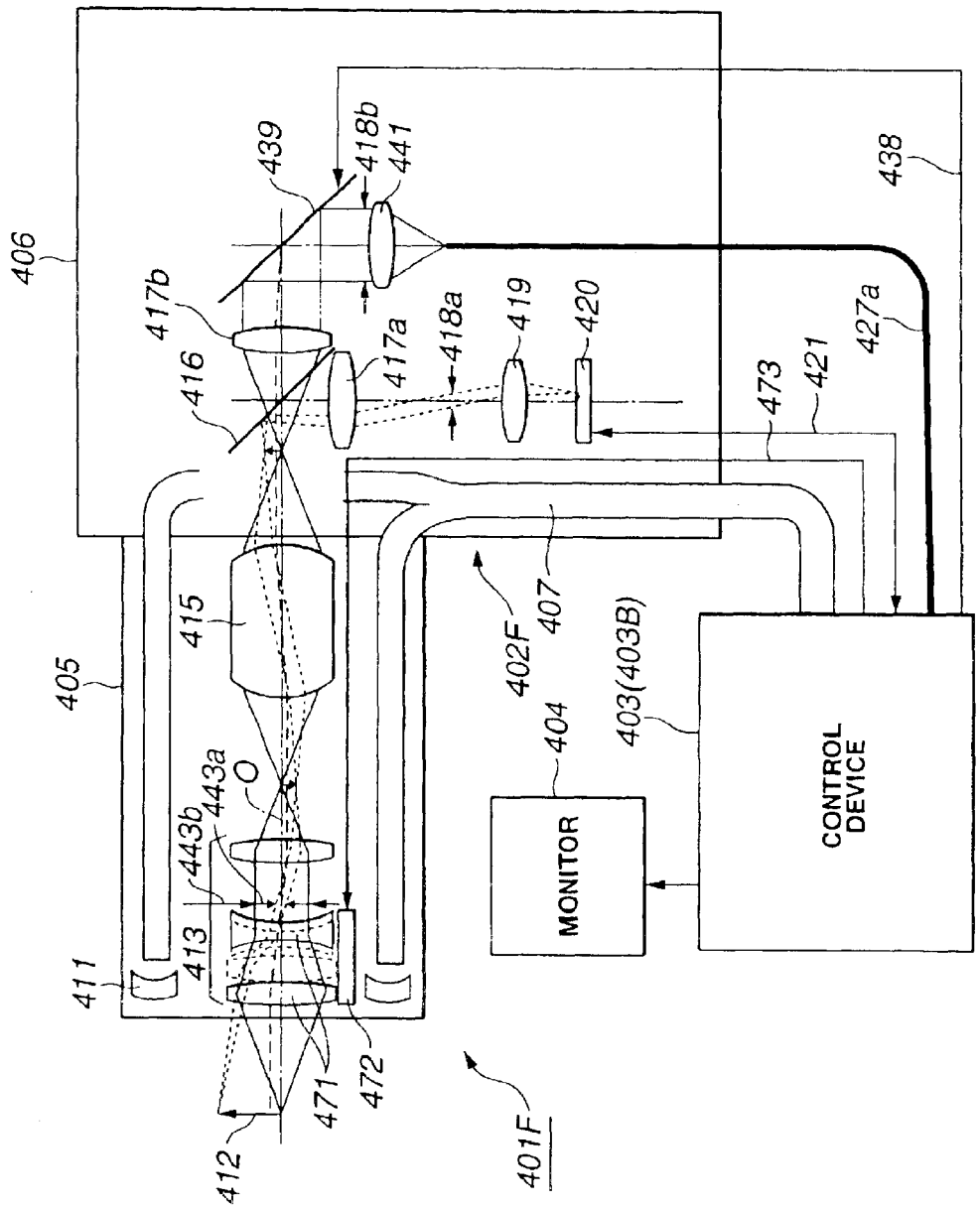
FIG. 51 is a diagram showing the entire structure of an endoscope apparatus according to a thirteenth embodiment of the present invention.

A thirteenth embodiment of the present invention will be described with reference to FIG. 51. FIG. 51 shows an endoscope apparatus 401F according to the thirteenth embodiment of the present invention. The endoscope apparatus 401F comprises an endoscope 402F, the control device 403 (or 403B), and the monitor 404.

Referring to FIG. 51, the endoscope 402F has a zooming optical system 471 as a front lens group, in place of the objective optical system 413 in the endoscope 402 in the FIG. 42. The zooming optical system 471 is moved in the optical axis 0 direction by an actuator 472 arranged near the zooming optical system 471.

Namely, the actuator 472 is connected to the calculating circuit 423 in the control device 403 (or 403B) by a signal line 473. By operation for instructing the switching by the keyboard or the like, the control device 403 (or 403B) can set the zooming optical system 471 for the normal observation or the observation with the low-coherence light or the conjugate focusing optical system.

Specifically, the zooming optical system 471 comprises lenses of positive power of a convex lens and negative power of a concave lens. In the normal observation, the zooming optical system 471 is set at a position shown by a dotted line in FIG. 51. In this case, the focusing distance of the objective optical system 413 is long.

When the observation with the low-coherence light or the conjugate focusing optical system is instructed, the zooming optical system 471 is variably set at a position shown by a solid line changing from the state shown by the dotted line in FIG. 51. In this case, the focusing distance of the objective optical system 413 is short.

Referring to FIG. 51, the objective optical system 413 is set so that the light is focused with the same distance from the edge surface of the inserting portion 405.

According to the thirteenth embodiment, the operating unit 406 in the endoscope 402F has almost the same structure as that of the optical system in the operating unit 406 of the endoscope 402 in FIG. 42, except for the pupil diameter converting optical system 442.

Specifically, the light outputted from the edge surface of the optical fiber 427a becomes parallel beams by the collimator optical system 441, and is inputted to the gimbals scanner 439 with a predetermined beam diameter by the second stop 418b. The reflection light is inputted to the second pupil image forming optical system 417b without using the pupil diameter converting optical system 442.

According to the thirteenth embodiment, the endoscope 402F uses the time division. However, similarly to the twelfth embodiment, according to the ninth embodiment, the observation range of the normal observation (macro image) can easily be widened. Advantageously, observation distances for the macro image and the micro image can be equal.

Fourteenth Embodiment

Figure 52:
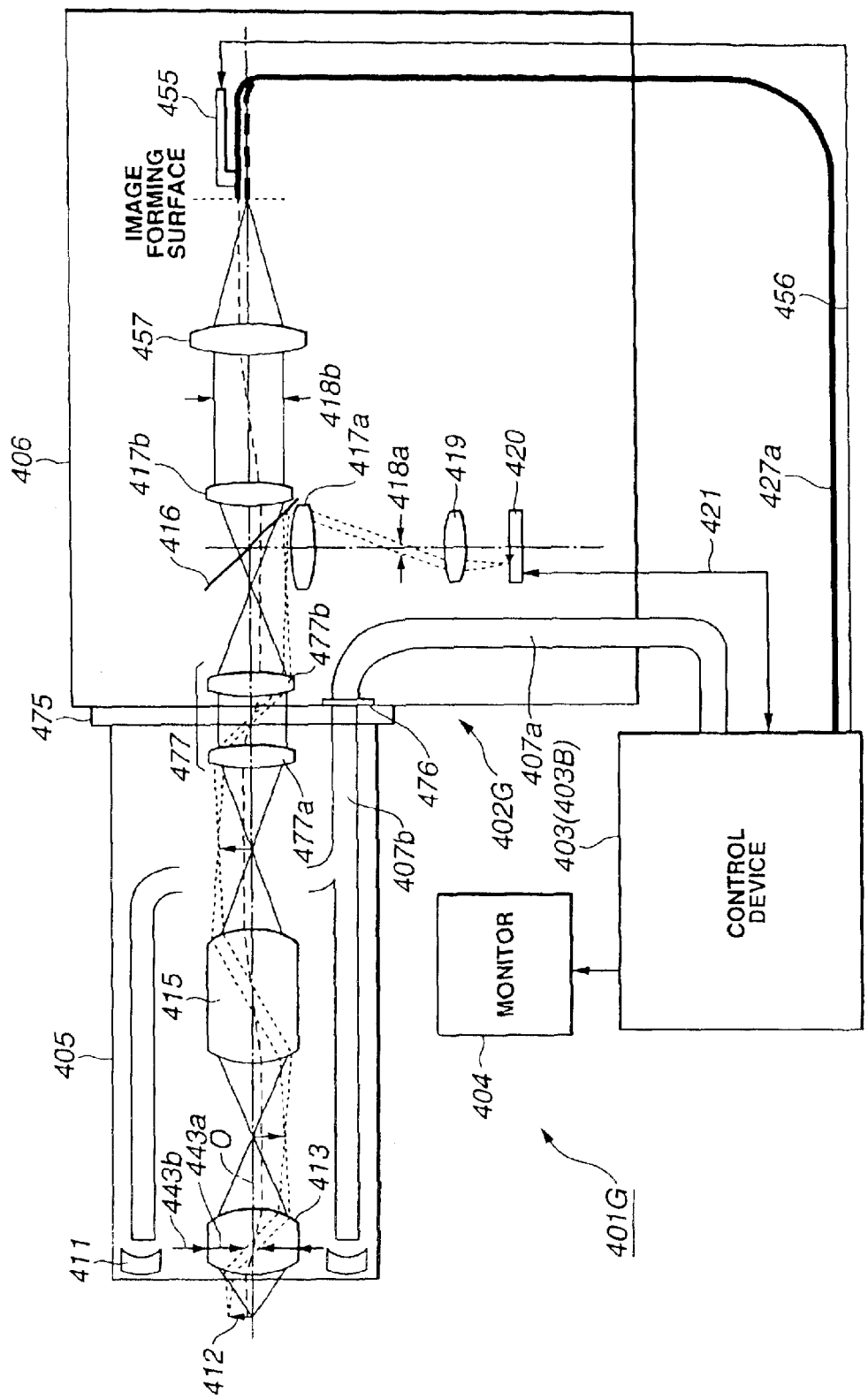
FIG. 52 is a diagram showing the entire structure of an endoscope apparatus according to a fourteenth embodiment of the present invention.

Next, a fourteenth embodiment of the present invention will be described with reference to FIG. 52. FIG. 52 shows an endoscope apparatus 401G according to the fourteenth embodiment of the present invention. The endoscope apparatus 401G comprises an endoscope 402G, the control device 403 (or 403B), and the monitor 404.

Referring to FIG. 52, the endoscope 402G has the endoscope 402 in which the inserting portion 405 and the operating unit 406 are detachable in the endoscope 402 in FIG. 42.

Therefore, in the endoscope 402G, the rear end of the inserting portion 405 is detachably connected to the front end of the operating unit 406 by an attaching portion (connecting portion) 475.

In this case, in the endoscope 402G, the fiber bundle 407 is divided into two portions (on the inserting portion 405 side and on the operating unit 406 side) by the attaching portion 475. Thus, according to the fourteenth embodiment, the endoscope 402G has a diffusing plate 476 at the front end of a fiber bundle 407a on the operating unit 406 side. Illumination light is transmitted to a fiber bundle 407b on the inserting portion 405 side via the diffusing plate 476. The endoscope 402G has two branched fiber bundle 407b in the inserting portion 405.

The endoscope 402G comprises a second relay optical system 477 on an optical path between the relay optical system 415 in the inserting portion 405 and the half mirror 416 in the operating unit 406. In the second relay optical system 477, one convex lens 477a is arranged on the inserting portion and another convex lens 477b is arranged on the operating unit 406. Light is guided by parallel beams of the pair of the lenses 477a and 477b at the attaching portion 475.

According to the fourteenth embodiment, as shown in FIG. 48, the piezo element 455 two-dimensionally drives the edge portion of the optical fiber 427a. Light outputted from the edge of the optical fiber 427a becomes parallel beams by the image forming optical system 457. The parallel beams have a predetermined beam diameter by the second stop 418b. After that, the parallel beams are condensed by the second pupil image forming optical system 417b. This light passes through the half mirror 416 and the one lens 477b of the second relay optical system 477, and is guided to the lens 477a on the inserting portion 405.

Other structure is the same as that according to the ninth embodiment.

According to the fourteenth embodiment, in the endoscope 402G, the inserting portion 405 is detachable to the operating unit 406. Therefore, the inserting portion 405 having different lengths can be attached and used.

Thus, according to the fourteenth embodiment, the endoscope apparatus 401G can use the endoscope 402G having varied lengths of the inserting portion depending on the used portion. The endoscope 402G increases the resolution by attaching the inserting portion 405 having the varied focusing distances of the objective optical system 413. Accordingly, the resolution is changed to be proper and is used in accordance with the used portion.

According to the fourteenth embodiment, in addition to the advantages according to the ninth embodiment, advantageously, the endoscope apparatus 401G can be used in the wider applications and can obtain the observation image in the state suitable to the used application.

According to the fourteenth embodiment, the endoscope apparatus 401G has the structure similar to the ninth embodiment. However, in the structure according to the ninth embodiment, according to the fourteenth embodiment, the inserting portion 405 and the operating unit 406 may be detachable and the endoscope apparatus 401G can be applied to other embodiments.

Figure 53A:
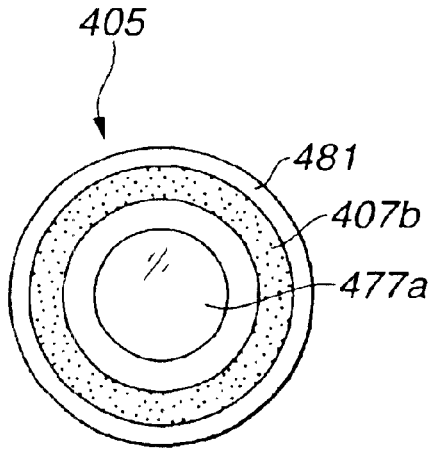
FIG. 53A is a view of an insertion portion from an attaching portion according to a modification.
Figure 53B:
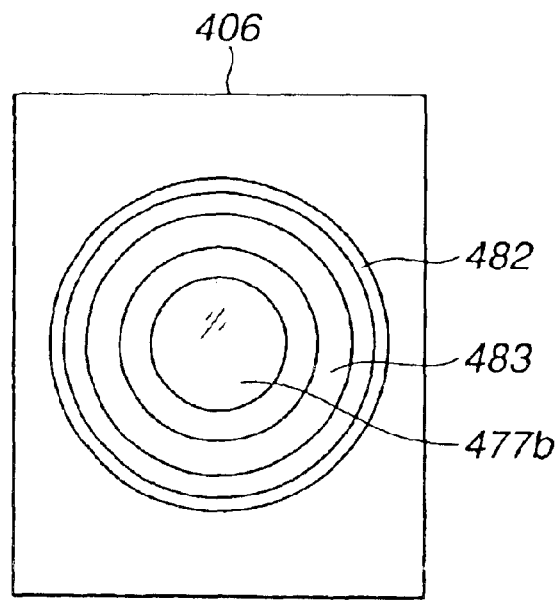
FIG. 53B is a view of an operation unit from the attaching portion according to the modification.

FIG. 53A is a view of an insertion portion from an attaching portion according to a modification of the fourteenth embodiment. FIG. 53B is a view of an operating unit 406 from the attaching portion according to the modification.

According to the modification, referring to FIG. 53A, in the inserting portion 405, the fiber bundle 407b is inserted into a hard outer tube 481 with a ring shape. Further, in the inserting portion 405, the lens 477a (arranged to the relay optical system 415 and near the back end thereof) is attached to a lens tube (not shown) along the central axis in the fiber bundle 407b.

The operating unit 406 comprises a circular attaching portion 482 into which the rear end of the inserting portion 405 is fit. The operating unit 406 has a white LED 483 at a circular portion opposed to the fiber bundle 407b in the attaching portion 482 (on the inserting portion 405). The operating unit 406 has the lens 477b opposed to the lens 477a on the inserting portion 405 in the white LED 483.

The present modification has substantially the same advantages as those according to the fourteenth embodiment.

Fifteenth Embodiment

Figure 54:
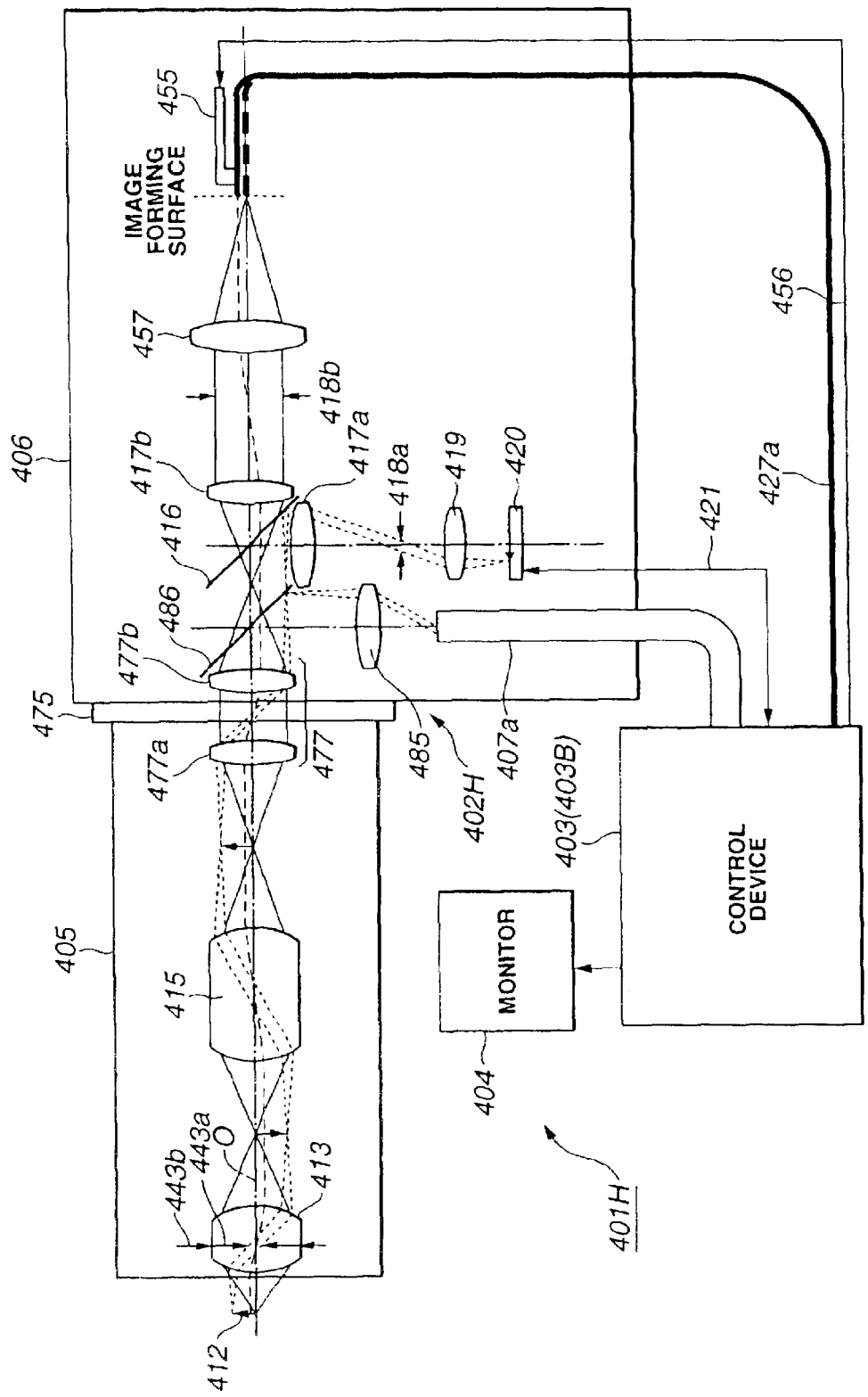
FIG. 54 is a diagram showing the entire structure of an endoscope apparatus according to a fifteenth embodiment of the present invention.

Next, a fifteenth embodiment will be described with reference to FIG. 54. FIG. 54 shows an endoscope apparatus 401H according to the fifteenth embodiment of the present invention. The endoscope apparatus 401H comprises an endoscope 402H, the control device 403 (or 403B), and the monitor 404.

In the endoscope 402G in FIG. 52, the endoscope 402H shown in FIG. 54 is formed by removing both the fiber bundle 407b arranged in the inserting portion 405 and the illumination optical system 411 at the edge. In the endoscope 402H, illumination light outputted from the edge surface of the fiber bundle 407a in the operating unit 406 is condensed by the illumination optical system 485, and a part of the condensed light is reflected by the second half mirror 486, thus guiding the illumination light on the second relay optical system 477.

The illumination light outputted from the edge surface of the fiber bundle 407a is set so that an output angle of the illumination light is approximately equal to an angle of the field of view in the case of forming an image of the illumination light to the image pick-up element 420 and, consequently, the image pick-up range can efficiently be illuminated. Other structure is the same as that in FIG. 52.

According to the fifteenth embodiment, the endoscope 402H does not need the illumination light transmitting means and the illumination optical system arranged in the inserting portion 405. Therefore, the inserting portion 405 can be thinner in diameter. Other structure has substantially the same advantages as those according to the ninth embodiment.

Sixteenth Embodiment

Figure 55:
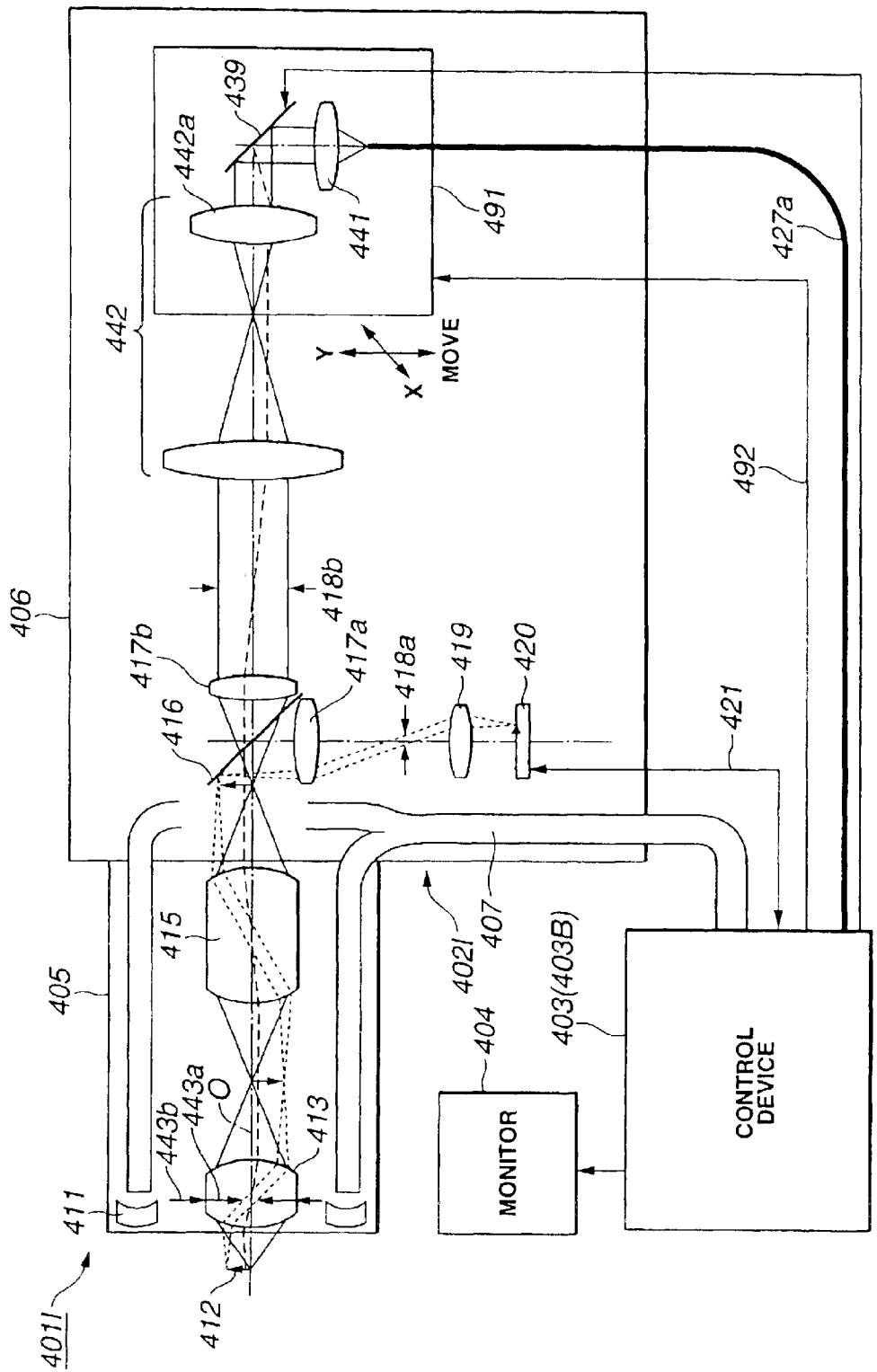
FIG. 55 is a diagram showing the entire structure of an endoscope apparatus according to a sixteenth embodiment of the present invention.

Next, a sixteenth embodiment of the present invention will be described with reference to FIG. 55. FIG. 55 shows an endoscope apparatus 401I according to the sixteenth embodiment. The endoscope apparatus 401I comprises an endoscope 402I, the control device 403 (or 403B), and the monitor 404.

Referring to FIG. 55, the endoscope 402I is formed by having an XY stage 491 having the periphery of the edge portion of the optical fiber 427a, the collimator optical system 441, the gimbals scanner 439, and a lens (designated by reference numeral 42a) on the gimbals scanner 439 in the pupil diameter converting optical system 442.

The XY stage 491 is connected to the control device 403 (or 403B) (in the calculating circuit 423) via a signal line 492 to be moved two-dimensionally in the X and Y directions perpendicular to the optical axis O by instructing operation of the keyboard or the like.

According to the ninth to fifteenth embodiment, the observation range of the low-coherence or conjugate focusing optical system exists near the determined position in the center around the optical axis O within the observation range in the normal observation. However, according to the sixteenth embodiment, the observation range of the low-coherence light or the conjugate focusing optical system can be changed by the one-dimensional movement in the X or Y direction or the two-dimensional movement in the X and Y directions.

Incidentally, the amount of movement of the XY stage 491 may be detected by detecting such as an encoder (not shown), etc. so that the observation range of the low-coherence light or the conjugate optical system in this case is displayed to a frame or the like in the image for the normal observation to be understood by the user.

Other structure is the same as that according to the ninth embodiment.

According to the sixteenth embodiment, since the endoscope 402I can change the enlargedly observation range, the user can change and set the enlargedly observation range and the operability can be improved. Other structure has the same advantages as those according to the ninth embodiment.

Not only the above-mentioned embodiments but also embodiments obtained by partly combining them can belong to the present invention.

For example, according to the sixteenth embodiment, the endoscope 402I has the structure in which the XY stage 491 is arranged to the structure according to the ninth embodiment and, however, it may be applied to other embodiments. In the endoscope 402G, the inserting portion 405 in FIG. 52 is detachable to the operating unit 406 by the attaching portion 475. However, the structure of the inserting portion 405 and the operating unit 406 does not have that shown in FIG. 52 but may have that according to other embodiments.

It should be understood that the present invention is not limited to those precise embodiments and various changes and modifications thereof could be made by one skilled in the art without departing from the spirit or scope of the invention as defined in the appended claims.

What is claimed is:

1. An optical imaging apparatus comprising:
   a low-coherence optical system which guides low-coherence light from a low-coherence light source to a subject portion and further guides return light from the subject portion to light receiving means;
   light separating means arranged to said low-coherence optical system, which separates the low-coherence light from said low-coherence light source into instrumentation light and reference light;
   horizontal scanning means arranged to said low-coherence optical system, which horizontally scans said subject portion with the instrumentation light separated by said light separating means;
   reference light reflecting means arranged to said low-coherence optical system, which reflects the reference light separated by said light separating means and returns the reflected light to said light separating means;

an objective optical system arranged to said low-coherence optical system, which condenses the instrumentation light horizontally scanned by said horizontal scanning means to said subject portion and further captures return instrumentation-light from said subject portion;

optical path length interlockingly adjusting means which interlockingly matches the length of an optical path of said instrumentation light to that of said reference light;

a single drive system that simultaneously drives both said objective optical system and said reference light reflecting means; and signal processing means which performs signal processing of an electronic signal converted photoelectrically by said light receiving means and obtains a surface image or a tomogram of said subject portion.

2. An optical imaging apparatus comprising:

an optical system which guides beams from a light source to a subject portion and further guides return light from said subject portion to light receiving means;

optical scanning means arranged to said optical system, which scans said subject portion with the beams from said light source;

an objective optical system arranged to said optical system, which condenses the beams for scanning by said optical scanning means to said subject portion and further captures return light from said subject portion;

positioning means arranged in a field of view for observation of said objective optical system, which comes into contact with said subject portion and performs positioning;

field of view position adjusting means which moves said positioning means relative to said objective optical system in a contact state of said positioning means with said subject portion and adjusts the position in the field of view of said objective optical system; and signal processing means which performs signal processing of an electronic signal converted photoelectrically by said light receiving means and obtains a surface image or a tomogram of said subject portion;

wherein said optical system has a conjugate focusing optical system between said light source and said objective optical system and said optical imaging apparatus is a conjugate focusing optical imaging apparatus which obtains a conjugate focusing image of said subject portion.

3. An optical imaging apparatus comprising:

an optical system which guides beams from a light source to a subject portion and further guides return light from said subject portion to light receiving means;

a normal optical system in which at least a part thereof is the same as said optical system and which has a numerical aperture smaller than that of said optical system, a focusing distance longer than that of said optical system, an object observation range wider than that of said optical system, or a diameter of the object observation range wider than that of said optical system, said normal optical system capturing a normal optical image of said subject portion and forming the captured normal optical image by image pick-up means; and signal processing means which performs signal processing of an electronic signal photoelectrically converted by said light receiving means, obtains a surface image or a tomogram of said subject portion, performs signal processing the electronic signal converted photoelectrically by said image pick-up means, and obtains a normal optical image;

wherein said optical system has a conjugate focusing optical system between said light source and said objective optical system and said optical imaging apparatus is a conjugate focusing optical imaging apparatus which obtains a conjugate focusing image of said subject portion.

4. An optical imaging apparatus according to claim 1, wherein said optical path length interlockingly adjusting means integrally holds at least said objective optical system and said reference light reflecting means, advances and regresses said objective optical system in an optical axis direction of the instrumentation light, and advances and regresses said reference light reflecting means in an optical axis direction of the reference light.

5. An optical imaging apparatus according to claim 1, wherein said low-coherence optical system has light output means which outputs the instrumentation light separated by said light separating means to said horizontal scanning means, and said optical path length interlockingly adjusting means integrally holds at least said objective optical system and said light output means, and advances and regresses said objective optical system and said light output means in an optical axis direction of the instrumentation light.

6. An optical imaging apparatus according to claim 1, wherein said low-coherence optical system has light output means which outputs the instrumentation light separated by said light separating means to said horizontal scanning means, and said optical path length interlockingly adjusting means holds said light output means and said reference light reflecting means integrally with said objective optical system, advances and regresses said objective optical system and said light output means in an optical axis direction of the instrumentation light, and advances and regresses said reference light reflecting means in an optical axis of the reference light.

7. An optical imaging apparatus according to claim 1, further comprising an optical scanning probe which transmits the beams of said light source to said subject portion and receives the return light from said subject portion, wherein said optical scanning probe is a hand-held probe having at least said objective optical system.

8. An optical imaging apparatus according to claim 1, further comprising an optical scanning probe which transmits the beams of said light source to said subject portion and receives the return light from said subject portion, wherein said optical scanning probe inserted and arranged to an endoscope or a channel for inserting treatment appliance, has at least said objective optical system.

9. An optical imaging apparatus according to claim 2, wherein said light source is a low-coherence light source which generates low-coherence light, and said optical imaging apparatus is a low-coherence optical imaging apparatus which separates the low-coherence light from said light source into the instrumentation light and the reference light, irradiates said subject portion with the instrumentation light, and obtains a low-coherence light image of said subject portion by making the reference light coherent to the return light from said subject portion.

10. An optical imaging apparatus according to claim 2, wherein said field of view position adjusting means moves said positioning means in the horizontal and vertical directions of said objective optical system.

11. An optical imaging apparatus according to claim 2, wherein said field of view position adjusting means has contact keeping means which keeps a contact state of said positioning means with said subject portion.

12. An optical imaging apparatus according to claim 2, further comprising an optical scanning probe which transmits the beams from said light source to said subject portion and receives the return light from said subject portion, and said optical scanning probe is a hand-held probe having at least said objective optical system.

13. An optical imaging apparatus according to claim 2, further comprising an optical scanning probe which transmits the beams from said light source to said subject portion and receives the return light from said subject portion, wherein said optical scanning probe inserted and arranged to an endoscope or a channel for inserting treatment appliance, has at least said objective optical system.

14. An optical imaging apparatus according to claim 3, wherein said light source is a low-coherence light source which generates low-coherence light, and said optical imaging apparatus is a low-coherence optical imaging apparatus which separates the low-coherence light from said light source into the instrumentation light and the reference light, irradiates said subject portion with the instrumentation light, and obtains a low-coherence light image of said subject portion by making the reference light coherent to the return light from said subject portion.

15. An optical imaging apparatus according to claim 3, further comprising means for differing the numerical apertures, said means having varied apertures depending on the optical systems.

16. An optical imaging apparatus according to claim 3, further comprising means for differing the numerical apertures, said means varying apertures of the stop.

17. An optical imaging apparatus according to claim 3, further comprising means for differing the focusing distances, said means comprising an optical system having two focusing distances.

18. An optical imaging apparatus according to claim 3, further comprising means for differing the focusing distance, said means varying a part of the optical system.

* * * * *